US009662385B2

(12) United States Patent
Dominowski et al.

(10) Patent No.: US 9,662,385 B2
(45) Date of Patent: *May 30, 2017

(54) ADJUVANT COMPOSITIONS

(71) Applicant: Zoetis Services LLC, Florham Park, NJ (US)

(72) Inventors: Paul Joseph Dominowski, Kalamazoo, MI (US); Ramasamy Mannar Mannan, Woburn, MA (US); Richard Lee Krebs, Ashland, NE (US); James Richard Thompson, Portage, MI (US); Tedd Alan Childers, Portage, MI (US); Mary Kathryn Olsen, Kalamazoo, MI (US); Robert John Yancey, Jr., Portage, MI (US); Risini Dhammika Weeratna, Ottawa (CA); Shucheng Zhang, Shanghai (CN); Cedo Martin Bagi, Branford, CT (US)

(73) Assignee: Zoetis Services LLC, Parsippany, NJ (US)

( * ) Notice: Subject to any disclaimer, the term of this patent is extended or adjusted under 35 U.S.C. 154(b) by 53 days.

This patent is subject to a terminal disclaimer.

(21) Appl. No.: 14/013,299

(22) Filed: Aug. 29, 2013

(65) Prior Publication Data
US 2014/0056940 A1 Feb. 27, 2014

Related U.S. Application Data

(62) Division of application No. 12/490,767, filed on Jun. 24, 2009, now Pat. No. 8,580,280.

(Continued)

(51) Int. Cl.
A61K 45/00 (2006.01)
A61K 39/39 (2006.01)
(Continued)

(52) U.S. Cl.
CPC ............ *A61K 39/39* (2013.01); *A61K 39/002* (2013.01); *A61K 39/0011* (2013.01);
(Continued)

(58) Field of Classification Search
None
See application file for complete search history.

(56) References Cited

U.S. PATENT DOCUMENTS 4,264,587 A 4/1981 Pedersen et al.
5,026,546 A 6/1991 Hilgers et al.
(Continued)

FOREIGN PATENT DOCUMENTS

WO 93/14190 A1 7/1993
WO 94/04174 3/1994
(Continued)

OTHER PUBLICATIONS

Usinger. A comparison of antibody responses to veterinary vaccine antigens potentiated by different adjuvants. Vaccine. 1997; 15(17/18): 1902-1907.*

(Continued)

*Primary Examiner* — Janet L Andres
*Assistant Examiner* — Stuart W Snyder
(74) *Attorney, Agent, or Firm* — Vyacheslav Vasilyev

(57) ABSTRACT

This invention relates to adjuvant formulations comprising various combinations of triterpenoids, sterols, immunomodulators, polymers, and Th2 stimulators; methods for making the adjuvant compositions; and the use of the adjuvant formulations in immunogenic and vaccine compositions with different antigens. This invention further relates to the use of the formulations in the treatment of animals.

16 Claims, 1 Drawing Sheet

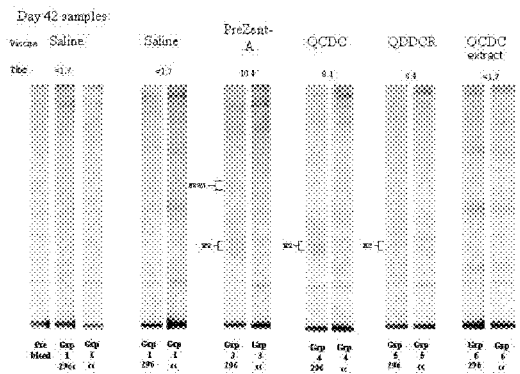

Response to BVDV NS2/3 Protein

Related U.S. Application Data

(60) Provisional application No. 61/076,232, filed on Jun. 27, 2008, provisional application No. 61/214,557, filed on Apr. 24, 2009.

(51) Int. Cl.

| | | |
|---|---|---|
| A61K 39/00 | (2006.01) | |
| A61K 39/012 | (2006.01) | |
| A61K 39/02 | (2006.01) | |
| A61K 39/108 | (2006.01) | |
| A61K 39/12 | (2006.01) | |
| A61K 39/145 | (2006.01) | |
| A61K 39/15 | (2006.01) | |
| A61K 39/21 | (2006.01) | |
| A61K 39/215 | (2006.01) | |
| A61K 39/002 | (2006.01) | |

(52) U.S. Cl.
CPC ........ *A61K 39/012* (2013.01); *A61K 39/0208* (2013.01); *A61K 39/0241* (2013.01); *A61K 39/0258* (2013.01); *A61K 39/12* (2013.01); *A61K 39/145* (2013.01); *A61K 39/15* (2013.01); *A61K 39/21* (2013.01); *A61K 39/215* (2013.01); *A61K 2039/521* (2013.01); *A61K 2039/5252* (2013.01); *A61K 2039/5254* (2013.01); *A61K 2039/54* (2013.01); *A61K 2039/55* (2013.01); *A61K 2039/552* (2013.01); *A61K 2039/55505* (2013.01); *A61K 2039/55511* (2013.01); *A61K 2039/55555* (2013.01); *A61K 2039/55561* (2013.01); *A61K 2039/55566* (2013.01); *A61K 2039/55572* (2013.01); *A61K 2039/55577* (2013.01); *C12N 2720/12334* (2013.01); *C12N 2720/12351* (2013.01); *C12N 2740/13034* (2013.01); *C12N 2740/13051* (2013.01); *C12N 2760/16134* (2013.01); *C12N 2760/16151* (2013.01); *C12N 2770/20034* (2013.01); *C12N 2770/20051* (2013.01); *C12N 2770/24334* (2013.01); *C12N 2770/24351* (2013.01)

(56) References Cited

U.S. PATENT DOCUMENTS

| | | | |
|---|---|---|---|
| 5,057,540 A | | 10/1991 | Kensil et al. |
| 5,679,354 A | * | 10/1997 | Morein et al. ............. 424/278.1 |
| 6,406,705 B1 | | 6/2002 | Davis et al. |
| 6,764,682 B1 | | 7/2004 | Kandil et al. |
| 6,846,489 B1 | | 1/2005 | Garcon et al. |
| 7,122,191 B2 | | 10/2006 | Dominowski et al. |
| 7,488,490 B2 | | 2/2009 | Davis et al. |
| 8,460,679 B2 | | 6/2013 | Mannan et al. |
| 8,580,280 B2 | * | 11/2013 | Dominowski ..... A61K 39/0011 424/278.1 |
| 2003/0064079 A1 | | 4/2003 | Goudie et al. |
| 2003/0086938 A1 | | 5/2003 | Jensen et al. |
| 2003/0118635 A1 | | 6/2003 | Dalsgaard et al. |
| 2003/0165478 A1 | | 9/2003 | Sokoll |
| 2003/0224010 A1 | | 12/2003 | Davis et al. |
| 2004/0191214 A1 | | 9/2004 | Lau et al. |
| 2004/0258701 A1 | | 12/2004 | Dominowski et al. |
| 2006/0239963 A1 | | 10/2006 | Morein et al. |
| 2006/0251674 A1 | | 11/2006 | Dominowski et al. |
| 2008/0187546 A1 | | 8/2008 | Wasmoen et al. |
| 2008/0292663 A1 | | 11/2008 | Gerber |

FOREIGN PATENT DOCUMENTS

| | | | |
|---|---|---|---|
| WO | 95/34308 | | 12/1995 |
| WO | 98/48835 | | 11/1998 |
| WO | 01/54720 A1 | | 8/2001 |
| WO | 03/003941 | | 1/2003 |
| WO | 03/028760 | | 4/2003 |
| WO | WO 03028760 | * | 4/2003 |
| WO | 2004/067031 | | 8/2004 |
| WO | 2005/107797 A1 | | 11/2005 |
| WO | 2007/089753 A2 | | 8/2007 |
| WO | 2008/157659 | | 12/2008 |

OTHER PUBLICATIONS

Rajput, et al. Adjuvant effects of saponins on animal immune responses. Journal of Zhejiang University, Science, B. 2007; 8(3): 153-161.*
Evans, et al. Characterization and biological evaluation of a microparticle adjuvant formulation for plasmid DNA vaccines. Journal of Pharmaceutical Sciences. 2004; 93(7): 1924-1939.*
Hilgers, et al. Alkyl-esters of polyacrylic acid as vaccine adjuvants. Vaccine, 1998; 16(16): 1575-1581.*
Jia et al. Synthesis and antibacterial activities of quaternary ammonium salt of chitosan. Carbohydrate Research 333 (2001) 1-6.*
Langhammer et al. Antibodies neutralizing feline leukaemia virus (FeLV) in cats immunized with the transmembrane envelope protein p15E. Immunology, 2005; 117: 229-237.*
Lacaille-Dubois and Wagner, "A review of the biological and pharmacological activities of saponins", Phytomedicine, 2(4):363-386, 1996.
Ozel et al., "Quaternary Structure of the Immunostimulating Complex (Iscom)", Journal of Ultrastructure and Molecular Structure Research, 102:240-248, 1989.
Gall, "The Adjuvant Activity of Aliphatic Nitrogenous Bases", Immunology, 11:369-386, 1966.
Korsholm et al., "The adjuvant mechanism of cationic dimethyldioctadecylammonium liposomes", Immunology, 121:216-226, 2007.
Katz et al., "Comparison of dimethyl dioctadecyl ammonium bromide, Freund's complete adjuvant and mineral oil for induction of humoral antibodies, cellular immunity and resistance to Newcastle disease virus in chickens", FEMS Immunology and Medicinal Microbiology, 7:303-314, 1993.
Dalloul and Lillehoj, "Poultry coccidiosis: recent advancements in control measures and vaccine development", Expert Rev. Vaccines, 5(1):143-163, 2006.
Lillehoj et al., "Embryo Vaccination Against Eimeria Tenella and E. Acervulina Infections Using Recombinant Proteins and Cytokine Adjuvants", J. Parasitol., 91(3):666-673, 2005.
Lillehoj et al., "Resistance to Intestinal Coccidiosis Following DNA Immunization with the Cloned 3-1E Eimeria Gene Plus IL-2, IL-15, and IFN-gamma", Avian Diseases, 49:112-117, 2005.
PCT International Search Report, PCT/IB2009/052724, mailed Aug. 2, 2010 (6 pages).
Autran et al., "Therapeutic Vaccines for Chronic Infections", Science, 305:205-208, 2004.
Mahdavi and Monk, "Vaccines Against Human Papillomavirus and Cervical Cancer: Promises and Challenges", The Oncologist, 10:528-538, 2005.
Usinger, "A comparison of antibody responses to veterinary vaccine antigens potentiated by different adjuvants", Vaccine, 15(17/18):1902-1907, 1997.
Rajput et al., "Adjuvant effects of saponins on animal immune responses", Journal of Zhejiang University Science B, 8(3):153-161, 2007.
Evans et al., "Characterization and Biological Evaluation of a Microparticle Adjuvant Formulation for Plasmid DNA Vaccines", Journal of Pharmaceutical Sciences, 93(7):1924-1939, 2004.
Carcaboso et al., "Potent, long lasting systemic antibody levels and mixed Th1/Th2 immune response after nasal immunization with malaria antigen loaded PLGA microparticles", Vaccine, 22(11-12):1423-1432, 2004.
Hoover et al., "Efficacy of an Inactivated Feline Leukemia Virus Vaccine", AIDS Research and Human Retroviruses, 12(5):379-383, 1996.

(56) References Cited

OTHER PUBLICATIONS

Yamamoto et al., "Experimental Vaccine Protection Against Feline Immunodeficiency Virus", AIDS Research and Human Retroviruses, 7(11):911-922, 1991.

Perez Filgueira et al., "Passive protection to bovine rotavirus (BRV) infection induced by a BRV VP8* produced in plants using a TMV-based vector", Arch. Virol., 149(12):2337-2348, 2004.

Karaca et al., "Evaluation of the ability of canarypox-vectored equine influenza virus vaccines to induce humoral immune responses against canine influenza viruses in dogs", Am. J. Vet. Res., 68(2):208-212, 2007.

Berezin et al., "Immunostimulating complexes incorporating Eimeria tenella antigens and plant saponins as effective delivery system for coccidia vaccine immunization", J. Parasitol., 94(2):381-385, 2008.

Grego et al., "Development and application of an enzyme-linked immunosorbent assay for detection of bovine viral diarrhea antibody based on Erns glycoprotein expressed in a baculovirus System", J. Vet. Diagn. Invest., 19:21-27, 2007.

Van Drunen Littel-Van Den Hurk et al., "Strategies for induction of protective immunity to bovine herpesvirus-1 in newborn calves with maternal antibodies", Vaccine, 26:3103-3111, 2008.

Ralph et al., "Reticulum cell sarcoma: an effector cell in antibody-dependent cell-mediated immunity", J. Immunol., 114(No. 2/Part 2):898-905, 1975.

* cited by examiner

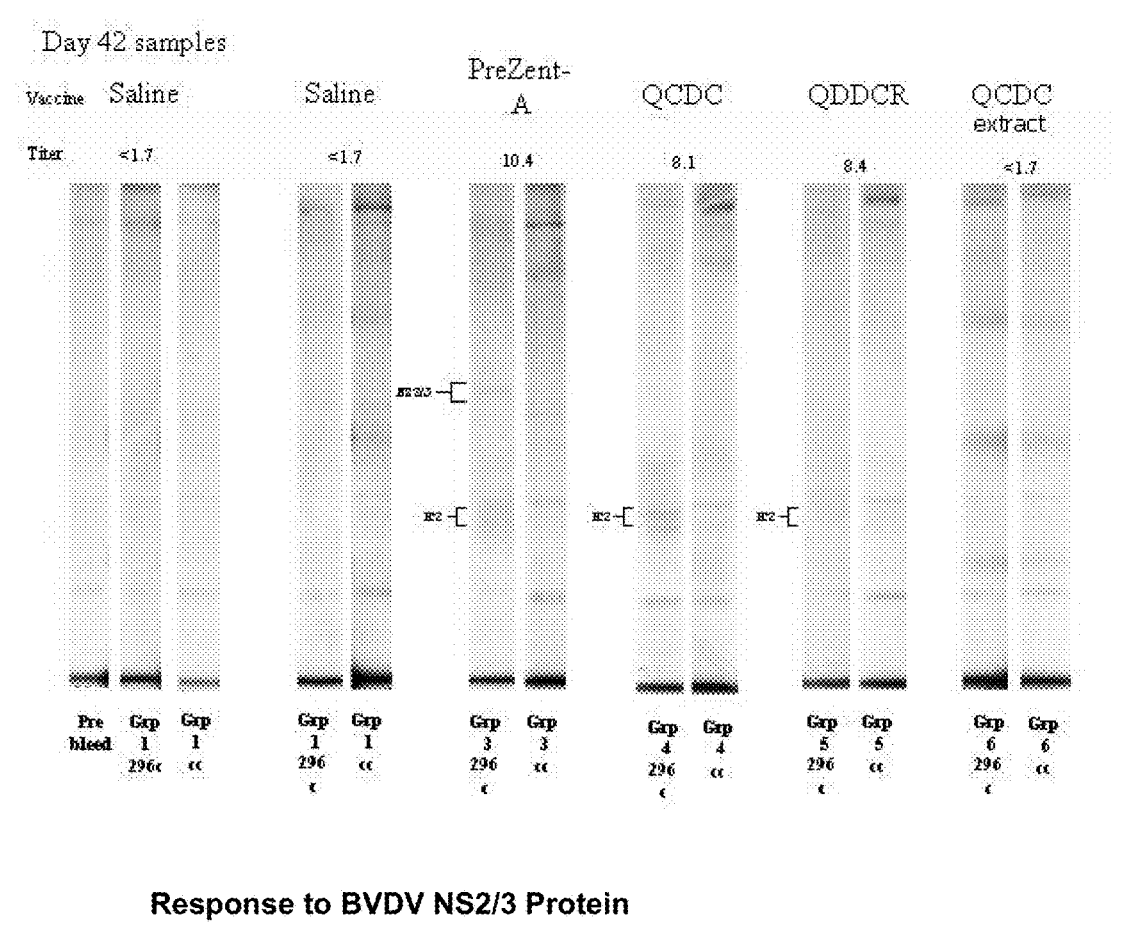

Response to BVDV NS2/3 Protein

ADJUVANT COMPOSITIONS

CROSS-REFERENCE TO RELATED APPLICATIONS

This application is a divisional of U.S. application Ser. No. 12/490,767 filed Jun. 24, 2009, now U.S. Pat. No. 8,580,280, granted Nov. 12, 2013, which is a non-provisional of U.S. Provisional Application Ser. No. 61/076,232 filed Jun. 27, 2008, and U.S. Provisional Application Ser. No. 61/214,557 filed Apr. 24, 2009, both abandoned.

BACKGROUND OF THE INVENTION

Field of Invention

This invention relates generally to novel adjuvant formulations for enhancing the immune response to antigens for use in immunogenic and vaccine compositions, without producing toxic or undesirable side effects in the subject. This invention also relates to methods of preparation and use of the adjuvant, immunogenic, and vaccine compositions.

History and Description of Related Art

Bacterial, viral, and parasitic infections are wide spread in humans and animals. Diseases caused by these infectious agents are often resistant to antimicrobial pharmaceutical therapy, leaving no effective means of treatment. Consequently, a vaccinology approach is increasingly used to control infectious disease. A whole infectious pathogen can be made suitable for use in a vaccine formulation after chemical inactivation or appropriate genetic manipulation. Alternatively, a protein subunit of the pathogen can be expressed in a recombinant expression system and purified for use in a vaccine formulation. Vaccines can be made more efficacious by including an appropriate adjuvant in the composition.

There is also an increased interest in using a vaccinology approach for treating cancer in animals and humans. This therapeutic approach to the treatment of cancer involves vaccinating cancer patients with a vaccine comprising a tumor-specific antigen and an adjuvant. However, none of the many cancer vaccines of this nature in development has been approved by regulatory authorities. Vaccines have not been shown to shrink tumors, a standard measure of a cancer drug's effectiveness.

The term 'adjuvant' generally refers to any material that increases the humoral or cellular immune response to an antigen. Adjuvants are used to accomplish two objectives: They slow the release of antigens from the injection site, and they stimulate the immune system. Traditional vaccines are generally composed of a crude preparation of inactivated or killed or modified live pathogenic microorganisms. The impurities associated with these cultures of pathological microorganisms may act as an adjuvant to enhance the immune response. However, the immunity invoked by vaccines that use homogeneous preparations of pathological microorganisms or purified protein subunits as antigens is often poor. The addition of certain exogenous materials such as an adjuvant therefore becomes necessary. Further, synthetic and subunit vaccines are expensive to produce. The addition of an adjuvant may permit the use of a smaller dose of antigen to stimulate a similar immune response, thereby reducing the production cost of the vaccine. Thus, the effectiveness of some injectable medicinal agents may be significantly increased when the agent is combined with an adjuvant.

Many factors must be taken into consideration in the selection of an adjuvant. An adjuvant should cause a relatively slow rate of release and absorption of the antigen in an efficient manner with minimum toxic, allergenic, irritating, and other undesirable effects to the host. To be desirable, an adjuvant should be non-viricidal, biodegradable, capable of consistently creating a high level of immunity, capable of stimulating cross protection, compatible with multiple antigens, efficacious in multiple species, non-toxic, and safe for the host (eg, no injection site reactions). Other desirable characteristics of an adjuvant are that it is capable of micro-dosing, is dose sparing, has excellent shelf stability, is amenable to drying, can be made oil-free, can exist as either a solid or a liquid, is isotonic, is easily manufactured, and is inexpensive to produce. Finally, it is highly desirable for an adjuvant to be configurable so as to induce either a humoral or cellular immune response or both, depending on the requirements of the vaccination scenario. However, the number of adjuvants that can meet the above requirements is limited.

The choice of an adjuvant depends upon the needs for the vaccine, whether it be an increase in the magnitude or function of the antibody response, an increase in cell mediated immune response, an induction of mucosal immunity, or a reduction in antigen dose. A number of adjuvants have been proposed, however, none has been shown to be ideally suited for all vaccines. The first adjuvant reported in the literature was Freund's Complete Adjuvant (FCA) which contains a water-in-oil emulsion and extracts of mycobacterium. Unfortunately, FCA is poorly tolerated and it can cause uncontrolled inflammation. Since the discovery of FCA over 80 years ago efforts have been made to reduce the unwanted side effects of adjuvants.

Some other materials that have been used as adjuvants include metallic oxides (e.g., aluminum hydroxide), alum, inorganic chelates of salts, gelatins, various paraffin-type oils, synthesized resins, alginates, mucoid and polysaccharide compounds, caseinates, and blood-derived substances such as fibrin clots. While these materials are generally efficacious at stimulating the immune system, none has been found to be entirely satisfactory due to adverse effects in the host (e.g., production of sterile abcesses, organ damage, carcinogenicity, or allergenic responses) or undesirable pharmaceutical properties (e.g., rapid dispersion or poor control of dispersion from the injection site, or swelling of the material).

Synthesized oils and petroleum derivatives have been used as adjuvants because they exhibit relatively slow dispersion in the body, but they may be undesirable as they frequently are broken down into aromatic hydrocarbons, which may be carcinogenic. Furthermore, some of these substances have been found to be capable of producing sterile abcesses and may never be completely eliminated by the body. Oils when appropriately selected and formulated at proper concentrations can be relatively safe and nontoxic.

Saponins obtained from bark of the South American tree *Quillaja saponaria* have been used as adjuvants for some time. See Lacaille-Dubois, M and Wagner H. (A review of the biological and pharmacological activities of saponins. Phytomedicine vol 2 pp 363-386. 1996). Many of the veterinary vaccines in use today contain Quil A, which is the saponin fraction from the bark of the South American tree *Quillaja saponaria molina*. Further fractionation of Quil A has yielded sub-fractions, including QS-7, QS-17, QS-18, and QS-21. (See U.S. Pat. No. 5,057,540)

The use of saponins as adjuvants is associated with a number of disadvantages. Saponins are soluble and thus stimulate a non-specific immune response. The goal of vaccinology, however, is to stimulate a targeted response to a specific antigen or antigens. Saponins have a strong affinity for cholesterol. They form a complex with the cholesterol found in cell membranes causing hemolysis of the cell. They have also been shown to cause necrosis at the injection site and to be difficult to formulate into particulate structures. When used in vaccines containing modified live enveloped viruses, saponins disrupt the viral envelope and thereby inactivate the viral antigens.

To overcome the hemolytic and viricidal properties of Quil A, it has been combined with cholesterol and phospholipids, which form a specific structure known as an immunostimulatory complex (ISCOM) or ISCOM matrix (ISCOMATRIX). See Ozel M., et. al.; J. Ultrastruc. and Molec. Struc. Re 102, 240-248 (1989). ISCOMs, when combined with an antigen, generally induce a Th1 cytotoxic T-cell response. However, while greatly reducing the hemolytic properties of Quil A, combining Quil A with cholesterol does not completely eliminate them. Another limitation of ISCOMs is that a protein antigen must have hydrophobic domains large enough to interact with the ISCOM in order to be incorporated into an ISCOM. A protein which is highly hydrophilic cannot be incorporated into an ISCOM. Finally, ISCOMs can stimulate an undesirable autoimmune reaction in the subject.

Immunomodulators have been used as adjuvants, with examples including dimethyl dioctadecyl ammonium bromide (hereinafter, "DDA"), and avirdine. DDA is a lipophilic quaternary ammonium compound (amine) with two 18 carbon alkyl chains and two methyl groups bound to a positively charged quaternary ammonium molecule with a molecular weight of 631. Its use as an adjuvant was discovered by Gall, (Immunol. V. 11, p. 369, 1966). DDA is reported to stimulate strong cell mediated immune responses, and has also been shown to induce humoral immune responses. Many papers have been published showing efficacy of DDA as an adjuvant for protein antigens, haptens, tumors, viruses, protozoa and bacteria. (See Korsholm, K S., et al., Immunology, vol. 121, pp. 216-226, 2007.) Most studies have been performed in laboratory animals, while only a few have been carried out in larger animals such as chickens (See Katz, D., et al. FEMS Immunol Med. Microbiol. Vol 7(4):303-313, 1993.), pigs, and cattle. DDA is effective in inducing a delayed-type hypersensitivity (DTH) reaction in both laboratory animals and large animals. However, it is poorly soluble in water.

Polymers have also been used as adjuvants, with examples including diethyl-aminoethyl (DEAE)-dextran, polyethelyne glycol, and polyacrylic acid (e.g., CARBOPOL®). The polysaccharide DEAE-dextran is known in the art as a very strong adjuvant. However, it has been associated with unacceptable reactogenicity. CARBOPOL® polymers are polymers of acrylic acid cross-linked with polyalkenyl ethers or divinyl glycol. CARBOPOL® has been used in a number of vaccines, but its use as an adjuvant has not been proven.

Some adjuvants have been shown to stimulate a Th2 response, with examples including N-(2-Deoxy-2-L-leucylamino-b-D-glucopyranosyl)-N-octadecyldodecanoylamide hydroacetate, also known by the trade name Bay R1005® when in its acetate form, and aluminum. Bay R1005® in combination with purified virus vaccines or subunit vaccines led to increased production of antibody in virus-challenged mice. Preclinical trials in other animal species (pig, sheep, horse) gave comparable results with respect to antibody production. The increase in antibody synthesis induced by Bay R1005® is specifically dependent on the antigen and is not the result of polyclonal stimulation.

Prior to this invention, no adjuvant formulation possessed the broad range of desirable characteristics an ideal adjuvant should have. There has been an effort to find new adjuvants for vaccines that would overcome the deficiencies of conventional ones. In particular, an adjuvant formulation which elicits potent cell-mediated and humoral immune responses to a wide range of antigens in humans and animals, yet lacks the side effects and formulation difficulties of conventional adjuvants, is highly desirable.

SUMMARY OF THE INVENTION

This invention relates to novel adjuvant, immunogenic, and vaccine compositions. In particular, this invention relates to adjuvant formulations comprising Th1 stimulators, immunomodulators, polymers, and Th2 stimulators. This invention also relates to immunogenic and vaccine compositions comprising such adjuvant formulations and one or more antigens, as well as methods of preparing the adjuvant and vaccine compositions.

In one embodiment, the adjuvant compositions comprise a combination of a saponin, a sterol, and a quaternary ammonium compound. In one embodiment, the adjuvant combination comprises Quil A, cholesterol, and DDA.

In another embodiment, the adjuvant compositions comprise a combination of a saponin, a sterol, a quaternary ammonium compound, and a polymer. In one embodiment, the adjuvant combination is Quil A, cholesterol, DDA, and polyacrylic acid.

In another embodiment, the adjuvant compositions comprise a combination of a saponin, a sterol, a quaternary ammonium compound, a polymer, and glycolipid. In one embodiment, the adjuvant combination is Quil A, cholesterol, DDA, polyacrylic acid, and Bay R1005®.

In one embodiment, an immunogenic composition comprising an adjuvant formulation and an immunologically effective amount of an antigen, wherein the adjuvant formulation comprises a saponin, a sterol, a quaternary ammonium compound, and a polymer, is prepared by the process comprising
  a) preparing a composition of the antigen in a buffer,
  b) adding the saponin to the composition of step a;
  c) adding the sterol to the composition of step b;
  d) adding the quaternary ammonium compound to the composition of step c,
  e) adding the polymer to the composition of step d.

In one embodiment of this process, the saponin is Quil A, the sterol is cholesterol, the quaternary ammonium compound is DDA, and the polymer is polyacrylic acid.

In one embodiment, a vaccine comprising an adjuvant formulation and an immunologically effective amount of an antigen, wherein the adjuvant formulation comprises a saponin, a sterol, a quaternary ammonium compound, a polymer, and a glycolipid is prepared by the process comprising
  a) preparing a composition of the antigen in a buffer,
  b) adding the saponin to the composition of step a;
  c) adding the sterol to the composition of step b;
  d) adding the quaternary ammonium compound to the composition of step c,
  e) adding the polymer to the composition of step d, and
  f) adding the glycolipid to the composition of step e.

In one embodiment of this process, the saponin is Quil A, the sterol is cholesterol, the quaternary ammonium compound is DDA, the polymer is polyacrylic acid, and the glycolipid is Bay R1005®.

It has been found that the adjuvant compositions reported herein have surprising and unexpected properties beyond what one would expect from such a combination. It has been surprisingly found that the viricidal property of Quil A/cholesterol is eliminated in these adjuvant compositions. They are suitable as a diluent for lyophilized modified live viral antigens. The adjuvant compositions described herein are configurable to elicit an extremely potent immune response directed either to a cell-mediated immune response, a humoral immune response, or both. Additionally, injection site reactions can be largely avoided by use of these adjuvant formulations. The reactogenicity is lower than that of several of the individual components that comprise the combination adjuvants. In addition, these adjuvant formulations provide long-term storage capability.

Applicants have discovered that these novel adjuvant compositions are highly immunogenic when combined with one or more of a number of different antigens across a wide range of species. They can be used with one or more viral, bacterial, parasitic, recombinant protein, and synthetic peptide antigens, and combinations thereof. The novel vaccine adjuvant compositions can be used in therapeutic vaccines to treat cancer.

The present invention therefore provides adjuvant, immunogenic, and vaccine compositions. Additionally provided are methods for the manufacture of the compositions. Also provided is their use in treating disease. Also provided is their use in preparing a medicament for treating a subject against disease, particularly against diseases described below. Also provided is their use in preparing a medicament for preventing or reducing disease in a subject.

Further provided is their use in preparing a medicament for treating a feline against infection caused by feline leukemia virus, for treating an avian against avian coccidiosis, for treating a bovine against diseases caused by *Escherichia coli*, for treating a bovine against diseases caused by bovine viral diarrhea virus, for treating a swine against diseases caused by *Mycoplasma hyopneumonia*, for treating a feline against diseases caused by feline influenza virus, a subject against cancer, for treating a canine against diseases caused by canine coronavirus, for treating a bovine against diseases caused by bovine rotavirus, and for treating a canine for diseases caused by canine influenza virus. Also provided is the use of adjuvants as a marker vaccine to aid in the identification of animals that have been vaccinated. Also provided is the use of CpG to enhance the effects of the adjuvants.

The first aspect of the present invention provides: An immunogenic composition comprising an adjuvant formulation and an immunologically effective amount of an antigen component, wherein the adjuvant formulation comprises a saponin, a sterol, a quaternary ammonium compound, and a polymer.

The second aspect of the present invention provides: An immunogenic composition as above, wherein the saponin is present in an amount of about 1 µg to about 5,000 µg per dose, the sterol is present in an amount of about 1 µg to about 5,000 µg per dose, the quaternary ammonium compound is present in an amount of about 1 µg to about 5,000 µg per dose, and the polymer is present in an amount of about 0.0001% volume to volume (v/v) to about 75% v/v.

The third aspect of the present invention provides: An immunogenic composition as above, wherein the saponin is Quil A or a purified fraction thereof, the sterol is cholesterol, the quaternary ammonium compound is dimethyl dioctadecyl ammonium bromide (DDA), and the polymer is polyacrylic acid.

The fourth aspect of the present invention provides: An immunogenic composition as above, further comprising a Th2 stimulant.

The fifth aspect of the present invention provides: An immunogenic composition as above, wherein the Th2 stimulant is a glycolipid.

The sixth aspect of the present invention provides: An immunogenic composition as above, wherein the Th2 stimulant is N-(2-deoxy-2-L-leucylamino-β-D-glucopyranosyl)-N-octadecyldodecanamide acetate.

The seventh aspect of the present invention provides: An immunogenic composition as above, wherein the glycolipid is present in an amount of about 0.01 mg to about 10 mg per dose.

The eighth aspect of the present invention provides: An immunogenic composition as above, wherein said antigen component comprises an inactivated virus.

The ninth aspect of the present invention provides: A method of preparing an immunogenic composition as above comprising:
 a) preparing a composition of the antigen component in a buffer;
 b) adding the saponin to the composition of step a;
 c) adding the sterol to the composition of step b;
 d) adding the quaternary ammonium compound to the composition of step c;
 e) adding the polymer to the composition of step d.

The tenth aspect of the present invention provides: A method as above of preparing an immunogenic composition, wherein the saponin is Quil A or a purified fraction thereof, the sterol is cholesterol, the quaternary ammonium compound is DDA, and the polymer is polyacrylic acid.

The eleventh aspect of the present invention provides: A method as above of preparing an immunogenic composition, further comprising a step of homogenizing the composition of step a and continuing the homogenization during each of steps a to d.

The twelfth aspect of the present invention provides: A method as above of preparing an immunogenic composition, further comprising a step comprising microfluidizing the composition of step d.

The thirteenth aspect of the present invention provides: A method as above of preparing an immunogenic composition, further comprising a step f) of adding to the composition of step e, a Th2 stimulant.

The fourteenth aspect of the present invention provides: A method of preparing an immunogenic composition according to the thirteenth aspect, wherein the Th2 stimulant is a glycolipid.

The fifteenth aspect of the present invention provides: A method of preparing an immunogenic composition according to the thirteenth aspect, wherein the Th2 stimulant is N-(2-deoxy-2-L-leucylamino-β-D-glucopyranosyl)-N-octadecyldodecanamide acetate.

The sixteenth aspect of the present invention provides: A vaccine composition comprising an adjuvant formulation and a therapeutically effective amount of an antigen component, wherein the adjuvant formulation comprises a saponin, a sterol, a quaternary ammonium compound, and a polymer, and wherein said antigen component comprises an inactivated virus.

The seventeenth aspect of the present invention provides: A method of preparing a vaccine composition, comprising:
 a) preparing a composition of the antigen component in a buffer;
 b) adding the saponin to the composition of step a;
 c) adding the sterol to the composition of step b;

d) adding the quaternary ammonium compound to the composition of step c;

e) adding the polymer to the composition of step d.

The eighteenth aspect of the present invention provides: A method of preparing a vaccine composition according to the seventeenth aspect, wherein the saponin is Quil A or a purified fraction thereof, the sterol is cholesterol, the quaternary ammonium compound is DDA, and the polymer is polyacrylic acid.

The nineteenth aspect of the present invention provides: A method of preparing a vaccine composition according to the seventeenth aspect, further comprising a step of homogenizing the composition of step a and continuing the homogenization during each of steps a to d.

The twentieth aspect of the present invention provides: A method of preparing a vaccine composition according to the seventeenth aspect, further comprising a step comprising microfluidizing the composition of step d.

The twenty-first aspect of the present invention provides: A method of preparing a vaccine composition according to the seventeenth aspect, further comprising a step f) of adding to the composition of step e, a Th2 stimulant.

The twenty-second aspect of the present invention provides: A method of preparing a vaccine composition according to the seventeenth aspect, further comprising a glycolipid.

The twenty-third aspect of the present invention provides: A method of preparing a vaccine composition according to the twenty-second aspect, wherein the glycolipid is N-(2-deoxy-2-L-leucylamino-β-D-glucopyranosyl)-N-octadecyl-dodecanamide acetate.

The twenty-fourth aspect of the present invention provides: An immunogenic composition according to the first to eighth aspects, further comprising an oil.

The twenty-fifth aspect of the present invention provides: An immunogenic composition according to the first to eighth aspects, wherein the antigen component comprises feline leukemia virus.

The twenty-sixth aspect of the present invention provides: A method of preparing an immunogenic composition according to the ninth to fifteenth aspects, wherein the antigen component comprises feline leukemia virus.

The twenty-seventh aspect of the present invention provides: A method of preparing a vaccine composition according to the seventeenth to twenty-third aspects, wherein the antigen component comprises feline leukemia virus.

The twenty-eighth aspect of the present invention provides: An immunogenic composition according to the first to eighth aspects, wherein the antigen component comprises an *Escherichia coli* J-5 strain bacterin.

The twenty-ninth aspect of the present invention provides: The immunogenic composition of the $24^{th}$ aspect, wherein the antigen component comprises an *Escherichia coli* J-5 strain bacterin.

The thirtieth aspect of the present invention provides: An immunogenic composition comprising an adjuvant formulation and an immunologically effective amount of an *Escherichia coli* J-5 strain bacterin, wherein the adjuvant formulation comprises a saponin, a sterol, a quaternary ammonium compound, and an oil.

The thirty-first aspect of the present invention provides: A method of preparing an immunogenic composition according to the ninth to fifteenth aspects, wherein the antigen component comprises an *Escherichia coli* J-5 strain bacterin.

The thirty-second aspect of the present invention provides: A method of preparing a vaccine composition according to the seventeenth to twenty-third aspects, wherein the antigen component comprises an *Escherichia coli* J-5 strain bacterin.

The thirty-third aspect of the present invention provides: A vaccine composition comprising an adjuvant formulation and an immunologically effective amount of an *Escherichia coli* J-5 strain bacterin, wherein the adjuvant formulation comprises a saponin, a sterol, a quaternary ammonium compound, and an oil.

The thirty-fourth aspect of the present invention provides: A method of treating a bovine against infection caused by *Escherichia coli* comprising administering to the bovine the vaccine composition of the thirty-third aspect.

The thirty-fifth aspect of the present invention provides: An immunogenic composition according to the first to eighth aspects, wherein the antigen component comprises bovine viral diarrhea virus (BVDV).

The thirty-sixth aspect of the present invention provides: The immunogenic composition of the thirty-fourth aspect, wherein the antigen component comprises BVDV type 1 (BVDV-1) and BVDV type 2 (BVDV-2).

The thirty-seventh aspect of the present invention provides: A method of preparing an immunogenic composition according to the ninth to fifteenth aspects, wherein the antigen component comprises BVDV.

The thirty-eighth aspect of the present invention provides: The method of the thirty-seventh aspect, wherein the antigen component comprises BVDV-1 and BVDV-2.

The thirty-ninth aspect of the present invention provides: A method of preparing a vaccine composition according to the seventeenth to twenty-third aspects, wherein the antigen component comprises BVDV.

The fortieth aspect of the present invention provides: The method of the thirty-ninth aspect, wherein the antigen component comprises BVDV-1 and BVDV-2.

The forty-first aspect of the present invention provides: A vaccine composition comprising an adjuvant formulation and a therapeutically effective amount of an antigen component, wherein the adjuvant formulation comprises a saponin, a sterol, a quaternary ammonium compound, and a polymer, and wherein the antigen component comprises BVDV-1 and BVDV-2.

The forty-second aspect of the present invention provides: A method of treating a bovine against infection caused by BVDV comprising administering to the bovine the vaccine composition of the forty-first aspect.

The forty-third aspect of the present invention provides: An immunogenic composition according to the first to eighth aspects, wherein the antigen component comprises *Mycoplasma hyopneumonia* (*M. hyopneumonia*).

The forty-fourth aspect of the present invention provides: A method of preparing an immunogenic composition according to the ninth to fifteenth aspects, wherein the antigen component comprises *M. hyopneumonia*.

The forty-fifth aspect of the present invention provides: A method of preparing a vaccine composition according to the seventeenth to twenty-third aspects, wherein the antigen component comprises *M. hyopneumonia*.

The forty-sixth aspect of the present invention provides: An immunogenic composition according to the first to eighth aspects, wherein the antigen component comprises feline influenza virus (FIV).

The forty-seventh aspect of the present invention provides: A method of preparing an immunogenic composition according to the ninth to fifteenth aspects, wherein the antigen component comprises FIV.

The forty-eighth aspect of the present invention provides: A method of preparing a vaccine composition according to the seventeenth to twenty-third aspects, wherein the antigen component comprises FIV.

The forty-ninth aspect of the present invention provides: An immunogenic composition according to the first to eighth aspects, wherein the antigen component comprises a cancer antigen.

The fiftieth aspect of the present invention provides: A method of preparing an immunogenic composition according to the ninth to fifteenth aspects, wherein the antigen component comprises a cancer antigen.

The fifty-first aspect of the present invention provides: A method of preparing a vaccine composition according to the seventeenth to twenty-third aspects, wherein the antigen component comprises a cancer antigen.

The fifty-second aspect of the present invention provides: An immunogenic composition according to the first to eighth aspects, further comprising an ORN/ODN.

The fifty-third aspect of the present invention provides: An immunogenic composition according to the fifty-second aspect, wherein the ORN/ODN is CpG.

The fifty-fourth aspect of the present invention provides: A method of preparing an immunogenic composition according to the ninth to fifteenth aspects, further comprising a step of adding an ORN/ODN to the composition of step a.

The fifty-fifth aspect of the present invention provides: A method of preparing a vaccine composition according to the seventeenth to twenty-third aspects, further comprising a step of adding an ORN/ODN to the composition of step a.

The fifty-sixth aspect of the present invention provides: A method of preparing a vaccine composition according to the fifty-fifth aspect, wherein the ORN/ODN is CpG.

The fifty-seventh aspect of the present invention provides: An immunogenic composition according to the first to eighth aspects, wherein the antigen component comprises canine coronavirus (CCV).

The fifty-eighth aspect of the present invention provides: A method of preparing an immunogenic composition according to the ninth to fifteenth aspects, wherein the antigen component comprises CCV.

The fifty-ninth aspect of the present invention provides: A method of preparing a vaccine composition according to the seventeenth to twenty-third aspects, wherein the antigen component comprises CCV.

The sixtieth aspect of the present invention provides: An immunogenic composition according to the first to eighth aspects, wherein the antigen comprises bovine rotavirus.

The sixty-first aspect of the present invention provides: A method of preparing an immunogenic composition according to the ninth to fifteenth aspects, wherein the antigen component comprises bovine rotavirus.

The sixty-second aspect of the present invention provides: A method of preparing a vaccine composition according to the seventeenth to twenty-third aspects, wherein the antigen component comprises bovine rotavirus.

The sixty-third aspect of the present invention provides: An immunogenic composition according to the first to eighth aspects, wherein the antigen component comprises canine influenza virus (CIV).

The sixty-fourth aspect of the present invention provides: A method of preparing an immunogenic composition according to the ninth to fifteenth aspects, wherein the antigen component comprises CIV.

The sixty-fifth aspect of the present invention provides: A method of preparing a vaccine composition according to the seventeenth to twenty-third aspects, wherein the antigen component comprises CIV.

The sixty-sixth aspect of the present invention provides: A method of differentiating an animal naturally infected with BVDV from an animal vaccinated with the vaccine composition of the forty-first aspect, said method comprising obtaining a sample from a test animal, and measuring the levels of E2 protein and NS2/3 proteins in said sample, wherein the absence of NS2/3 proteins indicates that the animal was vaccinated with said vaccine composition.

BRIEF DESCRIPTION OF THE FIGURE

FIG. 1 depicts a gel run by radioimmunoprecipitation assay showing the antibody profile differences between NS2/3 proteins and E2 proteins of the BVD Virus. The PreZent A treated group shows an antibody response to both the NS2/3 proteins and the E2 proteins while the QCDC and QCDCR treated groups demonstrated an antibody response to only E2 protein and not the NS2/3 proteins.

DETAILED DESCRIPTION OF THE INVENTION

Definitions

"About" or "approximately," when used in connection with a measurable numerical variable, refers to the indicated value of the variable and to all values of the variable that are within the experimental error of the indicated value (e.g., within the 95% confidence interval for the mean) or within 10 percent of the indicated value, whichever is greater, unless about is used in reference to time intervals in weeks where "about 3 weeks," is 17 to 25 days, and about 2 to about 4 weeks is 10 to 40 days.

"Adjuvant" means any substance that increases the humoral or cellular immune response to an antigen. Adjuvants are generally used to accomplish two objectives: The slow release of antigens from the injection site, and the stimulation of the immune system.

"Alkyl" refers to both straight and branched saturated hydrocarbon moieties.

"Amine" refers to a chemical compound containing nitrogen. Amines are a group of compounds derived from ammonia by substituting hydrocarbon groups for the hydrogen atoms. "Quaternary amine" refers to an ammonium based compound with four hydrocarbon groups.

"Antibody" refers to an immunoglobulin molecule that can bind to a specific antigen as the result of an immune response to that antigen. Immunoglobulins are serum proteins composed of "light" and "heavy" polypeptide chains having "constant" and "variable" regions and are divided into classes (e.g., IgA, IgD, IgE, IgG, and IgM) based on the composition of the constant regions.

"Antigen" or "immunogen" refers to any substance that stimulates an immune response. The term includes killed, inactivated, attenuated, or modified live bacteria, viruses, or parasites. The term antigen also includes polynucleotides, polypeptides, recombinant proteins, synthetic peptides, protein extract, cells (including tumor cells), tissues, polysaccharides, or lipids, or fragments thereof, individually or in any combination thereof. The term antigen also includes antibodies, such as anti-idiotype antibodies or fragments thereof, and to synthetic peptide mimotopes that can mimic an antigen or antigenic determinant (epitope).

"Bacterin" means a suspension of one or more killed bacteria which may be used as a component of a vaccine or immunogenic composition.

"Buffer" means a chemical system that prevents change in the concentration of another chemical substance, e.g., proton donor and acceptor systems serve as buffers preventing marked changes in hydrogen ion concentration (pH). A further example of a buffer is a solution containing a mixture of a weak acid and its salt (conjugate base) or a weak base and its salt (conjugate acid).

"Cellular immune response" or "cell mediated immune response" is one mediated by T-lymphocytes or other white blood cells or both, and includes the production of cytokines, chemokines and similar molecules produced by activated T-cells, white blood cells, or both.

"Cholesterol" refers to a white crystalline substance with a chemical formula of $C_{27}H_{45}OH$. It is a cyclic hydrocarbon alcohol, which is classified as a lipid. It is insoluble in water but soluble in a number of organic solvents.

"Delayed type hypersensitivity (DTH)" refers to an inflammatory response that develops 24 to 72 hours after exposure to an antigen that the immune system recognizes as foreign. This type of immune response involves mainly T cells rather than antibodies (which are made by B cells).

"Dose" refers to a vaccine or immunogenic composition given to a subject. A "first dose" or "priming vaccine" refers to the dose of such a composition given on Day 0. A "second dose" or a "third dose" or an "annual dose" refers to an amount of such composition given subsequent to the first dose, which may or may not be the same vaccine or immunogenic composition as the first dose.

"Emulsifier" means a substance used to make an emulsion more stable.

"Emulsion" means a composition of two immiscible liquids in which small droplets of one liquid are suspended in a continuous phase of the other liquid.

"Esters" refers to any of a class of organic compounds corresponding to the inorganic salts, which are formed from a condensation reaction in which a molecule of an organic acid unites with a molecule of alcohol with elimination of a molecule of water.

"Excipient" refers to any component of a vaccine that is not an antigen.

"Homogenization" refers to a process of mixing one or more components, either similar or dissimilar, into a uniform mixture.

"Humoral immune response" refers to one that is mediated by antibodies.

"Hydrophobic" means insoluble in water, not readily absorbing moisture, or being adversely affected by water; either incompatible with water or having little affinity for it.

"Immune response" in a subject refers to the development of a humoral immune response, a cellular immune response, or a humoral and a cellular immune response to an antigen. Immune responses can usually be determined using standard immunoassays and neutralization assays, which are known in the art.

"Immunologically protective amount" or "immunologically effective amount" or "effective amount to produce an immune response" of an antigen is an amount effective to induce an immunogenic response in the recipient. The immunogenic response may be sufficient for diagnostic purposes or other testing, or may be adequate to prevent signs or symptoms of disease, including adverse health effects or complications thereof, caused by infection with a disease agent. Either humoral immunity or cell-mediated immunity or both may be induced. The immunogenic response of an animal to an immunogenic composition may be evaluated, e.g., indirectly through measurement of antibody titers, lymphocyte proliferation assays, or directly through monitoring signs and symptoms after challenge with wild type strain, whereas the protective immunity conferred by a vaccine can be evaluated by measuring, e.g., reduction in clinical signs such as mortality, morbidity, temperature number, overall physical condition, and overall health and performance of the subject. The immune response may comprise, without limitation, induction of cellular and/or humoral immunity.

"Immunogenic" means evoking an immune or antigenic response. Thus an immunogenic composition would be any composition that induces an immune response.

"Immunostimulating complex" or ISCOM refers to a specific structure that is formed when Quil A is combined with cholesterol and phospholipids.

"Immunostimulatory molecule" refers to a molecule that generates an immune response.

"Lipids" refers to any of a group of organic compounds, including the fats, oils, waxes, sterols, and triglycerides, that are insoluble in water but soluble in nonpolar organic solvents, are oily to the touch, and together with carbohydrates and proteins constitute the principal structural material of living cells.

"Lipophilic" means showing a marked attraction to, or solubility in, lipids.

"Liposome" refers to a microscopic spherical particle formed by a lipid bilayer enclosing an aqueous compartment, used medicinally to carry a drug, antigen, vaccine, enzyme, or another substance to targeted cells in the body "Medicinal agent" refers to any agent which is useful in the prevention, cure, or improvement of disease, or the prevention of some physiological condition or occurrence.

"Parenteral administration" refers to the introduction of a substance, such as a vaccine, into a subject's body through or by way of a route that does not include the digestive tract. Parenteral administration includes subcutaneous, intramuscular, transcutaneous, intradermal, intraperitoneal, intraocular, and intravenous administration.

"Pharmaceutically acceptable" refers to substances, which are within the scope of sound medical judgment, suitable for use in contact with the tissues of subjects without undue toxicity, irritation, allergic response, and the like, commensurate with a reasonable benefit-to-risk ratio, and effective for their intended use.

"Reactogenicity" refers to the side effects elicited in a subject in response to the administration of an adjuvant, an immunogenic, or a vaccine composition. It can occur at the site of administration, and is usually assessed in terms of the development of a number of symptoms. These symptoms can include inflammation, redness, and abscess. It is also assessed in terms of occurrence, duration, and severity. A "low" reaction would, for example, involve swelling that is only detectable by palpitation and not by the eye, or would be of short duration. A more severe reaction would be, for example, one that is visible to the eye or is of longer duration.

"Room Temperature" means a temperature from 18 to 25° C.

"Saponin" refers to a group of surface-active glycosides of plant origin composed of a hydrophilic region (usually several sugar chains) in association with a hydrophobic region of either steroid or triterpenoid structure.

"Steroids" refers to any of a group of organic compounds belonging to biochemical class of lipids, which are easily soluble in organic solvents and slightly soluble in water.

Steroids comprise a four-fused ring system of three fused cyclohexane (six-carbon) rings plus a fourth cyclopentane (five-carbon) ring.

"Sterols" refers to compounds in animals which are biologically produced from terpenoid precursors. They comprise a steroid ring structure, having a hydroxyl (OH) group, usually attached to carbon-3. The hydrocarbon chain of the fatty-acid substituent varies in length, usually from 16 to 20 carbon atoms, and can be saturated or unsaturated. Sterols commonly contain one or more double bonds in the ring structure and also a variety of substituents attached to the rings. Sterols and their fatty-acid esters are essentially water insoluble.

"Subject" refers to any animal for which the administration of an adjuvant composition is desired. It includes mammals and non-mammals, including primates, livestock, companion animals, laboratory test animals, captive wild animals, ayes (including in ova), reptiles, and fish. Thus, this term includes but is not limited to monkeys, humans, swine; cattle, sheep, goats, equines, mice, rats, guinea pigs, hamsters, rabbits, felines, canines, chickens, turkeys, ducks, other poultry, frogs, and lizards.

"$TCID_{50}$" refers to "tissue culture infective dose" and is defined as that dilution of a virus required to infect 50% of a given batch of inoculated cell cultures. Various methods may be used to calculate $TCID_{50}$, including the Spearman-Karber method which is utilized throughout this specification. For a description of the Spearman-Karber method, see B. W. Mahy & H. O. Kangro, *Virology Methods Manual*, p. 25-46 (1996).

"Therapeutically effective amount" refers to an amount of an antigen or vaccine that would induce an immune response in a subject receiving the antigen or vaccine which is adequate to prevent or reduce signs or symptoms of disease, including adverse health effects or complications thereof, caused by infection with a pathogen, such as a virus or a bacterium. Humoral immunity or cell-mediated immunity or both humoral and cell-mediated immunity may be induced. The immunogenic response of an animal to a vaccine may be evaluated, e.g., indirectly through measurement of antibody titers, lymphocyte proliferation assays, or directly through monitoring signs and symptoms after challenge with wild type strain. The protective immunity conferred by a vaccine can be evaluated by measuring, e.g., reduction in clinical signs such as mortality, morbidity, temperature number, overall physical condition, and overall health and performance of the subject. The amount of a vaccine that is therapeutically effective may vary depending on the particular adjuvant used, the particular antigen used, or the condition of the subject, and can be determined by one skilled in the art.

"Treating" refers to preventing a disorder, condition, or disease to which such term applies, or to preventing or reducing one or more symptoms of such disorder, condition, or disease.

"Treatment" refers to the act of "treating" as defined above.

"Triterpeniods" refers to a large and diverse class of naturally occurring organic molecules, derived from six five-carbon isoprene (2-methyl-1,3-butadiene) units, which can be assembled and modified in thousands of ways. Most are multicyclic structures which differ from one another in functional groups and in their basic carbon skeletons. These molecules can be found in all classes of living things.

"Vaccine" refers to a composition that includes an antigen, as defined herein. Administration of the vaccine to a subject results in an immune response, generally against one or more specific diseases. The amount of a vaccine that is therapeutically effective may vary depending on the particular antigen used, or the condition of the subject, and can be determined by one skilled in the art.

Components of the Compositions

Triterpenoids and CpGs

Triterpenoids suitable for use in the adjuvant compositions can come from many sources, either plant derived or synthetic equivalents, including but not limited to, *Quillaja saponaria*, tomatine, ginsing extracts, mushrooms, and an alkaloid glycoside structurally similar to steroidal saponins. Thus, triterpenoids suitable for use in the adjuvant compositions include saponins, squalene, and lanosterol. The amount of triterpenoids suitable for use in the adjuvant compositions depends upon the nature of the triterpenoid used. However, they are generally used in an amount of about 1 µg to about 5,000 µg per dose. They also are used in an amount of about 1 µg to about 4,000 µg per dose, about 1 µg to about 3,000 µg per dose, about 1 µg to about 2,000 µg per dose, and about 1 µg to about 1,000 µg per dose. They are also used in an amount of about 5 µg to about 750 µg per dose, about 5 µg to about 500 µg per dose, about 5 µg to about 200 µg per dose, about 5 µg to about 100 µg per dose, about 15 µg to about 100 µg per dose, and in an amount of about 30 µg to about 75 µg per dose.

If a saponin is used, the adjuvant compositions generally contain an immunologically active saponin fraction from the bark of *Quillaja saponaria*. The saponin may be, for example, Quil A or another purified or partially purified saponin preparation, which can be obtained commercially. Thus, saponin extracts can be used as mixtures or purified individual components such as QS-7, QS-17, QS-18, and QS-21. In one embodiment the Quil A is at least 85% pure. In other embodiments, the Quil A is at least 90%, 91%, 92%, 93%, 94%, 95%, 96%, 97%, 98%, or 99% pure.

CpG ODNs are a recently described class of pharmacotherapeutic agents that are characterized by the presence of an unmethylated CG dinucleotide in specific base-sequence contexts (CpG motif). (Hansel T T, Barnes P J (eds): New Drugs for Asthma, Allergy and COPD. Prog Respir Res. Basel, Karger, 2001, vol 31, pp 229-232, which is incorporated herein by reference) These CpG motifs are not seen in eukaryotic DNA, in which CG dinucleotides are suppressed and, when present, usually methylated, but are present in bacterial DNA to which they confer immunostimulatory properties. These immunostimulatory properties include induction of a Th1-type response with prominent release of IFN-Á, IL-12, and IL-18. CpG ODNs (18-24 bp in length) possess immunomodulatory properties similar to bacterial DNA. The cell surface proteins can take up these molecules with variable results. However, with a carrier such as QCDC, QCDCR and other combinations cited within this patent the immunomodulation properties and uptake of the CpG are significantly enhanced.

The amount of CpG for use in the adjuvant compositions depends upon the nature of the CpG used and the intended species. However, they are generally used in an amount of about 1 µg to about 20 mg per dose. They also are used in an amount of about 1 µg to about 10 mg per dose, about 1 µg to about 5 mg per dose, about 1 µg to about 4 mg per dose, about 1 µg to about 3 mg per dose, about 1 µg to about 2 mg per dose, and about 1 µg to about 1 mg per dose. They are also used in an amount of about 5 µg to about 750 µg per dose, about 5 µg to about 500 µg per dose, about 5 µg to about 200 µg per dose, about 5 µg to about 100 µg per dose, 10 µg to about 100 µg per dose, about 15 µg to about 100 µg per dose, and in an amount of about 30 µg to about 75 µg per dose.

Sterols

Sterols suitable for use in the adjuvant compositions include β-sitosterol, stigmasterol, ergosterol, ergocalciferol, and cholesterol. These sterols are well known in the art and can be purchased commercially. For example cholesterol is disclosed in the Merck Index, 12th Ed., p. 369. The amount of sterols suitable for use in the adjuvant compositions depends upon the nature of the sterol used. However, they are generally used in an amount of about 1 µg to about 5,000 µg per dose. They also are used in an amount of about 1 µg to about 4,000 µg per dose, about 1 µg to about 3,000 µg per dose, about 1 µg to about 2,000 µg per dose, and about 1 µg to about 1,000 µg per dose. They are also used in an amount of about 5 µg to about 750 µg per dose, about 5 µg to about 500 µg per dose, about 5 µg to about 200 µg per dose, about 5 µg to about 100 µg per dose, about 15 µg to about 100 µg per dose, and about 30 µg to about 75 µg per dose.

Immunomodulators

The adjuvant compositions can further include one or more immunomodulatory agents such as, e.g., quaternary ammonium compounds (e.g., DDA), and interleukins, interferons, or other cytokines. These materials can be purchased commercially. The amount of an immunomodulator suitable for use in the adjuvant compositions depends upon the nature of the immunomodulator used and the subject. However, they are generally used in an amount of about 1 µg to about 5,000 µg per dose. They also are used in an amount of about 1 µg to about 4,000 µg per dose, about 1 µg to about 3,000 µg per dose, about 1 µg to about 2,000 µg per dose, and about 1 µg to about 1,000 µg per dose. They are also used in an amount of about 5 µg to about 750 µg per dose, about 5 µg to about 500 µg per dose, about 5 µg to about 200 µg per dose, about 5 µg to about 100 µg per dose, about 15 µg to about 100 µg per dose, and in an amount of about 30 µg to about 75 µg per dose. For a specific example, adjuvant compositions containing DDA can be prepared by simply mixing an antigen solution with a freshly prepared solution of DDA.

Polymers

The adjuvant compositions can further include one or more polymers such as, for example, DEAE Dextran, polyethylene glycol, and polyacrylic acid and polymethacrylic acid (eg, CARBOPOL®). Such material can be purchased commercially. The amount of polymers suitable for use in the adjuvant compositions depends upon the nature of the polymers used. However, they are generally used in an amount of about 0.0001% volume to volume (v/v) to about 75% v/v. In other embodiments, they are used in an amount of about 0.001% v/v to about 50% v/v, of about 0.005% v/v to about 25% v/v, of about 0.01% v/v to about 10% v/v, of about 0.05% v/v to about 2% v/v, and of about 0.1% v/v to about 0.75% v/v. In another embodiment, they are used in an amount of about 0.02 v/v to about 0.4% v/v. DEAE-dextran can have a molecular size in the range of 50,000 Da to 5,000,000 Da, or it can be in the range of 500,000 Da to 2,000,000 Da. Such material may be purchased commercially or prepared from dextran.

Another specific example is polyacrylic acid (e.g., the CARBOPOL® polymers), which has an average equivalent weight of 76. They are produced from primary polymer particles of about 0.2 to 6.0 microns in average diameter. The CARBOPOL® polymers swell in water up to 1000 times their original volume and ten times their original diameter to form a gel when exposed to a pH environment greater than the pKa of the carboxylate group. At a pH greater than the pKa of carboxylate group, the carboxylate groups ionize resulting in repulsion between the negative charges, which adds to the swelling of the polymer.

Th2 Stimulants

The adjuvant compositions can further include one or more Th2 stimulants such as, for example, Bay R1005® and aluminum. The amount of Th2 stimulants suitable for use in the adjuvant compositions depends upon the nature of the Th2 stimulant used. However, they are generally used in an amount of about 0.01 mg to about 10 mg per dose. In other embodiments, they are used in an amount of about 0.05 mg to about 7.5 mg per dose, of about 0.1 mg to about 5 mg per dose, of about 0.5 mg to about 2.5 mg per dose, and of 1 mg to about 2 mg per dose. A specific example is Bay R1005®, a glycolipid with the chemical name "N-(2-deoxy-2-L-leucylamino-β-D-glucopyranosyl)-N-octadecyldodecanamide acetate." It can be synthesized according to the procedure found in Lockhoff, O. (*Angew. Chem. Int. Ed. Engl.* 30:1611-1620; 1991). It is recommended that it is stored at 2-8° C. in an airtight container. Its chemical or physical properties are that it is slightly hygroscopic, does not form polymorphs, is chemically stable in air and light at temperatures up to 50° C. and in aqueous solvents at pH 2-12 at ambient temperature. It is an amphiphilic molecule which forms micelles in aqueous solution.

Antigens and Diseases

The adjuvant compositions can contain one or more antigens. The antigen can be any of a wide variety of substances capable of producing a desired immune response in a subject. Although Quil A alone is virucidal, Quil A is detoxified with the addition of cholesterol when forming helical micelles (see U.S. Pat. No. 7,122,191). The adjuvant compositions described herein have been found to be non-virucidal, and non-hemolytic or membranolytic. Thus, the antigens used with these adjuvant compositions can be one or more of viruses (inactivated, attenuated, and modified live), bacteria, parasites, nucleotides, polynucleotides, peptides, polypeptides, recombinant proteins, synthetic peptides, protein extract, cells (including tumor cells), tissues, polysaccharides, carbohydrates, fatty acids, teichioc acid, peptidoglycans, lipids, or glycolipids, individually or in any combination thereof.

The antigens used with the adjuvants of the invention also include immunogenic fragments of nucleotides, polynucleotides, peptides, polypeptides, that can be isolated from the organisms referred to herein.

Live, modified-live, and attenuated viral strains that do not cause disease in a subject have been isolated in non-virulent form or have been attenuated using methods well known in the art, including serial passage in a suitable cell line or exposure to ultraviolet light or a chemical mutagen. Inactivated or killed viral strains are those which have been inactivated by methods known to those skilled in the art, including treatment with formalin, betapropriolactone (BPL), binary ethyleneimine (BEI), sterilizing radiation, heat, or other such methods.

Two or more antigens can be combined to produce a polyvalent composition that can protect a subject against a wide variety of diseases caused by the pathogens. Currently, commercial manufacturers of vaccines, as well as end users, prefer polyvalent vaccine products. While conventional adjuvants are often limited in the variety of antigens with which they can be effectively used (either monovalently or polyvalently), the adjuvants described herein can be used effectively with a wide range of antigens, both monovalently and polyvalently. Thus, the antigens described herein can be combined in a single composition comprising the adjuvants described herein.

Some examples of bacteria which can be used as antigens with the adjuvant compositions include, but are not limited to, *Aceinetobacter calcoaceticus, Acetobacter paseruianus, Actinobacillus pleuro pneumoniae, Aeromonas hydrophila, Alicyclobacillus acidocaldarius, Arhaeglobus fulgidus, Bacillus pumilus, Bacillus stearothermophillus, Bacillus subtilis, Bacillus thermocatenulatus, Bordetella bronchiseptica, Burkholderia cepacia, Burkholderia glumae, Campylobacter coli, Campylobacter fetus, Campylobacter jejuni, Campylobacter hyointestinalis, Chlamydia psittaci, Chlamydia trachomatis, Chlamydophila* spp., *Chromobacterium viscosum, Erysipelothrix rhusiopathieae, Listeria monocytogenes, Ehrlichia canis, Escherichia coli, Haemophilus influenzae, Haemophilus somnus, Helicobacter suis, Lawsonia intracellularis, Legionella pneumophilia, Moraxellsa* sp., *Mycobactrium bovis, Mycoplasma hyopneumoniae, Mycoplasma mycoides* subsp. *mycoides* LC, *Clostridium perfringens, Odoribacter denticanis, Pasteurella (Mannheimia) haemolytica, Pasteurella multocida, Photorhabdus luminescens, Porphyromonas gulae, Porphyromonas gingivalis, Porphyromonas salivosa, Propionibacterium acnes, Proteus vulgaris, Pseudomnas wisconsinensis, Pseudomonas aeruginosa, Pseudomonas fluorescens* C9, *Pseudomonas fluorescens* SIKW1, *Pseudomonas fragi, Pseudomonas luteola, Pseudomonas oleovorans, Pseudomonas* sp B11-1, *Alcaliges eutrophus, Psychrobacter immobilis, Rickettsia prowazekii, Rickettsia rickettsia, Salmonella typhimurium, Salmonella bongori, Salmonella enterica, Salmonella dublin, Salmonella typhimurium, Salmonella choleraseuis, Salmonella newport, Serratia marcescens, Spirlina platensis, Staphlyoccocus aureus, Staphyloccocus epidermidis, Staphylococcus hyicus, Streptomyces albus, Streptomyces cinnamoneus, Streptococcus suis, Streptomyces exfoliates, Streptomyces scabies, Sulfolobus acidocaldarius, Syechocystis* sp., *Vibrio cholerae, Borrelia burgdorferi, Treponema denticola, Treponema minutum, Treponema phagedenis, Treponema refringens, Treponema vincentii, Treponema palladium,* and *Leptospira* species, such as the known pathogens *Leptospira canicola, Leptospira grippotyposa, Leptospira hardjo, Leptospira borgpetersenii hardjo-bovis, Leptospira borgpetersenii hardjo-prajitno, Leptospira interrogans, Leptospira icterohaemorrhagiae, Leptospira pomona,* and *Leptospira bratislava*, and combinations thereof.

Both inactivated viruses and attenuated live viruses may be used in the adjuvant compositions. Some examples of viruses which can be used as antigens include, but are not limited to, Avian herpesviruses, Bovine herpesviruses, Canine herpesviruses, Equine herpesviruses, Feline viral rhinotracheitis virus, Marek's disease virus, Ovine herpesviruses, Porcine herpesviruses, Pseudorabies virus, Avian paramyxoviruses, Bovine respiratory syncytial virus, Canine distemper virus, Canine parainfluenza virus, canine adenovirus, canine parvovirus, Bovine Parainfluenza virus 3, Ovine parainfluenza 3, Rinderpest virus, Border disease virus, Bovine viral diarrhea virus (BVDV), BVDV Type I, BVDV Type II, Classical swine fever virus, Avian Leukosis virus, Bovine immunodeficiency virus, Bovine leukemia virus, Bovine tuberculosis, Equine infectious anemia virus, Feline immunodeficiency virus, Feline leukemia virus (FeLV), Newcastle Disease virus, Ovine progressive pneumonia virus, Ovine pulmonary adenocarcinoma virus, Canine coronavirus (CCV), pantropic CCV, Canine respiratory coronavirus, Bovine coronavirus, Feline Calicivirus, Feline enteric coronavirus, Feline infectious peritonitis, virus, Porcine epidemic diarrhea virus, Porcine hemagglutinating encephalomyletitis virus, Porcine parvovirus, Porcine Circovirus (PCV) Type I, PCV Type II, Porcine Reproductive and Respiratory Syndrome (PRRS) Virus, Transmissible gastroenteritis virus, Turkey coronavirus, Bovine ephemeral fever virus, Rabies, Rotovirus, Vesicular stomatitis virus, lentivirus, Avian influenza, Rhinoviruses, Equine influenza virus, Swine influenza virus, Canine influenza virus, Feline influenza virus, Human influenza virus, Eastern Equine encephalitis virus (EEE), Venezuelan equine encephalitis virus, West Nile virus, Western equine encephalitis virus, human immunodeficiency virus, human papilloma virus, varicella zoster virus, hepatitis B virus, rhinovirus, and measles virus, and combinations thereof.

Examples of peptide antigens include *Bordetella bronchiseptica* p68, GnRH, IgE peptides, Fel d1, and cancer antigens, and combinations thereof. Examples of other antigens include nucleotides, carbohydrates, lipids, glycolipids, peptides, fatty acids, and teichioc acid, and peptidoglycans, and combinations thereof.

Some examples of parasites which can be used as antigens with the adjuvant compositions include, but are not limited to, *Anaplasma, Fasciola hepatica* (liver fluke), *Coccidia, Eimeria* spp., *Neospora caninum, Toxoplasma gondii, Giardia, Dirofilaria* (heartworms), *Ancylostoma* (hookworms), *Trypanosoma* spp., *Leishmania* spp., *Trichomonas* spp., *Cryptosporidium parvum, Babesia, Schistosoma, Taenia, Strongyloides, Ascaris, Trichinella, Sarcocystis, Hammondia,* and *Isopsora*, and combinations thereof. Also contemplated are external parasites including, but not limited to, ticks, including *Ixodes, Rhipicephalus, Dermacentor, Amblyomma, Boophilus, Hyalomma,* and *Haemaphysalis* species, and combinations thereof.

The amount of antigen used to induce an immune response will vary considerably depending on the antigen used, the subject, and the level of response desired, and can be determined by one skilled in the art. For vaccines containing modified live viruses or attenuated viruses, a therapeutically effective amount of the antigen generally ranges from about $10^2$ Tissue Culture Infective Dose (TCID)$_{50}$ to about $10^{10}$ TCID$_{50}$, inclusive. For many such viruses, a therapeutically effective dose is generally in the range of about $10^2$ TCID$_{50}$ to about $10^8$ TCID$_{50}$, inclusive. In some embodiments, the ranges of therapeutically effective doses are about $10^3$ TCID$_{50}$ to about $10^6$ TCID$_{50}$, inclusive. In some other embodiments, the ranges of therapeutically effective doses are about $10^4$ TCID$_{50}$ to about $10^5$ TCID$_{50}$, inclusive.

For vaccines containing inactivated viruses, a therapeutically effective amount of the antigen is generally at least about 100 relative units per dose, and often in the range from about 1,000 to about 4,500 relative units per dose, inclusive. In other embodiments, the therapeutically effective amount of the antigen is in a range from about 250 to about 4,000 relative units per dose, inclusive, from about 500 to about 3,000 relative units per dose, inclusive, from about 750 to about 2,000 relative units per dose, inclusive, or from about 1,000 to about 1,500 relative units per dose, inclusive.

A therapeutically effective amount of antigen in vaccines containing inactivated viruses can also be measured in terms of Relative Potency (RP) per mL. A therapeutically effective amount is often in the range from about 0.1 to about 50 RP per mL, inclusive. In other embodiments, the therapeutically effective amount of the antigen is in a range from about 0.5 to about 30 RP per mL, inclusive, from about 1 to about 25 RP per mL, inclusive, from about 2 to about 20 RP per mL, inclusive, from about 3 to about 15 RP per mL, inclusive, or from about 5 to about 10 RP per mL, inclusive.

In one embodiment a FeLV antigen was produced from the FL74-UCD-1 cell line (ATCC Number CRL-8012) which is persistently infected with the KT-FeLV-UCD-1 feline leukemia virus strain. The amount of FeLV antigen in a vaccine can be measured as the amount of gp70 viral protein per mL. A therapeutically effective amount of FeLV antigen, when measured by the amount of gp70 viral protein per mL, generally is in the range from about 100 to about 350,000 ng/ml, inclusive. In another embodiment the range is from about 1,000 to about 300,000 ng/ml, inclusive, or from about 2,500 to about 250,000 ng/ml, inclusive, or from about 4,000 to about 220,000 ng/ml, inclusive, or from about 5,000 to about 150,000 ng/ml, inclusive, or from about 10,000 ng/ml to about 100,000 ng/ml, inclusive.

The number of cells for a bacterial antigen administered in a vaccine ranges from about $1 \times 10^6$ to about $5 \times 10^{19}$ colony forming units (CFU) per dose, inclusive. In other embodiments, the number of cells ranges from about $1 \times 10^7$ to $5 \times 10^{19}$ CFU/dose, inclusive, or from about $1 \times 10^8$ to $5 \times 10^{19}$ CFU/dose, inclusive. In still other embodiments, the number of cells ranges from about $1 \times 10^2$ to $5 \times 10^{19}$ CFU/dose, inclusive, or from about $1 \times 10^4$ to $5 \times 10^9$ CFU/dose, inclusive, or from about $1 \times 10^5$ to $5 \times 10^9$ CFU/dose, inclusive, or from about $1 \times 10^6$ to $5 \times 10^9$ CFU/dose, inclusive, or from about $1 \times 10^6$ to $5 \times 10^8$ CFU/dose, inclusive, or from about $1 \times 10^7$ to $5 \times 10^9$ CFU/dose, inclusive.

The number of cells for a parasite antigen administered in a vaccine ranges from about $1 \times 10^2$ to about $1 \times 10^{19}$ per dose, inclusive. In other embodiments, the number of cells ranges from about $1 \times 10^3$ to about $1 \times 10^9$ per dose, inclusive, or from about $1 \times 10^4$ to about $1 \times 10^8$ per dose, inclusive, or from about $1 \times 10^5$ to about $1 \times 10^7$ per dose, inclusive, or from about $1 \times 10^6$ to about $1 \times 10^8$ per dose, inclusive.

It is well known in the art that with conventional adjuvants, a substantially greater amount of inactivated viruses than modified live or attenuated viruses is needed to stimulate a comparable level of serological response. However, it has been surprisingly found that with the adjuvant compositions described herein, approximately the same amounts of inactivated virus and modified live virus stimulate similar levels of serological response. In addition, smaller amounts of modified live, attenuated, and inactivated virus are needed with the adjuvants described herein when compared with conventional adjuvants to achieve the same level of serological response. These unexpected findings demonstrate conservation of resources and reduction of cost during preparation of immunogenic and vaccine compositions. For vaccines with wide utility, the manufacture of millions of doses per year is required, so these savings can be substantial.

Excipients

Aqueous adjuvants provide certain advantages. They are generally easy to formulate and administer, and can induce few or less serious injection site reactions. However, aqueous adjuvants with an antigen tend to diffuse from the injection site, are cleared by the subject's liver, and generate an undesirable non-specific immune response. It has been surprisingly found that the aqueous adjuvant compositions described herein remain at the injection site until biometabolized, which occurs over a long period of time, and provide a targeted immune response.

Oil, when added as a component of an adjuvant, generally provides a long and slow release profile. In the present invention, the oil can be metabolizable or non-metabolizable. The oil can be in the form of an oil-in-water, a water-in-oil, or a water-in-oil-in-water emulsion.

Oils suitable for use in the present invention include alkanes, alkenes, alkynes, and their corresponding acids and alcohols, the ethers and esters thereof, and mixtures thereof. The individual compounds of the oil are light hydrocarbon compounds, i.e., such components have 6 to 30 carbon atoms. The oil can be synthetically prepared or purified from petroleum products. The moiety may have a straight or branched chain structure. It may be fully saturated or have one or more double or triple bonds. Some non-metabolizable oils for use in the present invention include mineral oil, paraffin oil, and cycloparaffins, for example.

The term oil is also intended to include "light mineral oil," i.e., oil which is similarly obtained by distillation of petrolatum, but which has a slightly lower specific gravity than white mineral oil.

Metabolizable oils include metabolizable, non-toxic oils. The oil can be any vegetable oil, fish oil, animal oil or synthetically prepared oil which can be metabolized by the body of the subject to which the adjuvant will be administered and which is not toxic to the subject. Sources for vegetable oils include nuts, seeds and grains.

An oil-in-water emulsion provided by the present invention is composed of an AMPHIGEN® formulation. This formulation comprises an aqueous component, lecithin, mineral oil, and surfactants. Patents describing the components of the formulation include U.S. Pat. Nos. 5,084,269 and 6,572,861.

Typically, the oil component of the present invention is present in an amount from 1% to 50% by volume; or in an amount of 10% to 45%; or in an amount from 20% to 40%.

Other components of the compositions can include pharmaceutically acceptable excipients, such as carriers, solvents, and diluents, isotonic agents, buffering agents, stabilizers, preservatives, vaso-constrictive agents, antibacterial agents, antifungal agents, and the like. Typical carriers, solvents, and diluents include water, saline, dextrose, ethanol, glycerol, oil, and the like. Representative isotonic agents include sodium chloride, dextrose, mannitol, sorbitol, lactose, and the like. Useful stabilizers include gelatin, albumin, and the like.

Surfactants are used to assist in the stabilization of the emulsion selected to act as the carrier for the adjuvant and antigen. Surfactants suitable for use in the present inventions include natural biologically compatible surfactants and non-natural synthetic surfactants. Biologically compatible surfactants include phospholipid compounds or a mixture of phospholipids. Preferred phospholipids are phosphatidylcholines (lecithin), such as soy or egg lecithin. Lecithin can be obtained as a mixture of phosphatides and triglycerides by water-washing crude vegetable oils, and separating and drying the resulting hydrated gums. A refined product can be obtained by fractionating the mixture for acetone insoluble phospholipids and glycolipids remaining after removal of the triglycerides and vegetable oil by acetone washing. Alternatively, lecithin can be obtained from various commercial sources. Other suitable phospholipids include phosphatidylglycerol, phosphatidylinositol, phosphatidylserine, phosphatidic acid, cardiolipin, and phosphatidylethanolamine. The phospholipids may be isolated from natural sources or conventionally synthesized.

Non-natural, synthetic surfactants suitable for use in the present invention include sorbitan-based non-ionic surfactants, e.g. fatty-acid-substituted sorbitan surfactants (commercially available under the name SPAN® or ARLACEL®), fatty acid esters of polyethoxylated sorbitol (TWEEN®), polyethylene glycol esters of fatty acids from sources such as castor oil (EMULFOR®); polyethoxylated fatty acid (e.g., stearic acid available under the name SIMULSOL M-53®), polyethoxylated isooctylphenol/formaldehyde polymer (TYLOXAPOL®), polyoxyethylene fatty alcohol ethers (BRIJ®); polyoxyethylene nonphenyl ethers (TRITON® N), polyoxyethylene isooctylphenyl ethers (TRITON® X).

Generally speaking, the surfactant, or the combination of surfactants, if two or more surfactants are used, is present in the emulsion in an amount of 0.01% to 10% by volume, preferably, 0.1% to 6.0%, more preferably 0.2% to 5.0%.

As used herein, "a pharmaceutically-acceptable carrier" includes any and all solvents, dispersion media, coatings, adjuvants, stabilizing agents, diluents, preservatives, antibacterial and antifungal agents, isotonic agents, adsorption delaying agents, and the like. The carrier(s) must be "acceptable" in the sense of being compatible with the other components of the compositions and not deleterious to the subject. Typically, the carriers will be will be sterile and pyrogen-free, and selected based on the mode of administration to be used. It is well known by those skilled in the art that the preferred formulations for the pharmaceutically acceptable carrier which comprise the compositions are those pharmaceutical carriers approved in the applicable regulations promulgated by the United States (US) Department of Agriculture or US Food and Drug Administration, or equivalent government agency in a non-US country. Therefore, the pharmaceutically accepted carrier for commercial production of the compositions is a carrier that is already approved or will be approved by the appropriate government agency in the US or foreign country.

The compositions optionally can include compatible pharmaceutically acceptable (i.e., sterile or non-toxic) liquid, semisolid, or solid diluents that serve as pharmaceutical vehicles, excipients, or media. Diluents can include water, saline, dextrose, ethanol, glycerol, and the like. Isotonic agents can include sodium chloride, dextrose, mannitol, sorbitol, and lactose, among others. Stabilizers include albumin, among others.

The compositions can also contain antibiotics or preservatives, including, for example, gentamicin, merthiolate, or chlorocresol. The various classes of antibiotics or preservatives from which to select are well known to the skilled artisan.

Preparation of the Compositions
Preparation of Adjuvant Formulations

An ISCOM can be prepared by combining a saponin, a sterol, and a phospholipid. For example, an ISCOM can contain 5% to 10% by weight Quil A, 1% to 5% cholesterol and phospholipids, and the remainder protein. The ratio of saponin to sterol in the adjuvant formulations will typically be in the order of from 1:100 weight to weight (w/w) to 5:1 w/w. In some embodiments, excess sterol is present, wherein the ratio of saponin to sterol is at least 1:2 w/w, or 1:5 w/w. In other embodiments, the saponin is in excess in relation to the sterol, and a ratio of saponin to sterol of about 5:1 w/w is used. ISCOM and ISCOMATRIX are commercially available from Isconova AB (Sweden).

In some embodiments, CARBOPOL® is used in combination with DDA in an amount of at least 0.1 part by weight of CARBOPOL® per part by weight of DDA. In other embodiments, at least 0.5 part by weight of CARBOPOL® per part by weight of DDA is used. In still other embodiments, at least 1 part by weight of CARBOPOL® per part by weight of DDA is used. The combination of CARBOPOL® and DDA forms a complex whereby the DDA tertiary amine functional group immunofunctionalizes the carboxylic acid side groups on the polymer. This allows for specific immune cells to target the antigen and adjuvant simultaneously and co-deliver the antigen and adjuvant together at the optimal time and concentration to the said cells.

The adjuvants described herein will generally not require any specific carrier, and will be formulated in an aqueous or other pharmaceutically acceptable buffer. In some cases, the vaccines of the disclosed embodiments will be presented in a suitable vehicle, such as for example, additional liposomes, microspheres or encapsulated antigen particles. The antigen can be contained within the vesicle membrane or contained outside the vesicle membrane. Generally, soluble antigens are outside and hydrophobic or lipidated antigens are either contained inside or outside the membrane.

The adjuvant compositions can be made in various forms depending upon the route of administration, storage requirements, and the like. For example, they can be made in the form of sterile aqueous solutions or dispersions suitable for injectable use, or made in lyophilized forms using freeze-drying, vacuum-drying, or spray-drying techniques. Lyophilized compositions can be reconstituted prior to use in a stabilizing solution, e.g., saline or HEPES. Thus, the adjuvant compositions can be used as a solid, semi-solid, or liquid dosage form.

The adjuvants can be manufactured using techniques known in the art. For example, the saponin and cholesterol may be admixed in a suitable detergent, followed by a solvent extraction technique to form liposomes or ISCOMs. The saponin and cholesterol may also be combined to form helical micelles as described in U.S. Pat. No. 7,122,191.

Phosphate buffered saline (PBS) may be used as the aqueous buffer medium; the pH of the buffer may be neutral or slightly alkaline or slightly acidic. Accordingly, the pH can be in a range of pH 6 to 8. A pH of about 7.0 to about 7.3 is common. The strength of the buffer can be between 10 to 50 mM $PO_4$ and between 10 to 150 mM $PO_4$. In one example, 0.063% PBS is used. The pH can be adjusted using NaOH or HCl as needed. Typical concentrations include from 1N to 10N HCl and 1N to 10N NaOH.

The quantity of adjuvant used depends on the antigen with which it is used and the antigen dosage to be applied. It is also dependent on the intended species and the desired formulation. Usually the quantity is within the range conventionally used for adjuvants. For example, adjuvants typically comprises from about 1 μg to about 1000 μg, inclusive, of a 1-mL dose. Similarly, antibiotics typically comprise from about 1 μg to about 60 μg, inclusive, of a 1-mL dose.

The adjuvant formulations can be homogenized or microfluidized. The formulations are subjected to a primary blending process, typically by passage one or more times through one or more homogenizers. Any commercially available homogenizer can be used for this purpose, e.g., Ross emulsifier (Hauppauge, N.Y.), Gaulin homogenizer (Everett, Mass.), or Microfluidics (Newton, Mass.). In one embodiment, the formulations are homogenized for three minutes at 10,000 rpm. Microfluidization can be achieved by use of a commercial mirofluidizer, such as model number 11OY available from Microfluidics, (Newton, Mass.); Gaulin Model 30CD (Gaulin, Inc., Everett, Mass.); and Rainnie Minilab Type 8.30H (Miro Atomizer Food and Dairy, Inc., Hudson, Wis.). These microfluidizers operate by forcing fluids through small apertures under high pressure, such that two fluid streams interact at high velocities in an interaction chamber to form compositions with droplets of a submicron size. In one embodiment, the formulations are microfluidized by being passed through a 200 micron limiting dimension chamber at 10,000+/−500 psi.

The adjuvant compositions described herein can be both homogenized and microfluidized. In one embodiment, an antigen is added to an appropriate buffer. The solution is stirred, and a saponin is slowly added to the antigen solution. A sterol is then slowly added to the antigen/saponin solution, followed by the slow addition of a quaternary ammonium compound to the antigen/saponin/sterol solution. The resulting composition is homogenized, and then microfluidized. After microfluidization, a polymer is added to microfluidized composition. Depending on the components used, the order of these steps can be altered to optimize preparation of the compositions.

Preparation of Immunogenic and Vaccine Compositions

The adjuvant compositions described herein can be used in the manufacture of immunogenic and vaccine compositions. For vaccine or immunogenic compositions, each dose contains a therapeutically effective amount of an antigen or antigens which can vary depending on the age and general condition of the subject, the route of administration, the nature of the antigen, and other factors. The amounts and concentrations of the other components in the vaccine or immunogenic compositions may be adjusted to modify the physical and chemical properties of the composition, and can readily be determined by the skilled artisan. An advantageous feature of the adjuvant compositions is that they are entirely configurable depending on the desired characteristics of the composition. For example, if a greater Th1 response is desired, the amount of the Th1 stimulator can be increased. Likewise, if a greater Th2 response is desired, the amount of the Th2 stimulator can be increased. A balanced Th1/Th2 response can also be achieved. The immunogenic and vaccine compositions can also be homogenized or microfluidized as described above.

Administration and Use of the Compositions
Administration of the Compositions

Dose sizes of the compositions typically range from about 1 mL to about 5 mL, inclusive, depending on the subject and the antigen. For example, for a canine or feline, a dose of about 1 mL is typically used, while in cattle a dose of about 2-5 mL is typically used. However, these adjuvants also can be formulated in microdoses, wherein doses of about 100 µL can be used.

The routes of administration for the adjuvant compositions include parenteral, oral, oronasal, intranasal, intratracheal, topical, and in ova. Any suitable device may be used to administer the compositions, including syringes, droppers, needleless injection devices, patches, and the like. The route and device selected for use will depend on the composition of the adjuvant, the antigen, and the subject, and such are well known to the skilled artisan.

Use of the Compositions

One of the requirements for any vaccine adjuvant preparation for commercial use is to establish the stability of the adjuvant solution for long periods of storage. Provided herein are adjuvant formulations that are easy to manufacture and stable for at least 18 months. In one embodiment, the formulations are stable for about 18 months. In another embodiment, the formulations are stable for between about 18 to about 24 months. In another embodiment the formulations are stable for about 24 months. Accelerated testing procedures also indicate that the formulations described herein are stable.

An advantageous feature of the present adjuvant compositions is that they can be safely and effectively administered to a wide range of subjects. In the art, it is expected that combinations of adjuvants will demonstrate more reactogenicity than the individual components. However, the compositions described herein show decreased reactogenicity when compared to compositions in which any one or two of the components are used, while the adjuvant effect is maintained. It has also been surprisingly found that the adjuvant compositions described herein demonstrate safety improvements when compared with other adjuvant compositions.

The adjuvant compositions described herein are useful for producing a desired immune response in a subject. They are efficacious in multiple species. A suitable subject is any animal for which the administration of an adjuvant composition is desired. It includes mammals and non-mammals, including primates, livestock, companion animals, laboratory test animals, captive wild animals, ayes (including in ova), reptiles, and fish. Thus, this term includes but is not limited to monkeys, humans, swine; cattle, sheep, goats, equines, mice, rats, guinea pigs, hamsters, rabbits, felines, canines, chickens, turkeys, ducks, other poultry, frogs, and lizards.

The adjuvants described herein can be used to show serological differentiation between infected and vaccinated animals. Thus, they can be used in a marker vaccine in which the antigen in the vaccine elicits in the vaccinated animals a different antibody pattern from that of the wild-type virus. A marker vaccine is generally used in conjunction with a companion diagnostic test which measures the difference in antibody patterns and demonstrates which animals have been vaccinated and which animals are infected with the wild-type virus. Such technology is useful in the control and eradication of viruses from a subject population.

The following examples are presented as illustrative embodiments, but should not be taken as limiting the scope of the invention. Many changes, variations, modifications, and other uses and applications of this invention will be apparent to those skilled in the art.

EXAMPLES

Example 1

Quil A/Cholesterol (QC) Solutions

Quil A (Superfos) was dissolved in water and a 50 mg/ml stock solution was prepared. Cholesterol, (Fabri Chem. Inc.) was dissolved in ethanol and an 18 mg/ml stock solution was prepared. The cholesterol stock solution then was filtered using a 0.2-micron filter.

Range of Quil A and Cholesterol concentrations in the various formulations was as low as 1/1 ug/ml of Quil A to cholesterol to as high as 1000/1000 ug/mL. To prepare a Quil A/Cholesterol stock solution of 50/50 µg/mL, the Quil A stock solution was diluted with water to a concentration of 50 µg/mL. While stirring this solution, the cholesterol stock solution was slowly added to a final concentration of 50 µg/mL.

Example 2

DDA (D) Solutions

Dimethyl dioctadecyl ammonium bromide (DDA; Fluka Analytical), was dissolved in ethanol, and an 18 mg/ml stock solution was prepared. The DDA stock solution was filtered using a 0.2-micron filter.

Example 3

Quil A/Cholesterol/DDA (QCD) Solutions

A Quil A/Cholesterol stock solution was prepared as in Example 1 to the desired concentrations. A DDA stock solution as prepared in Example 2 and slowly added to the Quil A/cholesterol stock solution. The solutions were mixed to achieve the desired final concentrations. The pH of the solution was adjusted with NaOH or HCl as needed to reach the desired final pH, which generally was in a range of about 6.9 to about 7.5.

Example 4

CARBOPOL® (C) Solutions

CARBOPOL® (Noveon, Mexico) was dissolved in deionized water and a 1.5% stock solution was prepared. In another embodiment, CARBOPOL® was dissolved in deionized water and a 0.75% stock solution was prepared.

Example 5

DDA/CARBOPOL® (DC) Solutions

A DDA stock solution was prepared as in Example 2. A 0.75% CARBOPOL® stock solution was prepared as in Example 4. The solutions were mixed to achieve the desired final concentrations.

Example 6

Quil A/Cholesterol/DDA/CARBOPOLO (QCDC) Solutions

A Quil A/Cholesterol/DDA stock solution was prepared as in Example 3. A 0.75% CARBOPOL® stock solution was prepared as in Example 4. The CARBOPOL® stock solution was slowly added to the Quil A/Cholesterol/DDA stock solution to achieve the desired final concentration. The pH of the solution was adjusted with NaOH or HCl to reach the desired final pH, which generally was in a range of about 6.9 to about 7.5.

Example 7

Bay R1005® (R) Solutions

To prepare a Bay R1005® stock solution, the glycolipid N-(2-deoxy-2-L-leucylamino-β-D-glucopyranosyl)-N-octadecyldodecanoylamide was dissolved in ethanol (60% v/v). Tween 20 and glacial acetic acid were then added. In one example, 3.49 gm of N-(2-deoxy-2-L-leucylamino-β-D-glucopyranosyl)-N-octadecyldodecanoylamide was dissolved in 44.64 mL of ethanol/water (60% v/v). This was combined with 1.12 mL of Tween 20 and 0.68 mL of glacial acetic acid.

Example 8

Quil A/Cholesterol/DDA/CARBOPOL®/Bay R1005® (QCDCR) Solutions

A Quil A/Cholesterol/DDA/CARBOPOL® stock solution was prepared as in Example 6. A Bay R1005® stock solution was prepared as in Example 7. The Bay R1005® solution was slowly added to the Quil A/Cholesterol/DDA/CARBOPOL® solution to achieve the desired final concentration. The pH of the solution was adjusted with NaOH or HCl as needed to reach the desired final pH, which generally was in a range of about 6.9 to about 7.5.

Example 9

DEAE Dextran Solutions (X)

A DEAE Dextran (X) stock solution was prepared by dissolving 200 mg/ml of DEAE Dextran into water. The solution can be autoclaved for about 20 minutes at 120° Centigrade (C).

Example 10

Quil A/Cholesterol/DDA/DEAE Solutions (QCDX)

A Quil A/Cholesterol/DDA stock solution was prepared according to Example 3. A DEAE stock solution was prepared according to Example 9. The solutions were combined by adding them directly into a homogenizer. Mixing employs a flash blending method using a shear force of greater than 1,000 sec$^{-1}$. Mixing is done by feeding the aqueous solution directly into the oil phase containing the nonpolar adjuvants and antigen components and blending until a homogeneous stable mixture is achieved. Typically this can be a minimum of several minutes or longer depending on the desired particle size.

Example 11

Oil Compositions (O)

An Oil stock solution was prepared by combining Drakeol mineral oil with Tween 85 and Span 85, heating to approximately 55° C. and then cooling and sterile filtering. This mixture would thus comprise the oil phase base component for an oil based carrier. If Cholesterol and/or DDA were selected to be a collaborating immunomodulator for one of these compositions it would then also be added to this mixture prior to filtration, since they are soluble in the oil phase.

Example 12

Quil A/Cholesterol/DDA/DEAE/Oil Compositions (QCDXO)

A Quil A/Cholesterol/DDA/DEAE stock solution was prepared according to Example 10. An oil stock composition was prepared according to Example 11. The solutions were a combination of Quil-A, DEAE-Dextran and water to achieve the quantity at said concentrations. This aqueous phase was mixed by continuously stirring the reaction for several minutes or longer at room temperature or higher and then sterile filtered and stored for addition to the oil phase. The aqueous phase was slowly added into a continuously mixing oil phase.

Example 13

Preparation of Immunogenic Compositions or Vaccine Compositions

To prepare an immunogenic composition or vaccine composition comprising an antigen and one of the adjuvants described above, the desired antigen was added to an appropriate buffer. Then the components of the desired adjuvant were added as described above. The resulting solution was brought to final volume with the buffer.

Example 13a

Antigen, Quil A, Cholesterol, DDA, CARBOPOL®

To prepare an immunogenic composition or vaccine composition comprising an antigen, Quil A, cholesterol, DDA, and CARBOPOL®, the desired antigen was added to an appropriate buffer. A Quil A stock solution was prepared as in Example 1 and slowly added to the antigen solution. A cholesterol stock solution was prepared as in Example 1 and was slowly added to the antigen/Quil A solution. A DDA stock solution was prepared as in Example 2 and slowly added to the antigen/Quil A/cholesterol solution. The antigen/Quil A/cholesterol/DDA solution was homogenized and microfluidized. A 0.75% CARBOPOL® solution was prepared as in Example 4. After microfluidization, the CARBOPOL® solution (0.05% v/v) was added to microfluidized composition and pH was adjusted with NaOH or HCl to about 6.9 to about 7.5.

Example 13b

Antigen, Quil A, Cholesterol, DDA, CARBOPOL®, Bay R1005®

To prepare an immunogenic composition or vaccine composition comprising an antigen, Quil A, cholesterol, DDA, CARBOPOL®, and Bay R1005®, the desired antigen was added to an appropriate buffer. A Quil A stock solution was prepared as in Example 1 and slowly added to the antigen solution. A cholesterol stock solution was prepared as in Example 1 and was slowly added to the antigen/Quil A solution. A DDA stock solution was prepared as in Example 2 and slowly added to the antigen/Quil A/cholesterol solution. The antigen/Quil A/cholesterol/DDA solution was homogenized and microfluidized. A 0.75% CARBOPOL® solution was prepared as in Example 4. After microfluidization, the CARBOPOL® solution (0.05% v/v) was added to microfluidized composition and pH was adjusted with NaOH or HCl to about 6.9 to about 7.5. A Bay R1005® stock solution was prepared as in Example 7. The Bay R1005® component was added to the aqueous phase after the DDA was added.

Example 13c

Antigen, Quil A, Cholesterol, DDA, DEAE Dextran

To prepare an immunogenic composition or vaccine composition comprising an antigen, Quil A, cholesterol, DDA, and DEAE dextran, the desired antigen was added to an appropriate buffer. A Quil A stock solution was prepared as in Example 1 and slowly added to the antigen solution. The composition was homogenized. A cholesterol stock solution was prepared as in Example 1 and was slowly added to the antigen/Quil A solution during homogenization. A DDA stock solution was prepared as in Example 2 and slowly added to the antigen/Quil A/cholesterol solution during homogenization. A DEAE dextran solution was prepared as in Example 9. During homogenization, the DEAE dextran solution was added and the resulting composition was brought to final volume.

Example 13d

Antigen, Quil A, Cholesterol, DDA, DEAE Dextran, Oil

To prepare an immunogenic composition or vaccine composition comprising an antigen, Quil A, cholesterol, DDA, DEAE dextran, and Oil, the desired antigen was added to an appropriate buffer. A Quil A stock solution was prepared as in Example 1 and slowly added to the antigen solution. The composition was homogenized. A cholesterol stock solution was prepared as in Example 1 and was slowly added to the antigen/Quil A solution during homogenization. A DDA stock solution was prepared as in Example 2 and slowly added to the antigen/Quil A/cholesterol solution during homogenization. A DEAE dextran solution was prepared as in Example 9. During homogenization, the DEAE dextran solution was added. An oil composition was prepared as in Example 11. During homogenization, the oil composition was added by feeding the aqueous phase into the oil phase while homogenizing and the resulting composition was brought to final volume.

Example 14

Feline Leukemia Virus (FeLV) Vaccines

Animals were randomly assigned to treatment groups using a randomized complete block design. Table 1 shows the study design. The blocks were based on date of birth and litter. Animals were sorted by date of birth and then litter. Blocks of four were used. Within a block, animals were randomly assigned to treatment. For the vaccination phase of the study, two consecutive blocks were combined to form a group of eight animals. The groups of animals were randomly assigned to two rooms so that each room contained five groups (10 blocks) of animals. Within a group of animals, animals were randomly assigned to four cages located near each other so that each cage contained two animals with the same treatment. For the challenge phase of the study, animals from one vaccination room were randomly assigned to either one or two challenge rooms. The vaccination room selected to go into two challenge rooms, had five blocks randomized to each challenge room (2.5 groups; 20 animals). The other challenge room contained 10 blocks (5 groups; 40 animals). Within a challenge room, animals in the same block were randomly assigned to four cages located near each other.

The vaccines for this study were prepared as in Example 13 except that a 1.5% CARBOPOL® stock solution was used. Specifically, LEUKOCELL® 2 (Pfizer, Inc.) was prepared by propagating FeLV, subgroups A, B, and C, in FeLV-transformed lymphoid cells. Viral antigens were chemically inactivated, combined with a sterile adjuvant to enhance the immune response, and packaged in liquid form. A total amount of 100 mL of Investigational Veterinary Product (IVP) containing the feline leukemia virus and 25 μg Quil A/aluminum hydroxide (ALHYDROGEL®) was prepared. A total of 94.5 mL of a $1.106 \times 10^5$ ng/mL FeLV stock solution was mixed slowly for 15 minutes. The pH was adjusted to 5.9 to 6.1 with 4N HCl or 18% NaOH, if needed. While stirring, 0.5 mL of a 5.0 mg/mL solution of Quil A was added to the antigen solution. Then, 5.0 mL of 100% v/v ALHYDROGEL® was slowly added. The composition was stirred for a minimum of 2 hours at 4° C. The pH was adjusted to between 7.0 and 7.3 with 18% NaOH or 1N HCl, as needed.

The IVP comprising the feline leukemia virus and 37.5 µg Quil A/aluminum hydroxide (ALHYDROGEL®) was prepared in the same manner as for the 25 µg Quil A IVP but 7.5 ml of the Quil A stock solution was added to the antigen solution.

A total amount of 350 mL of Investigational Veterinary Product (IVP) containing the feline leukemia virus, Quil A, Cholesterol, DDA, and CARBOPOL® was prepared. While stirring 349.3 mL of a $1.106 \times 10^5$ ng/mL FeLV stock solution, 0.14 mL of a 50.0 mg/mL solution of Quil A was slowly added to the antigen solution. Then, 0.39 mL of an 18 mg/mL cholesterol/ethanol solution was slowly added. The composition was homogenized for three minutes at 10,000 rpm. A total of 0.19 mL of an 18.0 mg/mL DDA/ethanol solution was added to the composition while stirring. A total of 5.0 mL of a 1.5% CARBOPOL® solution was slowly added to 145.0 mL of the feline leukemia virus, Quil A, Cholesterol, and DDA composition. The pH was adjusted to between 7.0 and 7.3 with 18% NaOH or 1N HCl, as needed.

route on Days 1 and 2 following the first vaccine dose administration, and on Days 22 and 23 following the second vaccine dose administration. Injection site reactions (swellings) were also determined on Day 1 after the first vaccination and on Days 22 and 23 after the second vaccination. A blood sample (1.0-2.0 mL) was collected from each animal by venipuncture of the jugular vein, on Day 35, processed for serum separation, and stored at −20° C. or colder until tested.

On Day 35, animals were placed into individual isolation cages. The challenge virus was virulent Feline Leukemia Virus (FeLV), Rickard strain, titered at approximately $10^{6.1}$ TCID50/mL. The FeLV challenge material was thawed and kept on wet ice prior to administration. Animals were challenged on Days 37, 40, 42, and 44, by administering 1.0 mL by the nasal route of undiluted challenge material. A 1 mL tuberculin syringe, without the needle, was filled with the challenge material. Each kitten was administered approximately 0.5 mL per nostril. On Day 42, challenge

TABLE 1

Experimental Design

| Treatment Group | IVP[a] | Number of Animals | Vaccination Phase | | | Challenge Phase | | | Sample Collection Day |
|---|---|---|---|---|---|---|---|---|---|
| | | | Vaccination Day | Dose (ml) | Route | Challenge Day | Dose (ml) | Route | |
| T01 | Saline | 20 | 0, 21 | 1.0 | SC[c] | 37, 40, 42[d], 44 | 1.0 | ON[e] | −2, 35, 64, 85, 106, 127, 134, 141, 148, 155 |
| T02 | LEUKOCELL® 2 25 µg Quil A/ Al(OH)[b] | 20 | 0, 21 | 1.0 | SC | 37, 40, 42[d], 44 | 1.0 | ON | −2, 35, 64, 85, 106, 127, 134, 141, 148, 155 |
| T03 | LEUKOCELL® 2 37.5 µg Quil A/ Al(OH)[b] | 20 | 0, 21 | 1.0 | SC | 37, 40, 42[d], 44 | 1.0 | ON | −2, 35, 64, 85, 106, 127, 134, 141, 148, 155 |
| T04 | Reformulated LEUKOCELL® 2 20 µg Quil A/ Cholesterol/DDA/ CARBOPOL®[b] | 20 | 0, 21 | 1.0 | SC | 37, 40, 42[d], 44 | 1.0 | ON | −2, 35, 64, 85, 106, 127, 134, 141, 148, 155 |

[a]Investigational Veterinary Product
[b]Blended to contain a relative potency comparable to the reference vaccine (FeLV Reference Lot No. 12)
[c]SC = Subcutaneous
[d]Depo-Medrol ®: Day 42 (approximately 5.0 mg/kg) by the intramuscular route
[e]ON = Oronasal
Quil A - Cholesterol = Saponin adjuvant Quil A, incorporated into lipid particles of cholesterol
CARBOPOL ® = Carbomer
DDA = Dimethyldioctadecylammonium bromide All animals were observed daily and observations were recorded. Body temperatures were recorded from all animals by the tympanic route on Day −1 prior to the first vaccine dose administration and on Day 20 prior to the second vaccine dose administration. A blood sample (1.0-2.0 mL) was collected from each animal by venipuncture of the jugular vein, on Day −2. Sedative doses of TELAZOL® (Fort Dodge Animal Health) were administered according to body weight (approximately 5.0 mg/kg) by the intramuscular route in order to minimize animal stress and to avoid injury to animal handlers during blood collection. Blood was collected in serum separation tubes (SST) and processed for serum separation. Serum was stored at −20° C. or colder until tested.

Placebo or FeLV vaccines were administered to kittens by the subcutaneous route at a 1.0 mL dose. The first vaccination was performed on Day 0 and the second vaccine administration was performed on Day 21. All animals were observed for approximately one hour following the first and second vaccinations for immediate local pain reactions (sting reactions). Observations were documented. Body temperatures of all animals were measured by the tympanic administration was performed approximately 5 h post DEPO-MEDROL® administration. After each day of challenge, a sample of the challenge material was retained for confirmatory titration.

Post-challenge, a blood sample (1.0-2.0 mL) was collected from each animal by venipuncture of the jugular vein, on Days 64, 85, 106, 127, 134, 141, 148, and 155. Sedative doses of TELAZOL® (Fort Dodge) were administered as described above. Blood was collected in serum separation tubes (SST), processed for serum separation, and stored at −20° C. or colder until tested. Serum samples were tested for the presence of FeLV p27 antigen (marker of FeLV infection) by ELISA (IDEXX; Westbrook, Me.). Final results were evaluated by intensity of color development and by spectrophotometer at an optical density of 405/490 nm. For a valid test, the positive control optical density had to fall between 0.131 and 2.999 and the negative control should had optical density below or equal to 0.0039.

Virus isolation was performed using serum samples collected on Days −2 and 35. Serum samples from Days 127 through 155 were considered to evaluate FeLV vaccine efficacy. Serum samples from Day 127 (week 12), Day 134

(week 13), Day 141 (week 14), Day 148 (week 15) and Day 155 (week 16) were tested for the presence of FeLV p27 antigen. An animal was considered persistently infected if it had three or more positive FeLV p27 antigen test results during Days 127 (week 12) through 155 (week 16).

Temperatures were analyzed using a general linear repeated measures mixed model, and pair-wise treatment comparisons were made between treatment T01 and treatments T02, T03, and T04 at each time point if the overall treatment and/or treatment by time point effect was significant. Least squares means, 95% confidence intervals, minimums and maximums were calculated for each treatment at each time point.

Frequency distributions of the presence of sting reactions were calculated for each treatment and time point data were collected. Frequency distributions of the presence of injection site swellings were calculated for each treatment and time point data were collected. Frequency distributions of the presence of post-vaccination systemic reactions were calculated for each treatment.

Immediate reactions were not observed in any of the treatment groups during first and second vaccination. Adverse reactions were not observed in any of the treatment groups at approximately one hour post first and second vaccinations. Neither pyrexia (body temperature ≥39.5° C.) nor hypothermia (body temperature <37.0° C.) was observed in any of the treatment groups after the first and second vaccinations. There were no significant differences in mean body temperature between treatment groups at any time point (p>0.08). Injection site swellings were not observed in any of the treatment groups after first and second vaccinations.

Final results from week 12 to week 16 post-challenge indicated that 16 out of 19 animals (84%) that received the placebo vaccine (T01 group) were persistently viremic to FeLV. 13 out of 19 animals (68%) in the T02 group were protected from FeLV virulent challenge. The level of protection was statistically significant (p=0.0004) compared to the placebo vaccinated kittens. 12 out of 19 animals (63%) in the T03 group were protected from FeLV virulent challenge. The level of protection was statistically significant (p=0.0013) compared to the placebo vaccinated kittens. 19 out of 20 animals (95%) in the T04 group were protected from FeLV virulent challenge. The level of protection was statistically significant (p=0.0001) compared to the placebo vaccinated kittens.

Thus, the vaccines administered to the T02, T03 and T04 groups were all demonstrated to be safe in kittens at the minimum age when administered at a two-dose regimen, three weeks apart. Additionally, the vaccines administered to these groups were also able to significantly reduce the level of FeLV persistent viremia in kittens at the minimum age when administered at a two-dose regimen, three weeks apart. There was a statistically significant reduction in the establishment of FeLV persistent viremia in kittens in the T02, T03 and T04 groups. Additionally, there was a statistically significant difference between T04 and the other vaccine groups (T02, T03). It was surprising and unexpected that vaccines containing the novel adjuvant formulation proved to be more efficacious that those containing adjuvant components commonly used in cats.

Example 15

Feline Leukemia Virus Vaccines

Kittens were acclimated for sixteen days after arrival. Animals were then randomly assigned to a room, and within a room, were randomly assigned to treatments (1 animal per treatment in each room). A blood sample (1.0-2.0 mL) was collected from each animal by venipuncture of the jugular vein on Study Day −1. Sedative doses of TELAZOL® (Fort Dodge Animal Health) were administered according to body weight (approximately 5.0 mg/kg) by the intramuscular route in order to minimize animal stress and to avoid injury to animal handlers during blood collection. Blood was collected in serum separation tubes and processed for serum separation. All animals were also observed daily, and observations were recorded.

Vaccines were prepared as in Example 13 except that a 1.5% CARBOPOL® Stock solution was used. LEUKOCELL® 2 was prepared by propagating FeLV, subgroups A, B, and C, in FeLV-transformed lymphoid cells. Viral antigens were chemically inactivated, combined with a sterile adjuvant to enhance the immune response, and packaged in liquid form. A total amount of 500.0 mL of IVP containing the feline leukemia virus at a relative potency (RP) of 2, Quil A, Cholesterol, and DDA was prepared in the following manner. A total of 20.7 mL of a FeLV stock solution (50.0 RP/mL where 1 RP=3,624 ng/mL of antigen) was added to 478.2 mL 0.063% PBS buffer. While stirring, 0.21 mL of a 50.0 mg/mL solution of Quil A was slowly added to the antigen solution. Then, 0.58 mL of an 18 mg/mL cholesterol/ethanol solution was slowly added. A total of 0.29 mL of an 18.0 mg/mL DDA/ethanol solution was slowly added to the composition while stirring. The composition was homogenized for three minutes at 10,000 rpm. The composition was then microfluidized by one pass through a 200 micron limiting dimension chamber at 10,000 (+500) psi. While stirring, 10.0 mL of a 1.5% CARBOPOL® solution was slowly added to 290.0 mL of the feline leukemia virus, Quil A, Cholesterol, and DDA composition. The pH was adjusted to between 7.0 and 7.3 with 18% NaOH or 1N HCl, as needed.

The IVP containing the feline leukemia virus at a RP of 5 was prepared in the same manner as the IVP with a RP of 2 using 51.7 mL of the FeLV stock solution and 447.2 mL 0.063% PBS buffer, with the amounts of the other components remaining the same.

The IVP containing the feline leukemia virus at a RP of 10 was prepared in the same manner as the IVP with a RP of 2 using 93.1 mL of the FeLV stock solution, 355.9 mL 0.063% PBS buffer, 0.19 mL of the Quil A solution, 0.52 mL of the cholesterol solution, and 0.26 mL of the DDA solution (450 mL total volume). Then, 8.3 mL of a 1.5% CARBOPOL® solution was slowly added to 241.7 mL of the feline leukemia virus, Quil A, Cholesterol, and DDA composition.

The IVP containing the feline leukemia virus at a RP of 15 was prepared in the same manner as the IVP with a RP of 10 using 139.7 mL of the FeLV stock solution and 309.4 mL 0.063% PBS buffer, with the amounts of the other components remaining the same.

The IVP containing the feline leukemia virus at a RP of 20 was prepared in the same manner as the IVP with a RP of 2 using 206.9 mL of the FeLV stock solution and 292.0 mL 0.063% PBS buffer, with the amounts of the other components remaining the same.

For administering a 0.5 mL dose, 300.0 mL of IVP containing the feline leukemia virus at a RP of 5, Quil A, Cholesterol, DDA, and CARBOPOL® was prepared in the following manner. A total of 21.7 mL of a FeLV stock solution (35.8 RP/mL where 1 RP=1,864 µg/mL of antigen) was added to 277.7 mL 0.063% PBS buffer. While stirring, 0.12 mL of a 50.0 mg/mL solution of Quil A was slowly added to the antigen solution. Then, 0.35 mL of an 18 mg/mL cholesterol/ethanol solution was slowly added. A total of 0.17 mL of an 18.0 mg/mL DDA/ethanol solution was slowly added to the composition while stirring. The composition was homogenized for three minutes at 10,000 rpm. The composition was then microfluidized by one pass through a 200 micron limiting dimension chamber at 10,000 (+500) psi. While stirring, 3.3 mL of a 1.5% CARBOPOL® solution was slowly added to 96.7 mL of the feline leukemia virus, Quil A, Cholesterol, and DDA composition. The pH was adjusted to between 7.0 and 7.3 with 18% NaOH or 1N HCl, as needed.

The IVP for administering a 1.0 mL dose of the feline leukemia virus at a RP of 5, Quil A, Cholesterol, DDA, and CARBOPOL® was prepared in the same manner as for the 0.5 mL dose with the amounts adjusted appropriately.

A total amount of 300.0 mL of IVP containing the feline leukemia virus at a RP of 10 and CARBOPOL® was prepared. A total of 62.1 mL of a FeLV stock solution (50.0 RP/mL where 1 RP=3,624 µg/mL of antigen) was added to 237.9 mL 0.063% PBS buffer. The composition was homogenized for three minutes at 10,000 rpm. The composition was then microfluidized by one pass through a 200 micron limiting dimension chamber at 10,000 (+500) psi. While stirring, 3.3 mL of a 1.5% CARBOPOL® solution was slowly added to 96.7 mL of the feline leukemia virus composition. The pH was adjusted to between 7.0 and 7.3 with 18% NaOH or 1N HCl, as needed.

Placebo and FeLV vaccines (Table 2) were administered to kittens by the subcutaneous route using a 22 gauge×¾" needle and 3 cc syringe on Study Day 0 and Study Day 20. Treatment group T01 was administered the placebo vaccine at a 1.0 mL dose. Treatment groups T02, T04, T05, T06, T07, T08 and T09 were administered the FeLV vaccines at a 1.0 mL dose. Treatment group T03 was administered the FeLV vaccine at a 0.5 mL dose. Treatment group T10 was administered the FeLV canarypox vaccine (Merial) by the intradermal route using an intradermal gun injector.

All animals were observed following first vaccination (Study Day 0) and second vaccination (Study Day 20) for signs of pain upon test vaccine administration including vocalization, scratching/biting and aggressive or escape attempt. Post-vaccination attitude (normal or abnormal) was also documented. All animals were observed for approximately one hour after vaccine administration on Study Day 0 and Study Day 20 for the development of adverse systemic reactions. Observations were documented. The vaccination sites were palpated, and pain at injection site, redness at injection site, injection site swelling and size of swelling were recorded. Observations were performed on Study Days 2, 5 and 9 after the first vaccination, and on Study Days 25, 28 and 32 after the second vaccination. Observations were documented.

A blood sample (1.0-2.0 mL) was collected from each animal by venipuncture of the jugular vein on Study Day 32 (pre-challenge). Animals were challenged on Study Days 34, 36, 39, and 41 by administering 1.0 mL by the nasal route of undiluted challenge material. A 1 mL tuberculin syringe, without the needle, was filled with the challenge material. Each kitten was given approximately 0.5 mL per nostril. The FeLV challenge material had an average titer of $10^{6.1}$ $TCID_{50}$/mL. A blood sample (1.0-2.0 mL) was then collected from each animal by venipuncture of the jugular vein on Study Days 61, 83, 106, 126, 133, 138, 146, and 152.

Results—Safety

During the first (Study Day 0) vaccination, three animals in treatment group T09 demonstrated immediate sting-type reactions. During the second vaccination (Study Day 20), one animal from treatment group T05, four from treatment

TABLE 2

Experimental Design

| Treatment Group | Target Number Animals | Target Relative Potency | Route of Vaccination | Vaccine | Adjuvant | Cell Culture Media (Harvest Bulk) |
|---|---|---|---|---|---|---|
| T01 | 10 | N.A. | SC | PBS | No Adjuvant | Normal Saline |
| T02 | 10 | 5 RP | SC | Inactivated FeLV | Quil A - Cholesterol DDA - CARBOPOL ® | RPMI |
| T03 | 10 | 5 RP | SC/0.5 mL | Inactivated FeLV | Quil A - Cholesterol DDA - CARBOPOL ® | RPMI |
| T04 | 10 | 20 RP | SC | Inactivated FeLV | Quil A - Cholesterol DDA - CARBOPOL ® | Cellgro |
| T05 | 10 | 15 RP | SC | Inactivated FeLV | Quil A - Cholesterol DDA - CARBOPOL ® | Cellgro |
| T06 | 10 | 10 RP | SC | Inactivated FeLV | Quil A - Cholesterol DDA - CARBOPOL ® | Cellgro |
| T07 | 10 | 5 RP | SC | Inactivated FeLV | Quil A - Cholesterol DDA - CARBOPOL ® | Cellgro |
| T08 | 10 | 2 RP | SC | Inactivated FeLV | Quil A - Cholesterol DDA - CARBOPOL ® | Cellgro |
| T09 | 10 | 10 RP | SC | Inactivated FeLV | CARBOPOL ® | Cellgro |
| T10 | 10 | Live rFeLV (Merial) | ID | Live rFeLV (Merial) | No Adjuvant | Proprietary (Merial) | group T08, and two from treatment group T09 demonstrated immediate sting-type reactions.

During the first vaccination, three animals from treatment group T09 demonstrated minor vocalization. The animals presenting pain at first vaccination also presented minor vocalization at that time. During the second vaccination, one animal from treatment group T05, four from treatment group T08, and two from treatment group T09 demonstrated minor vocalization. The animals presenting pain at second vaccination also presented minor vocalization at that time.

During the first vaccination, three animals in treatment group T09 demonstrated aggressive behavior/attempt to escape. During the second vaccination, one animal from treatment group T05, four from treatment group T08, and two from treatment group T09 demonstrated aggressive behavior/attempt to escape.

None of the treatment groups presented scratching/biting at injection site upon first or second vaccination. Injection site reactions were not observed in any of the treatment groups post first or second vaccination. Adverse reactions were also not observed in any of the treatment groups.

Results—Efficacy

All animals tested negative prior to vaccination for FeLV p27 antigen from serum samples collected on Day −1. All animals also tested negative prior to challenge for FeLV p27 antigen from serum samples collected on Day 32.

Final results from week 12 to week 16 post-challenge (Table 3) indicated that 9 out of 10 animals (90%) in treatment group T01 (placebo) were persistently viremic to FeLV. Results from the same period indicated that 6 out of 10 animals (60%) in treatment group T02 were protected from FeLV virulent challenge; this level of protection was not statistically significant (p=0.0573) compared to the placebo vaccinated kittens. Nine out of 10 animals (90%) in treatment group T03 were protected from FeLV virulent challenge; this level of protection was statistically significant (p=0.0011) compared to the placebo vaccinated kittens. 10 out of 10 animals (100%) in treatment group T04 were protected from FeLV virulent challenge; this level of protection was statistically significant (p=0.0001) compared to the placebo vaccinated kittens. 10 out of 10 animals (100%) in treatment group T05 were protected from FeLV virulent challenge; this level of protection was statistically significant (p=0.0001) compared to the placebo vaccinated kittens. 7 out of 10 animals (70%) in treatment group T06 were protected from FeLV virulent challenge; this level of protection was statistically significant (p=0.0198) compared to the placebo vaccinated kittens. 10 out of 10 animals (100%) in treatment group T07 were protected from FeLV virulent challenge; this level of protection was statistically significant (p=0.0001) compared to the placebo vaccinated kittens. 8 out of 10 animals (80%) in treatment group T08 were protected from FeLV virulent challenge; this level of protection was statistically significant (p=0.0055) compared to the placebo vaccinated kittens. 5 out of 10 animals (50%) in treatment group T09 were protected from FeLV virulent challenge; this level of protection was not statistically significant (p=0.1409) compared to the placebo vaccinated kittens. Finally, 6 out of 10 animals (60%) in treatment group T10 were protected from FeLV virulent challenge; this level of protection was not statistically significant (p=0.0573) compared to the placebo vaccinated kittens.

TABLE 3

Summary of Level of Protection

| Treatment Group | Vaccine Relative Potency | Level of Protection | Preventive Fraction |
|---|---|---|---|
| T01 | NA | 10% | |
| T02 | 4.58 | 60% | 55.6% |
| T03 | 4.58 | 90% | 88.9% |
| T04 | 26.32 | 100% | 100% |
| T05 | 18.58 | 100% | 100% |
| T06 | 11.16 | 70% | 66.7% |
| T07 | 4.77 | 100% | 100% |
| T08 | 1.64 | 80% | 77.8% |
| T09 | 11.12 | 50% | 44.4% |

The vaccines used in treatment groups T02, T03, T04, T06 and T07 demonstrated a satisfactory safety profile during the first vaccination, as no reactions were observed at that time. A single animal in treatment group T05 demonstrated an immediate reaction (pain at administration, minor vocalization and aggressive/escape attempt) at the second vaccination. This event might be associated with an exacerbated response to vaccination for the particular animal rather than to a vaccine formulation problem. All vaccines demonstrated a satisfactory safety profile post-vaccination, since neither local reactions nor adverse events related to vaccination were observed.

FeLV vaccines administered to treatment groups T03, T04, T05, T07 and T08 demonstrated satisfactory efficacy, since ≥80% protection (≥75% preventive fraction) was achieved after challenge with virulent FeLV. That the vaccine given to group T07 provided 100% protection is surprising and unexpected, as animals in that group received 25% and 33% of the antigen dose of animals in groups T04 and T05, respectively. A clear advantage of the adjuvants disclosed and tested herein is that they allow for a smaller dose of antigen to be used, while still inducing a fully protective immune response. Vaccines administered to treatment groups T02, T06 and T09 demonstrated a somewhat decreased efficacy (<80% protection; preventive fraction <75%) following challenge with virulent FeLV. The decreased efficacy of the vaccine administered to treatment group T02 was possibly do to the presence of low responder animals in that group.

Example 16

In Ovo Vaccination against *Eimeria* in Chickens

Avian coccidiosis is an intestinal disease generally caused by protozoa of the genus *Eimeria*, and represents a serious worldwide problem for the poultry industry. Parasites ingested during feeding localize to the intestinal tract where they cause serious damage to intestinal and underlying tissues. Resultant economic losses to the poultry industry are very significant, since feed conversion and weight gain of both broiler and egg-laying birds are impaired. A general summation of the state of the art, including attempts to vaccinate against *Eimeria* using, for example, recombinant *Eimeria* proteins as antigen and a variety of adjuvant systems, are described in the following publications, all of which are incorporated by reference herein, as if fully set forth, (1) H. S. Lillehoj et al., *J. Parisitol*, 91(3), 2005, pp. 666-673; (2) H. S. Lillehoj et al., *Avian Diseases*, 49 2005, 112-117; and (3) R. A. Dalloul et al., Expert Rev. Vaccines, 5(1), 2006, pp. 143-163. The present Example is directed to the use of novel vaccine compositions that employ adjuvant components that provide superior performance in the context of coccidiosis.

The highly effective adjuvants of the present invention may be used in combination with antigenic material from all Eimeria species, including purified or partially purified protein extracts thereof, or by way of one or more recombinantly expressed proteins thereof, or fragments of any and all such proteins, thus to include antigenic materials provided from *Eimeria acervulina, Eimeria ahsata, Eimeria bovis, Eimeria brunetti, Eimeria fraterculae, Eimeria maxima, Eimeria meleagridis, Eimeria mitis, Eimeria necatrix, Eimeria praecox, Eimeria stiedae, Eimeria tenella*, and *Eimeria zurnii*, among others.

The adjuvanted vaccine of the invention may be provided against any protein or macromolecule that is produced at one or more points in the life cycle of the protozoan, including, without limitation, oocyst (whether sporulated or unsporulated), sporocyst, sporozoite, schizont, merozoite, male or female gamete cells. In a preferred example, proteins that are shed into the feces in significant amounts in the oocyst stage are the preferred materials to act as the source of recombinant protein antigen, or partially or wholly purified samples of such protein as purified by conventional means.

Additional examples of *Eimeria* proteins useful as sources of antigen in the formulation of the present vaccines include those as described by Karkhanis et al. *Infection and Immunity*, 1991, pp. 983-989, including protective antigens, as described therein, having a mass range of about 20 to about 30 kDA. Additional example include the *Eimeria* 23 kDA 3-1E protein, and the Etp100 protein, for example as recovered from *E. tenella*.

The highly effective adjuvants of the present invention may be used in combination with antigenic material from *Neurospora caninum*.

Additionally, the highly effective adjuvants of the present invention may be used in combination with any of the following protozoan pathogens, *Cryptosporidium parvum* (cryptosporidiosis), *Cyclospora cayetanensis* (cyclosporiasis), *Isospora belli* (isosporiasis), *Toxoplasma gondii* (toxoplasmosis), *Plasmodium* (malaria), and *Babesia* spp. (babesiosis), and related protozoans, generally of the Apicomplexen group causing these or related diseases.

The effectiveness of in ovo delivery of vaccines that contain particular adjuvant systems was evaluated as follows.

Materials and Methods:
1. Materials:

Recombinant *E. maxima* protein (of protein 3-1E) was expressed in *E. coli* and affinity-column purified. Crude preparation of whole cell *E. maxima* macromolecules (solubilized with detergent from disrupted cells) were also used as antigen, with this crude antigen being referred to as "EM". In a preferred example, the adjuvant was as described in Example 8 above, and is prepared as provided according to that Example protocol (see Page 41). Therefore, in a typical example, each embryo would receive an injection into the amnion (i.e. to include the amnionic fluid and space) of about 50 to about 100 microliters of vaccine solution, which, for each 1 ML thereof comprises: about 50 or 100 micrograms of recombinant 3-1E protein or other protein species, or alternatively, about 50 or 100 micrograms of crude cell "EM" extract; about 20 micrograms Quil A; about 20 micrograms cholesterol; CARBOPOL at about 0.075% (v/v); about 10 micrograms of DDA; and about 250 micrograms R1005, all provided in, for example, 20 mM PBS.

In connection with selection of the saponin for use herein, the following additional information is instructive. The defined term saponin refers to the plant derived glycosides, a number of which have been studied extensively for their biological properties (The Plant Glycosides, McIlroy, R. J., Edward Arnold and co., London, 1951). The saponins used most predominantly in the art for the production of vaccines are those derived from the plants *Quillaja saponaria molina, Aesculus hippocastanum* or *Gyophilla struthium*. Extracts of the bark of *Quillaja saponaria molina* which are known to have adjuvant activity are known, for example Quil A Also pure fractions of Quil A have been described which retain adjuvant activity whilst being less toxic than Quil A, for example QS21. QS21 is also described in Kensil et al. (1991. *J. Immunology* vol 146, 431-437). When mixed with the further adjuvant ingredients of the present invention, as heretofor and hereinafter described, such saponin-containing materials become highly effective materials. Additional effective formulations include those that use Escin, which has been described in the Merck index (12th ed: entry 3737) as a mixture of saponins occurring in the seed of the horse chestnut tree. In the preferred embodiment of the present invention, saponin refers to "Quil-A" sold in the USA by E.M Sergeant company.

It should further understood that saponin extracts can be used as mixtures or purified individual components therefrom such fractions/products including QS-7, QS-17, QS-18, and QS-21 from Antigenics Company, Massachusetts, USA or similar crude, fractioned or refined saponin products, and mixtures thereof offered by Isconova Company of Sweden. In one embodiment the Quil A is at least 85% pure. In other embodiments, the Quil A is at least 90%, 91%, 92%, 93%, 94%, 95%, 96%, 97%, 98%, or 99% pure.

2. Embryo Vaccination:

Eggs were purchased from the Moyers Hatchery, Quakertown, Pa. For in ovo immunization, broiler eggs were then incubated for 18 days, and candled to select (at 18 days of embryonation) fertile eggs, and then injected with 20 mM PBS and either adjuvant alone, or adjuvant formulated with either recombinant 3-1E protein or an "EM" preparation. Injections were made on an "Intelliject" in ovo injector (Avitech, Hebron, Md.) according to the manufacturer's instructions. Each egg received 100 microliter samples into the amnionic cavity using a 17.5 cm-long 18-gauge needle provided by Avitech (Hebron, Md.). 50 microliter doses are also among those operable in the practice of the present invention.

3. Chickens:

As soon as broiler chickens were hatched (at about day 21-22), they were transported to the laboratory using disposable chicken transporting cartons (Frederick Packaging, Inc., Milwaukee, Wis.) and the chicks were then housed in the Petersime units and provided with feed and water ad libitum.

Birds were kept in brooder pens in an *Eimeria*-free facility and transferred into large hanging cages in separate locations where they were infected with live oocysts of *Eimeria maxima* and kept there until the end of experimental period.

4. Parasites:

USDA BARC strain of *Eimeria maxima* #41, which has been maintained in the Animal Parasitic Diseases Laboratory-BARC and propagated according to the established procedure in Dr. Lillehoj's laboratory, was used. The freshly produced oocysts from the strain of *E. maxima* (Beltsville #41) were cleaned by floatation on 5% sodium hypochlorite, washed three times with PBS, and viability was enumerated by trypan blue using a hemocytometer.

5. *Eimeria* Challenge Infection:

Seven day-old birds were wing-tagged and the birds of all experimental groups except uninfected control groups were inoculated esophageally with *E. maxima* using an inoculation needle, and were then placed into oocysts collection cages.

6. Body Weight Gain Determination:

Body weights of individual birds were determined at days 0 (uninfected), 6 and 10 days post infection with *E. maxima*.

7. Assessment of Fecal Oocyst Production:

Animal caretakers were instructed not to clean the cages, and fecal droppings were collected. Collecting pans were placed under each cage for 5 days starting from the $6^{th}$ day post infection, and fecal materials were collected into large plastic jars (2 L). Fecal droppings soaked with tap water in each jar were ground in a blender with more water (total volume is 3 L), and two 40 ml random samples were taken from each sample and stored in refrigerator until they were counted. In order to count coccidia oocysts, various dilutions were made initially to determine the optimum dilutions for the enumeration of oocysts for each sample. Oocysts were counted microscopically using a McMaster counting chamber using a sucrose floatation method which has been established in Dr Lillehoj's laboratory. The total number of oocysts shed per chicken was calculated using the formula: total oocysts/bird=(oocyst count×dilution factor×fecal sample volume/counting chamber volume)/number of birds per cage.

8. Sample Collection:

Blood was collected on the $6^{th}$ day following the date of infection, and serum antibody response was determined. Blood samples were obtained from individual birds (N=4-5/group), allowed to clot 4 hr at 4° C., and the sera collected. Serum samples were tested for anti-*Eimeria* antibodies using ELISA. Briefly, microtiter plates were coated overnight with 10 μg/well of the recombinant coccidial antigens Ea3-1E, EtMIF or EtMIC2, washed with PBS-0.05% Tween, and blocked with PBS-1% BSA. Serum dilutions (1:20, 1:40, 1:80, 1:160; 100 μl/well) were added, incubated with continuous gentle shaking, washed, and bound Ab detected with peroxidase-conjugated rabbit anti-chicken IgG (Sigma) and peroxidase-specific substrate. Optical density (OD) was determined at 450 nm with a microplate reader (Bio-Rad, Richmond, Calif.).

Intestine tissues were collected at hatch, and at 6 and 10 days thereafter, and tested for cytokine (IFN-γ, IL-2) production by using Real-time RT-PCR, as a measure of Th1 stimulation.

9. cDNA Synthesis

Total RNA was extracted from intestinal IELs using TRIzol (Invitrogen, Carlsbad, Calif.). Five micrograms of RNA were treated with 1.0 U of DNase 1 and 1.0 μl of 10× reaction buffer (Sigma), incubated for 15 min at room temperature, 1.0 μl of stop solution was added to inactivate DNase I, and the mixture was heated at 70° C. for 10 minutes. RNA was reverse-transcribed using the StrataScript first-strand synthesis system (Stratagene, La Jolla, Calif.) according to the manufacturer's recommendations.

10. Quantitative RT-PCR

Quantitative RT-PCR oligonucleotide primers for chicken interferon-γ (IFN-γ) and GAPDH control are listed in Table 4. Amplification and detection were carried out using equivalent amounts of total RNA from intestinal IELs using the Mx3000P system and Brilliant SYBR Green QPCR master mix (Stratagene). Standard curves were generated using $\log_{10}$ diluted standard RNA and levels of individual transcripts were normalized to those of GAPDH analyzed by the Q-gene program. Each analysis was performed in triplicate. To normalize RNA levels between samples within an experiment, the mean threshold cycle ($C_t$) values for the amplification products were calculated by pooling values from all samples in that experiment.

TABLE 4

Oligonucleotide primers used for quantitative RT-PCR of chicken IFN-γ and GAPDH.

| RNA target | Primer sequences | PCR product size (bp) |
|---|---|---|
| GAPDH | Accession no. K01458 | 264 |
| Forward | 5'-GGTGGTGCTAAGCGTGTTAT-3' | SEQ ID NO: 1 |
| Reverse | 5'-ACCTCTGTCATCTCTCCACA-3' | SEQ ID NO: 2 |
| IFN-γ | Accession No. Y07922 | 259 |
| Forward | 5'-GCTGACGGTGGACCTATTATT-3' | SEQ ID NO: 3 |
| Reverse | 5'-GGCTTTGCGCTGGATTC-3' | SEQ ID NO: 4 |
| IL-1β | Accession No. Y15006 | 244 |
| Forward | 5'-TGGGCATCAAGGGCTACA-3' | SEQ ID NO: 5 |
| Reverse | 5'-TCGGGTTGGTTGGTGATG-3' | SEQ ID NO: 6 |
| IL-15 | Accession No. AF139097 | 243 |
| Forward | 5'-TCTGTTCTTCTGTTCTGAGTGATG-3' | SEQ ID NO: 7 |
| Reverse | 5'-AGTGATTTGCTTCTGTCTTTGGTA-3' | SEQ ID NO: 8 |

Spleen was collected before inoculation with *E. maxima* and at $10^{th}$ DPI (date post infection) for splenocyte proliferation assay. Spleens were placed in a Petri dish with 10 ml of Hank's balanced salt solution (HBSS) supplemented with 100 U/ml penicillin and 100 μg/ml streptomycin (Sigma, St. Louis, Mo.). Single cell suspensions of spleen lymphocytes were prepared and lymphocyte proliferation was carried out. In brief, splenocytes were adjusted to $5 \times 10^6$ or $1 \times 10^7$ cells/ml in IMDM medium (Sigma) supplemented with 10% fetal bovine serum (FBS) (Hyclone, Logan, Utah), 100 U/ml penicillin, and 100 μg/ml streptomycin (Sigma), which will be called 10% complete IMDM medium. Splenocytes (100 μl/well) were incubated in 96-well flat bottom plates at 41° C. in a humidified incubator (Form a, Marietta, Ohio) with 5% $CO_2$ and 95% air for 48 hr. Cell proliferation was determined with 2-(2-methoxy-4-nitrophenyl)-3-(4-nitrophenyl)-5-(2,4-disulfophenyl)-2H-tetrazolium, monosodium salt (WST-8, Cell-Counting Kit-8®, Dojindo Molecular Technologies, Gaithersburg, Md.). Optical density (OD) was measured at 450 nm using a microplate spectrophotometer (BioRad, Richmond, Calif.).

Results

Results showed that the broiler birds vaccinated with 100 microliters of adjuvant formulation (i.e. 100 microliters including recombinant 3-1E protein according to the previously defined doses) gained about an additional 45 to 85 grams of body weight compared to the birds unvaccinated but infected with *E. maxima*.

The vaccines of the invention also showed clear effects on cell-mediated immunity as measured by mitogenic lymphocyte proliferation assays: The results of spleen lymphocyte proliferation at $1 \times 10^7$ cells/ml incubated with Con A for 48 hours showed that the splenocytes from *E. maxima*-infected chickens immunized with Pfizer adjuvant with or without antigen in general show higher levels of lymphocyte proliferation, especially when a 50 ug dose was used. Significant enhancement of IL-1B production, IFN-γ production, and IL-15 production, most particularly in the spleen was seen following administration of the adjuvated vaccine compositions of the invention. In summary, these results clearly indicate the effect of present adjuvant on cytokine response and support its effect on enhancing cell-mediated rather than humoral immune response.

The vaccines of the invention also showed clear effects on fecal oocyst output. Uninfected control birds did not shed any oocysts. Following *E. maxima* infection, there were significant reductions of fecal oocysts output in groups which were treated with Pfizer adjuvants alone. Birds vaccinated in ovo with crude *Eimeria maxima* and adjuvant demonstrated much less fecal oocysts output compared to groups inoculated with crude *Eimeria maxima* preparation alone. EM groups.

It should be noted that although purified recombinant *E. maxima* protein 3-1E has been used in the practice of the aforementioned experiments, use of recombinant Ea3-1E, EaMIF, and EtMIC2 antigens, either singularly or in combination with 3-1E, or each other, or as any combination of any thereof, is also a preferred embodiment of the invention, and generally all *Eimeria* protein antigens are operable in the practice of the present invention, as long as when mixed with the adjuvants of the present invention.

Example 17

Evaluation of *Escherichia coli* J5 Strain Bacterin in Cattle

The objective of the study is to evaluate immunologic response in cattle to *Escherichia coli* (J-5 strain) antigen when administered in various novel formulations. The commercial J5 bacterin is sold as a preventative vaccine for coliform mastitis in dairy cattle and is moderately effective in its current formulation. Prior to vaccination, animals were determined to be of low titer for antibodies to *E. coli* J5, based respectively on serum blood sample analysis taken prior to vaccination.

Beef Cattle

Experimental vaccines were formulated using inactivated *E. coli* J5 bacterin as the antigen, and were made according to Example 13 above. Each treatment group initially contained seven animals (Table 5). One treatment group received saline (T01) and another group received a commercial J5 vaccine (T02-Enviracor™ Pfizer J-5 *Escherichia coli* bacterin). The other treatment groups received various formulations containing the adjuvants specified in Table 5. All vaccinations were administered by subcutaneous injection on study days 0 and 21. The dosing volume was 5 mL.

TABLE 5

Vaccine Groups - Beef Cattle

| Tmt Group | # of Animals | Treatment | Day | Dose (ml) | Route |
|---|---|---|---|---|---|
| T01 | 7 | Saline | 0, 21 | 5.0 | SC |
| T02 | 7 | *Escherichia coli* Bacterin, J-5 strain | 0, 21 | 5.0 | SC |
| T03 | 7 | QCDCR | 0, 21 | 5.0 | SC |
| T04 | 7 | QCDO | 0, 21 | 5.0 | SC |
| T05 | 7 | QCDX | 0, 21 | 5.0 | SC |
| T06 | 7 | QCDXO | 0, 21 | 5.0 | SC |

In Table 5, QC is the abbreviation for QuilA/cholesterol, D for DDA, C for carbopol, R for R1005, X for DEAE-dextran and O for oil.

Stock solutions were prepared as in Examples 1 to 13 above for the following: *E. coli* was given as about $4-5 \times 10^9$ organisms per dose as determined by direct count by light microscopy. Quil A in water at 50 mg/ml, Cholesterol in ethanol at 17 mg/ml, DDA in ethanol at 17 mg/ml, R1005 in 20 mM phosphate buffer at 5 mg/ml, DEAE-dextran in water at 200 mg/ml, TLR agonist in TE buffer at 20 mg/ml and Iscomatrix in water at 5.4 mg/ml. The individual components were added v/v in the order of letter symbols from left to right. For example, QCDC the appropriate volume of Quil A was added followed by addition of cholesterol, DDA and finally carbopol. When the formulations contained oil, the separate components were add mixed then emulsified into a mixture of Drakeol® 5 LT mineral oil with either Span 80 and Tween 80 (QCDO) or Span 85 and Tween 85 (QCDXO). Drakeol® is a commercially available light mineral oil Blood samples were collected on study days 0, 21 and 49 for serological testing. Antibody titers to *E. coli* J5 in serum samples were determined by means of J5-specific, indirect ELISA assay. IgG antibody isotypes were determined with sheep-anti-bovine antibody conjugates (Bethyl Labs). Titers were determined and expressed as their geometric means.

Results

The serological results of the study are shown in Tables 6-8. Higher antibody titers generally are associated with better protection of vaccines. The total J5-specific IgG titer is shown in Table 6. Several of the formulations of the present invention produced much higher titers than the commercial product, even though these formulations had a similar amount of J5 antigen added. The QCDO, QCDX, and QCDXO formulations were especially effective in inducing a good immune response in these cattle.

TABLE 6

IgG antibody titers.

| Tmt Group | Treatment | Geometric mean IgG Titer to J5 at day | | |
|---|---|---|---|---|
| | | 0 | 21 | 48 |
| T01 | Saline | 1573 | 3135 | 2795 |
| T02 | *Escherichia coli* Bacterin | 1402 | 7011 | 55524 |
| T03 | QCDCR | 1573 | 13975 | 49494 |
| T04 | QCDO | 1764 | 62289 | 391951 |
| T05 | QCDX | 993 | 22135 | 110672 |
| T06 | QCDXO | 2221 | 69877 | 620779 |

The J5-specific IgG1 antibody isotypes were determined. These results are shown in Table 7. Again, QCDO, QCDX, and QCDXO formulations were especially effective in inducing a good immune response in these cattle. These formulations gave much higher titers with even a single vaccination than the commercial vaccine did with two injections.

TABLE 7

IgG1 antibody titers.

| Tmt Group | Treatment | Geometric mean IgG1 Titer to J5 at day | | |
|---|---|---|---|---|
| | | 0 | 21 | 48 |
| T01 | Saline | 1250 | 1250 | 627 |
| T02 | *Escherichia coli* Bacterin | 1114 | 11105 | 22135 |
| T03 | QCDCR | 1250 | 12458 | 22135 |
| T04 | QCDO | 1980 | 31250 | 139281 |
| T05 | QCDX | 789 | 35057 | 62289 |
| T06 | QCDXO | 1573 | 247472 | 439702 |

The IgG2 antibody titers are shown in Table 8. This antibody isotype is often associated with better phagocytosis by neutrophils in the milk and protection for the animal. The QCDO, QCDX, and QCDXO formulations were especially effective in inducing a good immune response in these cattle.

TABLE 8

IgG2 antibody titers.

| Tmt Group | Treatment | Geometric mean IgG2 Titer to J5 at day | | |
|---|---|---|---|---|
| | | 0 | 21 | 48 |
| T01 | Saline | 199 | 396 | 396 |
| T02 | *Escherichia coli* Bacterin | 280 | 855 | 3136 |
| T03 | QCDCR | 1114 | 1402 | 4966 |
| T04 | QCDO | 558 | 1573 | 6250 |
| T05 | QCDX | 176 | 3947 | 9899 |
| T06 | QCDXO | 559 | 8824 | 87940 |

Dairy Cattle

Experimental vaccines were formulated using inactivated *E. coli* J5 bacterin as the antigen, and were made according to Example 13 above. Each treatment group initially contained seven animals (Table 9). One treatment group received saline (T01) and another group received a commercial J5 vaccine (T02-Enviracor™ Pfizer J-5 *Escherichia coli* bacterin). The other treatment groups received various formulations containing the adjuvants specified in Table 9. All vaccinations were administered by subcutaneous injection on study days 0 and 21. The dosing volume was 5 mL.

TABLE 9

Vaccine Groups - Dairy Cattle

| Tmt Group | # of Animals | Treatment | Day | Dose (ml) | Route |
|---|---|---|---|---|---|
| T01 | 7 | Saline | 0, 21 | 5.0 | SC |
| T02 | 7 | *Escherichia coli* Bacterin, J-5 strain | 0, 21 | 5.0 | SC |
| T03 | 7 | QCDCR | 0, 21 | 5.0 | SC |
| T04 | 7 | QCDO | 0, 21 | 5.0 | SC |
| T05 | 7 | TXO | 0, 21 | 5.0 | SC |

In Table 9, QC is the abbreviation for QuilA/cholesterol, D for DDA, C for carbopol, R for R1005, X for DEAE-dextran, T for TLR agonist (CpG-ODN), and O for oil. Stock solutions were prepared for the following; *E. coli* was given as about $4-5 \times 10^9$ organisms per dose as determined by direct count by light microscopy. Quil A in water at 50 mg/ml, Cholesterol in ethanol at 17 mg/ml, DDA in ethanol at 17 mg/ml, R1005 in 20 mM phosphate buffer at 5 mg/ml, DEAE-dextran in water at 200 mg/ml, TLR agonist in TE buffer at 20 mg/ml. The individual components were added v/v in the order of letter symbols from left to right. For example, QCDCR the appropriate volume of Quil A was added followed by addition of cholesterol, DDA and finally carbopol. When the formulations contained oil, the separate components were add mixed then emulsified into a mixture of Drakeol 5 LT mineral oil with either Span 80 and Tween 80 (TXO, QCDO) or Span 85 and Tween 85.

Blood Collection

Blood samples were collected on study days 0, 21 and 49 for serological testing. Antibody titers to *E. coli* J5 in serum samples were determined by means of J5-specific, indirect ELISA assay. IgG antibody isotypes were determined with sheep-anti-bovine antibody conjugates (Bethyl Labs). Titers were determined and expressed as their geometric means.

Results

The serological results of the study are shown in the Table 10. Higher antibody titers generally are associated with better protection of vaccines. The total J5-specific IgG titer is shown in Table 10. Several of the formulations of the invention produced much higher titers than the commercial product, even though these formulations had a similar amount of J5 antigen added. The QCDO, TXO and QCDXO formulations were especially effective in inducing a good immune response in these cattle.

TABLE 10

IgG antibody titers.

| Tmt Group | Treatment | Geometric mean IgG Titer to J5 at day | | |
|---|---|---|---|---|
| | | 0 | 21 | 48 |
| T01 | Saline | 50 | 60 | 110 |
| T02 | *Escherichia coli* Bacterin | 175.2 | 275 | 245 |
| T03 | QCDCR | 106.5 | 202.7 | 209 |
| T04 | QCDO | 55.9 | 328.3 | 245 |
| T05 | TXO | 90.6 | 328.3 | 889 |

The J5-specific IgG1 antibody isotypes were determined. These results are shown in Table 10. Again, QCDO, TXO and QCDXO formulations were especially effective in inducing a good immune response in these cattle. These formulations gave much higher titers with even a single vaccination than the commercial vaccine did with two injections.

This antibody isotype is often associated with better phagocytosis by neutrophils in the milk and protection for the animal. The QCDXO formulation was especially effective in inducing a good immune response in these cattle.

Example 18

Bovine Viral Diarrhea Virus Vaccine

Study Objective

This study compared the safety, efficacy and cross-protection of two killed Bovine Viral Diarrhea Virus type 1 and type 2 (BVDV-1 and BVDV-2 or BVD-1/2) vaccines and one BVDV-1 and -2 extract vaccine formulated with adjuvants of the invention with one negative (saline) and two positive controls (a modified live BVDV-2 vaccine, and a currently available killed BVDV-1/2 vaccine) against a challenge with BVDV-1 in naïve calves. Table 11 presents the Study Design.

This study also showed that the adjuvants of the invention can be used to distinguish animals vaccinated with vaccine compositions of the present invention from animals naturally exposed to BVDV.

Animals

Healthy weaned beef cattle of either sex between 7 and 15 months of age that were seronegative for BVDV-1 and BVDV-2 were used.

TABLE 11

Study Design

| Gp | Vaccine | Adjuvant | Dose | Days | # Animals | Challenge day | Route | Dose |
|---|---|---|---|---|---|---|---|---|
| T01 | Saline | None | 2 mL, SC left neck | 0 & 21 | 10 | 42 | IN | 5 mL |
| T02 | BVD-2 MLV | None | 2 mL, SC left neck | 0 | 10 | 42 | IN | 5 mL |
| T03 | BVD-1/2 inactive | PreZent-A | 2 mL, SC left neck | 0 & 21 | 10 | 42 | IN | 5 mL |
| T04 | BVD-1/2 inactive | QCDC | 2 mL, SC left neck | 0 & 21 | 10 | 42 | IN | 5 mL |
| T05 | BVD-1/2 inactive | QCDCR | 2 mL, SC left neck | 0 & 21 | 10 | 42 | IN | 5 mL |
| T06 | BVD-1/2 inactive extract | QCDC | 2 mL, SC left neck | 0 & 21 | 10 | 42 | IN | 5 mL |

QC is the abbreviation for QuilA/cholesterol, D for DDA, C for Carbopol®, R for Bay R1005®

Vaccination

On Study Days 0 and 21, animals (N=10/group) were vaccinated as described in Table 11. The antigen (BVDV) was given as 5,500 Relative Potency Units (RU) per dose as determined by ELISA assay. Calves in the T01 group served as the control group. They were given a 0.9% sodium chloride sterile solution. Those in the T02 through T06 groups received experimental BVDV 1/2 vaccines with the adjuvant as shown in Table 11. The T02 group received only one vaccination (Study Day 0). They received a modified live virus (MLV) BVDV-2 vaccine that contained no adjuvant. Group T03 received a killed virus BVDV-1/2 vaccine containing a 2.5% oil-in-water emulsion (Amphigen) and Quil A/cholesterol adjuvants (PreZent AC)). Group T04 received a killed virus BVDV-1/2 vaccine containing Quil A/cholesterol, DDA, and Carbopol. Group T05 received a killed virus BVDV-1/2 vaccine containing Quil A/cholesterol, DDA, Carbopol, and R1005. Group T06 received a killed virus BVDV-1/2, high-titer extract vaccine containing Quil A cholesterol, DDA, and Carbopol on Day 0, and a similar low-titer extract vaccine on Day 21. All treatments were administered subcutaneously in a single 2 mL dose on Days 0 and 21, with the exception of Group 2.

The QCDC+/-R contained 100 μg Quil A, 100 μg Cholesterol, 50 μg DDA, and 0.075% Carbopol and where included 1,000 μg R1005 all per 2 mL dose as previously described.

Challenge

On Day 42 all the animals were challenged intranasally with about 4 mL (approximately 2 mL per nostril) of noncytopathic BVDV-1 strain (Strain NY-1; CVB, USDA, Ames, Iowa) with a concentration 5.4 $\log^{10}$ TCID$_{50}$ per 5-mL dose.

Observations

Injection site observations were recorded on Study Days 0 (pre-vaccination), 1, 2, 3, 7 and 21 for the first injection site (left neck). Observations for the second injection site (also left neck) were recorded on Study Days 21 (pre-vaccination), 22, 23, 24, 28 and 35. All palpable injection site reactions were measured (L×W×H, cm). Rectal Temperatures were recorded on Study Days -1, 0 (pre-vaccination), 1, 2 and 3 for the primary vaccination. Temperatures for the booster vaccination were recorded on Study Days 20, 21 (pre-vaccination), 22, 23 and 24.

Blood Sampling

Blood samples were collected from each available animal using serum separation tubes (SST) on Study Days -1, 20, 34 and 49. Blood samples were collected using EDTA tubes on Study Days 33 through 35 (pre-challenge) and 36 through 49. Blood samples were collected using cell preparation tubes (CPT) on Study Days 34 (pre-challenge) and 36 through 49.

Results

Table 12 shows geometric least squares mean (GLSM) serum neutralizing antibody titer to BVD virus by hemeagglutination assay on day of study. The results show the adjuvants of the invention provided an increase in titers against both BVDV-1 and BVDV-2 as the study progresses. An acceptable titer for the UDSA is above a titer of 8. These data demonstrate titers above 5,000 which indicate strong antibody production that is capable of stopping live virus when it enters the animal with the potential for infection and disease.

TABLE 12 serum antibody neutralizing titer

| Group (vaccine, adjuvant) | BVDV-1 | | | | BVDV-2 | | | |
|---|---|---|---|---|---|---|---|---|
| | Day -1 Means | Day 21 GLSM | Day 41 GLSM | Day 56 GLSM | Day -1 Means | Day 21 GLSM* | Day 41 GLSM* | Day 56 GLSM* |
| Group T01 (saline, none) | 1.00 (1-1) | 1.00 (1-1) | 1.00 (1-1) | 21.38 (11-54) | 1.00 (1-1) | 1.01 (1-1) | 1.01 (1-1) | 371.98 (128-861) |
| Group T02 (BVDV-2 MLV, none) | 1.00 (1-1) | 1.00 (1-1) | 2.75 (1-27) | 13.27 (1-45) | 1.00 (1-1) | 2.14 (1-10) | 45.21 (1-1024) | 454.09 (91-1218) |
| Group T03 (BVDV-1/2, PreZent-A) | 1.00 (1-1) | 1.60 (1-6) | 35.59 (1-181) | 486.49 (91-2048) | 1.00 (1-1) | 6.40 (1-38) | 877.75 (38-3444) | 8950.83 (1024-77936) |

TABLE 12-continued

| | serum antibody neutralizing titer | | | | | | | |
|---|---|---|---|---|---|---|---|---|
| Group | BVDV-1 | | | | BVDV-2 | | | |
| (vaccine, adjuvant) | Day −1 Means | Day 21 GLSM | Day 41 GLSM | Day 56 GLSM | Day −1 Means | Day 21 GLSM* | Day 41 GLSM* | Day 56 GLSM* |
| Group T04 (BVDV-1/2, QCDC) | 1.00 (1-1) | 1.20 (1-3) | 12.66 (5-91) | 1772.17 (512-16384) | 1.00 (1-1) | 8.71 (5-16) | 329.56 (54-861) | 11611.44 (4096-16384) |
| Group T05 (BVDV-1/2, QCDCR) | 1.00 (1-1) | 1.12 (1-3) | 18.92 (5-91) | 2477.87 (861-6889) | 1.00 (1-1) | 5.30 (2-13) | 692.34 (152-2048) | 10517.89 (3444-46341) |
| Group T06 (BVDV-1/2 extract, QCDC) | 1.00 (1-1) | 1.07 (1-2) | 4.60 (1-23) | 922.95 (256-4096) | 1.00 (1-1) | 2.43 (1-7) | 239.87 (64-1448) | 9956.50 (4096-55109) |

Table 13 presents leucopenia data for study days 43-56. The leukopenia results on day of study demonstrate that the MLV vaccine (T02) prevented infection by that specific virus of the challenge. A measure of leukopenia is a criteria for licensing a MLV product by the USDA. However, for an inactivated virus leucopenia is not a criteria by the USDA but as the data suggests the adjuvants of the invention had leucopenia in up to only 20% of the animals where as most inactivated virus vaccines have 100% leucopenia. This indicates that the adjuvants of the invention were able to drive a strong Th1 response with an inactivated antigen. This is difficult to do and is seldom seen in inactivated products.

TABLE 13

| | Leucopenia by Day of Study. | | | | | |
|---|---|---|---|---|---|---|
| Day of study | T01 Saline | T02 Modified Live | T03 PreZent A | T04 QCDC | T05 QCDCR | T06 QCDC Extract |
| Day 43 | 0 | 0 | 0 | 0 | 0 | 0 |
| Day 44 | 0 | 0 | 0 | 0 | 0 | 0 |
| Day 45 | 0 | 0 | 0 | 0 | 0 | 0 |
| Day 46 | 2 | 0 | 0 | 0 | 0 | 0 |
| Day 47 | 5 | 0 | 1 | 1 | 1 | 3 |
| Day 48 | 5 | 0 | 1 | 2 | 2 | 3 |
| Day 49 | 8 | 0 | 1 | 2 | 2 | 6 |
| Day 50 | 8 | 0 | 1 | 0 | 1 | 3 |
| Day 51 | 6 | 0 | 0 | 0 | 0 | 0 |
| Day 52 | 2 | 0 | 0 | 0 | 0 | 0 |
| Day 53 | 2 | 0 | 0 | 0 | 0 | 0 |
| Day 54 | 2 | 0 | 0 | 0 | 0 | 0 |
| Day 55 | 2 | 0 | 0 | 0 | 0 | 0 |
| Day 56 | 2 | 0 | 0 | 0 | 0 | 0 |

Table 14 presents the Serum Neutralization Titers on Day 41 (20 Days after Second Vaccination, Pre-Challenge). Modified live virus is capable of only developing antibody responses to the exact virus in the vaccine. This is seen in that Group T02 shows protection against only BVDV-2. However, the T03 (PreZent-A), T04 (QCDC), and T05 (QCDCR) adjuvanted inactivated vaccines generated a strong antibody response early on in the onset of immunity and throughout the in life phase of the animal study toward a serologically diverse panel of BVDVs. This shows that these adjuvants have the ability to provide safety and efficacy in a challenge model to protect cattle in not only a homologous but a heterologous challenge.

TABLE 14

Serum Neutralization Titers on Day 41.
Cross Protection by Serological TiterTreatment group,
Antibody Titer Log 2

| | T01 Saline | T02 Modified Live | T03 PreZent A | T04 QCDC | T05 QCDCR | T06 QCDC Extract |
|---|---|---|---|---|---|---|
| Average BVDV1a | <1 | 0.8 | 4.0 | 2.5 | 2.9 | 1.9 |
| Average BVDV1b | <1 | 0.7 | 3.9 | 2.4 | 2.9 | 1.5 |
| Average BVDV2 | <1 | 4.5 | 8.8 | 8.1 | 8.0 | 6.5 |

Marker Activity. Presented herein are data which show that the adjuvants of the invention can be used to distinguish animals vaccinated with vaccine compositions of the present invention from animals naturally exposed to BVDV. This can be seen by determining the antibody profile differences between structural and non structural gene products of the virus. The marker activity is demonstrated by the gel run by radioimmunoprecipitation assay (FIG. 1). An antibody response to the NS2/3 and E2 proteins of the BVDV is very pronounced in an animal vaccinated with a MLV vaccine or an animal naturally exposed to BVDV or PreZent-A adjuvanted inactivated vaccine. However, the adjuvants of the invention demonstrated an antibody response to only E2 protein and not the NS2/3 proteins. Thus an animal vaccinated with an inactivated BVDV vaccine comprising adjuvants of the invention can be differentiated between from either a naturally infected animal or a MLV vaccinated animal or PreZent-A vaccinated animal. This would be considered a marker-vaccine that is valuable for eradication of these types of diseases in animal populations.

Example 19

*Mycoplasma hyopneumonia* in Swine

Background

*Mycoplasmal pneumonia* of swine (MPS) or enzootic pneumonia is a widespread, chronic disease characterized by coughing, growth retardation, and reduced feed efficiency. The etiologic agent is *M. hyopneumoniae*; however, the naturally occurring disease often results from a combination of bacterial and mycoplasmal infections.

MPS causes considerable economic loss in all areas where swine are raised. Surveys conducted at various locations throughout the world indicate that lesions typical of those seen with MPS occur in 30%-80% of slaughter-weight swine. Because mycoplasmal lesions may resolve before hogs reach slaughter weight, the actual incidence may be higher. The prevalence of *M. hyopneumoniae* infection in chronic swine pneumonia has been reported to range from 25%-93%. Pigs of all ages are susceptible to MPS, but the disease is most common in growing and finishing swine. Current evidence indicates that *M. hyopneumoniae* is transmitted by aerosol or direct contact with respiratory tract secretions from infected swine. Transmission from sow to pig during lactation is possible. Once established, MPS occurs year after year in infected herds, varying in severity with such environmental factors as season, ventilation, and concentration of swine.

Study Objective

To compare the efficacy of *Mycoplasma hyopneumoniae* vaccines formulated with novel adjuvants of the invention against the efficacy of an experimental serial of a commercially available *Mycoplasma hyopneumoniae* bacterin following intratracheal challenge with a virulent *M. hyopneumoniae* lung homogenate.

Animals

Sixty-six (66) clinically healthy, crossbred pigs at approximately 17 days of age without a history of disease caused by *M. hyopneumoniae* and PRRSV, or vaccination against the same organisms were used in the study. Prior to shipment to the study site, and for 2 days post-arrival, pigs were treated with Naxcel® intramuscularly in the hind leg, as per label directions, to prevent stress-related disease such as *Streptococcus suis*. Animals were allocated to treatments and pens according to a randomization plan. The study design is shown in Table 15.

TABLE 15

Experimental Design

| Treatment Group | Treatment | No. of Animals | Vaccination | Route | Challenge |
|---|---|---|---|---|---|
| T01 | Negative Control 63464-70 | 12 | Day 0 Day 14 | Intramuscular | *M. hyo* lung-homogenate |
| T02 | DDA/Carbopol/R1005 (DCR) | 12 | Day 0 Day 14 | Intramuscular | *M. hyo* lung-homogenate |
| T03 | QAC/DDA/Carbopol (QCDC) | 12 | Day 0 Day 14 | Intramuscular | *M. hyo* lung-homogenate |
| T04 | QAC/DDA/Carbopol/R1005 (QCDCR) | 12 | Day 0 Day 14 | Intramuscular | *M. hyo* lung-homogenate |
| T05 | *M. hyo* Bacterin | 12 | Day 0 Day 14 | Intramuscular | *M. hyo* lung-homogenate |
| NTX | None | 6 | N/A | N/A | N/A |

QAC is the abbreviation for QuilA/cholesterol,

Investigational Veterinary Products (IVP)

The antigens and Investigational Veterinary Products (IVP) are shown in Table 16. The vaccines for Treatment Groups T02, T03, and T04 (all except T05) were prepared according to Example 13 by using the concentrations of components shown in Table 16 below. The components were added in the order listed in the table.

A saline extender was added to a vessel and homogenization was initiated and continued throughout the preparation procedure. Inactivated *M. hyopneumoniae* was prepared from a blended volume of 75 liters of fermentate per 800 liters of final formulated product and was added to a concentration of 0.09375 ml per dose. Quil A was added to the concentration listed in Table 16. Cholesterol/Ethanol solution was then added. DDA/ethanol solution was added, followed by the addition of the Bay R1005 glycolipid solution. Carbopol was then added and the solution was brought to the final volume with the saline extender.

The vaccine for Treatment Group T05 (Amphigen Based Vaccine formulation) was the commercially available product Respisure® (Pfizer, Inc).

TABLE 16

Investigational Veterinary Products (IVP)

| IVP | Treatment Group | Antigen Dose | Adjuvant per Dose | # of Doses | Volume/ Dose |
|---|---|---|---|---|---|
| Negative Control Saline | T01 | N/A | N/A | 24 | 2 mL |
| DDA/Carbopol/ R1005 | T02 | *M. hyo* | Mhyo + DDA/R1005/Carbopol (50/1000ug/dose/0.075% w/v) | 24 | 2 mL |

TABLE 16-continued

Investigational Veterinary Products (IVP)

| IVP | Treatment Group | Antigen Dose | Adjuvant per Dose | # of Doses | Volume/ Dose |
|---|---|---|---|---|---|
| QAC/DDA/ Carbopol | T03 | M. hyo | Mhyo + QuilA/cholesterol/DDA/ Carbopol (100/100/50 micrograms/ dose/0.075% v/v) | 24 | 2 mL |
| QAC/DDA/ Carbopol/R1005 | T04 | M. hyo | Mhyo + QuilA/cholesterol/DDA/ Carbopol/R1005 adjuvant diluent (100/100/50micrograms/dose/ 0.075% v/v/1000ug/dose) | 24 | 2 mL |
| M. hyo Bacterin | T05 | M. hyo | 5% Amphigen | 24 | 2 mL |

Vaccination

Animals in the NTX treatment group were not vaccinated or challenged. At approximately 3 weeks of age (Day 0—right neck) and 5 weeks of age (Day 14—left neck), animals in T01, T02, T03, T04 and T05 were vaccinated intramuscularly, 2 mL per dose, by a qualified individual blinded to treatment group.

Challenge Material

Animals in T01 through T05 were challenged intratracheally 3 weeks following the second vaccination (at approximately 8 weeks of age—Study Day 35). Animals were challenged with a 5 mL dose of a 1:50 dilution in Friis medium of a 10% frozen lung homogenate of M. hyo strain 11 (LI36).

Blood Sampling

On Day −1 or 0 (prior to 1st vaccination), Day 13 or 14 (prior to 2nd vaccination), Day 34 or 35 (prior to challenge) and Day 63 (at necropsy), blood samples (approximately 5 to 10 mL in serum separator tubes) were collected from all pigs and tested for M. hyopneumoniae serology (ELISA—IDEXX).

Weight

All animals were weighed on arrival for allotment purposes, on Day 34 or 35 (prior to challenge), and on Day 62 or 63 (prior to necropsy).

Necropsy

On Day 63, all surviving animals were euthanized according to site-specific procedures. Lungs were evaluated grossly for characteristic lesions attributable to a M. hyopneumoniae infection and were given a score for the lesions attributed to the M. hyopneumoniae challenge. Lung lesions scores were recorded as the percent of lung lesions for each lung lobe. The percentage of consolidation for each lobe (left cranial, left middle, left caudal, right cranial, right middle, right caudal, and accessory were scored as an actual value between 0-100%. The percent for each lung lobe was used in a weighted formula for calculation of the total percent lung with lesions. Six (6) NTX animals were necropsied on Day 34 or 35 prior to challenge and their lungs scored for lesions.

Lung Lesion Scores

Percentage of total lung with lesions were calculated using the following formula: Percentage of total lung with lesions=100×{(0.10×left cranial)+(0.10×left middle)+(0.25×left caudal)+(0.10×right cranial)+(0.10×right middle)+(0.25×right caudal)+(0.10×accessory)}. The arcsine square root transformation was applied to the percentage of total lung with lesions prior to analysis. The transformed lung lesions were analyzed with a general linear mixed model. Linear combinations of the parameter estimates were used in a priori contrasts after testing for treatment effect. Back transformed least squares means of a significant (P 0.10) percentage of total lung with lesions, their standard errors, and their 90% confidence intervals were calculated as well as the minimums and maximums.

Results

As indicated by the results Table 17 below, the adjuvants of the invention performed equally as well as the oil adjuvanted treatment group T05 that contained the adjuvant Amphigen®. Typically a lung lesion score of under 3 is considered to have conferred efficacy by the vaccine treatment. The combinations of the adjuvants of the invention all met this criteria and QCDCR performed the best in score and range among individual animals.

TABLE 17

Percent Lung with Lesions

| | Signal:Positive (S/P) Serological Ratio Day 34 | LSM | Range |
|---|---|---|---|
| T01 - Placebo | 0.00 | 8.4 | 0-25.55 |
| T02 - DRC | 0.28 | 2.4 | 0-20.13 |
| T03 - QCDC | 0.15 | 2.1 | 0-23.18 |
| T04 QCDCR | 0.23 | 0.5 | 0-2.7 |
| T05 - RespiSure | 0.46 | 0.6 | 0-2.33 |

N = 12 per group, with the exception of T05 where N = 11

Example 20

Feline Avian Influenza Virus (FAIV)

This study evaluated the efficacy in cats of an influenza vaccine using an adjuvant of the invention by challenge with a virulent avian influenza virus strain.

Methods and Results

Prior to vaccination, animals were determined to be negative for both influenza virus and antibodies to influenza virus, based respectively on oropharyngeal swabs and serum blood sample analysis taken prior to vaccination.

Experimental vaccines were formulated using inactivated pathogenic avian influenza and purified hemagglutinin (HA). Each treatment group initially contained six animals (Table 18). Two treatment groups received the experimental FAIV vaccines (T01 vaccine antigen was purified H5 HA protein; and T02 vaccine antigen was inactivated $H_5N_2$ strain), one treatment group received an inactivated modified $H_5N_1$ virus strain vaccine (T03), one placebo control group received an adjuvant-only vaccine (T04) and one negative control group receiving saline only (T05). All vaccinations were administered by subcutaneous injection on study days 0 and 21. The dosing volume was 1 mL. Following vaccination animals were observed constantly until they recovered and were able to sit upright to ensure there were no adverse reactions. Observations at approximately one hour post vaccination were recorded and any other complication observed following vaccination would have been recorded.

The adjuvant composition was previously described above by the example QCDC using Quil A (20 µg), Cholesterol, (20 µg), DDA (10 µg) and Carbopol (0.05%) per dose. Antigen is inactivated whole virus or purified H5 HA protein.

Animals were assessed for injection site reactions and serological response to the vaccine. Three animals (two in T02-inactivated $H_5N_2$, and one in T05-saline) were euthanized due to congenital hyperoxaluria before challenge. On study day 49, all surviving cats were challenged via the intratracheal route with strain $H_5N_1$ A/Vietnam/1194/04 to evaluate efficacy of the vaccine candidates. Animals were challenged with 5.0 mL of material containing $10^5 TCID_{50}$, which was released just above the bifurcation using a small catheter that was brought into the trachea using a tracheoscope. Animals were observed and sampled for five days after challenge. At the end of the animal phase (study day 54), all surviving animals were euthanized and a necropsy performed on each.

TABLE 18

Vaccine Groups

| Treatment Group | Vaccine | Dose | Route of Administration | Study Day | Animals |
|---|---|---|---|---|---|
| T01 | Purified recombinant haemaglutinin (HA) protein vaccine (25,600 HA units/dose) | 1.0 mL | Subcutaneous | 0 and 21 | 6 |
| T02 | Inactivated modified H5N2 virus vaccine (25,600 HA units/dose) | 1.0 mL | Subcutaneous | 0 and 21 | 6 |
| T03 | Inactivated modified H5N1 virus vaccine (25,600 HA units/dose) | 1.0 mL | Subcutaneous | 0 and 21 | 6 |
| T04 | Placebo - Adjuvant only | 1.0 mL | Subcutaneous | 0 and 21 | 6 |
| T05 | Placebo - Saline only | 1.0 mL | Subcutaneous | 0 and 21 | 6 |

Blood samples were collected on study days −14 pre-vaccination, 0, 21 and 49 for serological testing. On study days 49 and 54, blood samples were collected for virological testing. On study day 42, an unscheduled blood sample was taken from all surviving animals to test kidney function on sera before challenge.

Oropharyngeal swabs were collected from all the animals on study days −14, 49 prior to challenge and 50 through to 54. Rectal swabs were collected from all the animals on study days 49 prior to challenge and days 50 through 54. The collection of the swabs was done just prior to challenge on study day 49.

During necropsy, all lung lobes were aseptically removed, weighed and evaluated grossly for characteristic lesions attributable to FAIV infection. Percentages were used to identify the extent of lung consolidation. The left lung was fixed with 10% neutral-buffered formalin for histopathology. The right lung was collected and sampled for virological testing. In addition to the lungs a kidney sample and any tissues with gross pathology were also sampled and stored in 10% neutral-buffered formalin for histopathology.

Viral titres in blood samples, oropharyngeal and rectal swabs, and in lung tissue samples were determined by means of a H5N1-specific TaqMan PCR. Briefly, RNA was isolated using a MagnaPure LC system with the MagnaPure LC Total nucleic acid isolation kit (Roche Diagnostics; Almere, The Netherlands), and influenza A virus was detected by using a real-time RT-PCR assay. Data were expressed as Control Dilution Units (CDU). CDU's were determined from a standard curve produced from a stock of virus, which was serially diluted, with each dilution undergoing nucleic acid extraction and TaqMan PCR amplification in the same manner as test samples.

RT-PCR positive oropharyngeal swabs and lung tissue samples were also analysed by virus isolation and titration on Madine Darby canine kidney (MDCK) cells. Results were expressed as $log_{10}$ 50% tissue culture infective doses per milliliter or gram of sample ($log_{10}$ $TCID_{50}$/mL or $log_{10}TCID_{50}$/g).

Plasma samples were analysed by virus neutralisation and by hemagglutination inhibition. For the hemagglutination inhibition (HI) assay, a virus suspension of influenza strain Vietnam 1194/04 (H5N1, clade 1) or Indonesia 05/2005 (H5N1, clade 2) was incubated with serial (2-fold) dilutions of serum sample pre-treated with cholerafiltrate (obtained from *Vibrio cholerae* cultures). Subsequently, erythrocytes were added to the dilutions and after incubation the maximum dilution of the agents showing complete inhibition of haemagglutination was defined as the titre of HI.

The virus neutralization (VN) assay was based on an endpoint titration of the sera. Briefly, a constant amount of virus was mixed with a serial (2-fold) dilution of a serum sample. Virus neutralization was read using MDCK cells as indicator cells and was visualized by erythrocyte agglutination. VN titres were scored by taking the highest dilution of serum in which 50% of the inoculated cell cultures showed erythrocyte agglutination.

The left lung was collected at necropsy and fixed with 10% neutral-buffered formalin for histopathology. After fixation, the tissues was embedded in paraffin, tissue sections were prepared and stained with haematoxylin and eosin for histological examination. Description and degree of pathological changes observed were recorded.

Results

None of the animals in the five treatment groups showed any pain or swelling at the injection site following the first and second vaccination. Furthermore, no skin abnormalities were recorded at the injection sites. Following vaccinations and before challenge, there were no significant differences at the 0.1 significance level in body temperatures between treatments by linear mixed model analysis. One T01 animal was febrile 40° C.) before the first vaccination on Day 0 and for several days after. Sporadic body temperature increases in individual animals to 40° C. or above were recorded after vaccinations (Days 0 and 21). No abnormal health related to vaccination was observed during the study. Three animals (two in T02-H5N2, and one in T05-saline) were euthanized due to congenital hyperoxaluria before challenge. Several animals from all treatments presented with wound complications following the implantation of the temperature recorder. No concurrent treatments were administered from day 0 until study completion.

Vaccinated T01, T02 and T03 animals showed less clinical signs and no mortality after challenge compared to control T04 and T05 animals. In T01, one animal showed depression and increased respiratory effort two days after challenge. None of the remaining five T01 animals showed any abnormal health after challenge. In T02 (n=4) and T03 (n=6), all animals remained healthy following challenge. In T04 (n=6) the first abnormal clinical signs (depression and increased respiratory effort) were seen in two animals two days after challenge. Three days after challenge, all six animals in T04 were depressed and showed an increase in respiratory effort. Consequently two animals had to be euthanized for welfare reasons. Four days after challenge (Day 53), one animal was found dead and the remaining three T04 animals exhibited depression, increased respiratory effort, third eyelid protrusion and nasal discharge, and were euthanized for welfare reasons. In T05 (n=5), the first abnormal clinical signs of depression and increased respiratory effort were seen in one animal one day after challenge. Two days after challenge, two more animals started to show those signs. Three days after challenge, one animal was found dead and the remaining four animals exhibited depression, increased respiratory effort and third eyelid protrusion. One animal was subsequently euthanized for welfare reasons. Four days after challenge, the respiratory effort had worsened in one of the three remaining animals and another animal additionally showed nasal discharge. All three remaining animals were euthanized for welfare reasons four days after challenge (Day 53).

Following challenge, mean body temperatures remained below 40.0° C. in vaccinated animals (T01, T02, and T03). Mean temperatures of control animals (T04 and T05) rose≥40.0° C. starting one day after challenge. Differences in mean body temperatures between treatments were significant (p=0.0001) by linear mixed model analysis. Individual animal data showed that in a minority of T01, T02 and T03 animals, body temperatures rose to 40.0° C. and above at sporadic time points on Day 53. In T01, two animals were febrile (range 40.0 to 40.1° C.) at one time point. In T02, two animals were febrile (range 40.0 to 40.3° C.) at one and three time points, respectively. In T03, one animal was febrile (range 40.0 to 40.3° C.) at three time points. In T04 and T05 all animals were febrile for at least twelve hours between Days 50 to 51.

HI antibody titres to influenza strains Vietnam 1194/04 (H5N1, clade 1) and Indonesia 05/2005 (H5N1, clade 2) were determined before the first and second vaccination and before challenge. The lower limit of detection was 5. Prior to vaccination, the titers in all 5 treatment groups were below the lower limit of 5. Following vaccination all vaccinated (T01, T02, and T03) animals developed HI antibody titres above 5 and showed at least a six-fold increase in titres compared to pre-vaccination values. In T01 and T03, titres against Vietnam 1194/04 ranged from 20 to 160 following the first vaccination, and 140 to 960 following the second vaccination. In T02, titres against Vietnam 1194/04 were lower than those seen in T01 and T03, ranging from 5 to 30 following the first vaccination, and 5 to 70 following the second vaccination. HI antibody titres against Indonesia 05/2005 were similar to those against Vietnam 1194/04.

Plasma samples taken before and after challenge were tested by H5N1-specific real time RT-PCR for viral load. All animals had virus negative samples before challenge. After challenge, no virus was detected in the plasma of T01 and T03 animals. In contrast, 25% (1 of 4) of T02 animals, 67% (4 of 6) of T04 animals and 60% (3 of 5) of T05 animals were virus positive in plasma after challenge. Differences between treatments were significant (p=0.0247) by linear mixed model analysis.

Virus shedding after challenge was assessed in throat swab samples by real time RT-PCR and virus titration, and in rectal swab samples by real time RT-PCR. No viral shedding from the throat was detected in T01 animals after challenge. In T02, all four animals (100%) shed virus at one point after challenge. In T03, in total two of six animals (33%) shed virus after challenge. In T04, three of six animals (50%) shed virus after challenge. In T05, four of five animals (80%) shed virus after challenge. No samples were taken from T04 and T05 animals five days after challenge, since all animals were deceased by then. For the purpose of statistical analysis, however, animals that died or were euthanized before the last day of study had their last test results carried forward to the last day of study.

Throat samples with a RT-PCR positive result (≥1.8 CDU) were also used in virus titration assays. Virus titration confirmed that all RT-PCR positive samples contained infectious influenza virus (data not shown). Infectious virus titres were lower in vaccinated animals (T02 and T03) than control animals (T04 and T05). These differences were significant three days after challenge when comparing T02 or T03 with T04, and three, four and five days after challenge when comparing T02 or T03 with T05. Titres in T02 and T03 animals were 0.5 $\log_{10}$ $TCID_{50}$. Titres seen in T04 ranged from 2.3 to 4.3 $\log_{10}$ $TCID_{50}$. Titres seen in T05 ranged from 1.5 to 3.8 $\log_{10}$ $TCID_{50}$.

Shedding in feces as assessed by rectal swabs was detected in all treatment groups except T02 three or four days post challenge. Virus quantities detected by RT-PCR were between 2.2 to 2.3 $\log_{10}$ CDU in T01, 3.2 $\log_{10}$ CDU in T03, 2.0 to 2.7 $\log_{10}$ CDU in T04, and 2.2 $\log_{10}$ CDU in T05. There were no significant differences at the 0.1 significance level between treatments on any of the days after challenge.

Lung pathology was less severe in vaccinated (T01, T02, and T03) than in control animals (T04 and T05). All vaccinated animals presented with a mild, multifocal, subacute bronchointerstitial pneumonia. Control animals showed either a moderate (two T04 animals and one T05 animal) or severe (four T04 and four T05 animals), subacute bronchointerstitial pneumonia with a multifocal distribution in all except two control animals who (one T04 and one T05 animal) showed a diffuse distribution. Whole lung was assessed for the extent of consolidation, which was expressed in percentage consolidation of total lung tissue. In agreement with the lung pathology findings, percentage consolidation was significantly lower in vaccinated animals (T01, T02, and T03) than in control animals (T04 and T05).

Viral load in lung tissue collected at the time of death or euthanasia was assessed by virus titration and H5N1 RT-PCR. Lung tissue from vaccinated animals (T01, T02 and T03) had significantly lower mean virus titres than those from controls (T04 and T05). There were no significant differences between mean titres in lung tissue from vaccinated animals (T01, T02 and T03). Analysis by RT-PCR yielded the same results.

Following challenge with a highly pathogenic H5N1 avian influenza strain, clinical signs including fever, mortalities, viraemia, viral shedding from throat and in feces, viral infection of the lung and lung pathology, including consolidation, were observed in control animals which had received either adjuvant (T04) or saline (T05).

Vaccination with purified H5 HA protein (T01) prevented viraemia, viral shedding from the throat, and mortality in six young cats following challenge with a highly pathogenic H5N1 avian influenza strain. Furthermore, vaccination with purified H5 HA protein (T01) reduced clinical signs, including fever, viral load in lung and lung pathology, including consolidation.

Vaccination with an inactivated $H_5N_2$ strain (T02) prevented clinical signs, viral shedding in feces, and mortality in four young cats following challenge with a highly pathogenic H5N1 avian influenza strain. Furthermore, vaccination with the inactivated H5N2 strain (T02) reduced viraemia, fever, viral shedding from the throat, viral load in lung and lung pathology, including consolidation.

Vaccination with an inactivated H5N1 strain (T03) prevented clinical signs, viraemia and mortality in six young cats following challenge with a highly pathogenic H5N1 avian influenza strain. Furthermore, vaccination with the inactivated H5N1 strain (T03) reduced fever, viral shedding from the throat, viral load in lung and lung pathology, including consolidation.

SUMMARY

No injection site reactions were observed with the vaccines formulated with either inactivated or purified HA antigen with QC/DC adjuvant. The vaccines provided a complete protection of clinical disease and mortality in vaccinated cats, significantly reduced virus load in blood and tissues, and significantly reduced virus shedding.

Example 21

Cancer

BACKGROUND

This study was conducted in immunodeficient and immunocompetent rats using human and rat hepatocellular carcinoma cells to generate heterotopic and orthotopic models.

Animals

Nude (Crl: NIH-rnu) male rats 6-8 weeks old were purchased from Charles River (Wilmington Mass.). The rats were pair housed in polycarbonate micro-isolator cages and provided ad libitum reverse osmosis water and irradiated standard rat chow; all water and bedding was autoclaved. Body weights were recorded twice weekly; animals were maintained for approximately 7 weeks and euthanized by $CO_2$ inhalation at the end of the experiment.

The experimental design incorporated two phases. In phase I, rats were randomized to two groups based on their body weight. Rats in group 1 received no tumor cell injection, while rats in group 2 received subcutaneous injection of tumor cells. At three weeks following tumor injection, rats in group 2 were randomized (based on tumor size and take-rate—see Table 19) to two groups for Phase II, one of which included two subgroups: 1) non-tumor bearing controls which received saline (the Control Group); 2) tumor bearing controls treated with adjuvant only (the Tumor Group); and 3) tumor bearing subjects (Tumor Treated) dosed with vaccine (two subcutaneous injections two weeks apart). All animals were necropsied at 14 days post the second vaccine administration.

Vaccine

Vaccine was administered by subcutaneous injection at 0.2 ml per dose.

TABLE 19

Vaccine groups

| Treatment Group | Description | Number of Animals | Tumor Cell Types (antigen) | Formulation | # of Vaccinations | Dose/route |
|---|---|---|---|---|---|---|
| Control NonTumor | Negative Control (saline) | 5 | NA | 0.63% PBS placebo | 2 | 0.2 ml/SC |
| Tumor (vehicle) | Vehicle with no antigen | 5 | QCDC | 0.63% PBS placebo | 2 | 0.2 ml/SC |
| Tumor (treated) | Homogenized liquid dose - vehicle plus HepG2 | 5 | QCDCR and 100 ug inactivated antigen | 0.63% PBS placebo | 2 | 0.2 ml/SC |

QC is the abbreviation for QuilA/cholesterol, D for DDA, C for Carbopol ®, R for Bay R1005 ®, PBS for phosphate buffered saline Vaccine Preparation Vaccines were prepared using Quil-A (20 ug/dose), Cholesterol (20 ug/dose), DDA (10 ug/dose), Carbopol (0.05%) with or without glycolipid Bay R1005® (1,000 ug/dose) and antigen. The composition was blended using a homogenizer and added in the order of addition as stated above.

Antigen Preparation

HepG2 cells (clone HB-8065) were obtained from the American Type Culture Collection (ATCC, Manassas, Va.). HepG2 is a perpetual cell line which was derived from the liver tissue of a 15 year old Caucasian male with a well differentiated hepatocellular carcinoma. Cells were expanded under standard cell culture conditions, and prepared for injection at a concentration of $1\times10^7$ cells/ml in Matrigel. Each rat was injected with 0.5 ml of cell suspension, subcutaneously at the site of the second teat.

Measurements

Tumor size was measured twice weekly throughout the study by the caliper method where volume in $cm^3=\{[(W(mm)\times W(mm)]/2\times L(mm)\}/1000$. Blood was collected by retro-orbital bleed for serum chemistry and biomarker measurements. Animals were lightly anesthetized during the bleed procedure with $CO_2/O_2$. Chemistry endpoints were analyzed using a Hitachi 917 auto analyzer (Roche, Indianapolis, Ind.). Terminal blood was taken under $CO_2$ anesthesia by cardiac puncture. Serum endpoints were evaluated using commercial ELISA assays: Alpha-Feto Protein (R & D Systems, Minneapolis Minn.) and Human Albumin (Bethyl Laboratories, Montgomery Tex.). Animals were euthanized by $CO_2$ inhalation. Tumors were excised, weighed and placed in formalin for histology.

Student's unpaired T-test was used to compare various parameters between treated and control group rats. All values are expressed as mean±SD, and a p value <0.05 was considered to be statistically significant Results Measurements of body weight were corrected by subtracting tumor weight (based on volume data and the assumption that 1 $cm^3$=1 g). Data were analyzed two ways: by treatment group, and by tumor or non-tumor bearing animals. When comparing bodyweights in tumor bearing animals to non-tumor bearing animals, there was a significant difference between the groups at the terminal time point; there was no difference at baseline. Even though body weights were not significantly different when comparing by treatment group probably due to short study duration, there was an appreciable trend towards decreased body weight in both tumor bearing groups relative to controls and a positive trend towards recovery in animals receiving vaccine when comparing the tumor bearing animals receiving vehicle with no antigen (Table 20). Also, there was also a reasonable correlation between percent change in bodyweight over the duration of the experiment and tumor volume ($r^2$=0.72) or weight (excised) at termination ($r^2$=0.73).

TABLE 20

Change in body weight over time between experimental groups.

| | Body weight (g) | | |
|---|---|---|---|
| Day | Control | Tumor | Tumor Treated |
| 0 | 242.7 ± 11.4 | 260.0 ± 16.3 | 245.0 ± 12.1 |
| 6 | 263.9 ± 13.5 | 278.1 ± 17.5 | 258.6 ± 14.6 |
| 9 | 270.1 ± 14.0 | 280.6 ± 19.2 | 260.1 ± 15.1 |
| 13 | 280.6 ± 16.2 | 290.3 ± 20.2 | 262.0 ± 15.1 |
| 16 | 283.8 ± 15.0 | 289.0 ± 18.5 | 261.1 ± 15.3 |
| 20 | 292.6 ± 16.1 | 284.1 ± 17.3 | 259.2 ± 14.6 |
| 23 | 299.8 ± 15.6 | 283.2 ± 17.0 | 252.7 ± 14.2 |
| 27 | 298.7 ± 14.0 | 276.1 ± 15.5 | 259.4 ± 14.4 |
| 30 | 307.6 ± 15.9 | 274.2 ± 3.4 | 260.9 ± 14.5 |
| 34 | 317.8 ± 16.2 | 262.6 ± 14.6 | 267.8 ± 15.1 |
| 37 | 318.1 ± 16.6 | 263.1 ± 15.0 | 268.4 ± 14.8 |
| 41 | 323.4 ± 15.3 | 264.4 ± 14.7 | 274.9 ± 15.2 |
| 44 | 328.5 ± 16.6 | 262.5 ± 14.6 | 278.3 ± 15.1 |
| 48 | 331.2 ± 17.0 | 263.0 ± 14.1 | 281.6 ± 15.0 |
| 49 | 330.5 ± 17.1 | 262.6 ± 14.4 | 281.2 ± 14.3 |

Tumor Size

Tumor size in control rats was compared to tumor size in vaccine treated rats over a four week period. Although no statistically significant differences were found between compared groups (due to large variation in tumor size), there was a strong trend toward decreasing total tumor volume (Table 21), and also decreased mean excised tumor weight (Table 22) in rats that received the vaccine.

TABLE 21

Change in tumor size between vehicle treated group (Tumor) and group treated with vaccine (Tumor treated). Shaded areas indicates dates when vaccine was administered.

| | Tumor Size ($cm^3$) | |
|---|---|---|
| Day | Tumor | Tumor Treated |
| 6 | 4.6 ± 2.1 | 4.7 ± 2.0 |
| 9 | 4.9 ± 2.0 | 4.8 ± 1.8 |
| 13 | 4.6 ± 1.8 | 5.0 ± 2.2 |
| 16 | 12.2 ± 2.7 | 12.3 ± 2.5 |
| 20 | 22.6 ± 3.8 | 13.4 ± 2.6 |
| 23 | 33.3 ± 4.8 | 14.1 ± 2.8 |
| 27 | 34.5 ± 4.6 | 13.8 ± 2.8 |
| 30 | 35.6 ± 4.6 | 13.5 ± 3.4 |
| 34 | 37.7 ± 8.0 | 14.1 ± 2.9 |
| 37 | 38.6 ± 10.2 | 13.7 ± 2.3 |
| 41 | 44.5 ± 12.1 | 12.5 ± 2.1 |
| 44 | 52.9 ± 13.9 | 13.0 ± 2.1 |
| 48 | 61.7 ± 15.1 | 16.9 ± 2.9 |

TABLE 22

Difference in tumor weight at necropsy.

| | Experimental Group | |
|---|---|---|
| | Tumor | Tumor Treated |
| Tumor weight (g) | 5.14 ± 6.08 | 1.24 ± 2.21 |

Serum Assays

Human alpha-feto protein (AFP) was measured by ELISA at various time-points during the study. These data were used in conjunction with body weight and tumor size data to randomize animals to treatment groups. Data from this study and historical data indicate that AFP is only detectable in tumor bearing animals. Comparison of longitudinal AFP data in the tumor control and treated groups indicates that AFP was decreased in the treated animals following first vaccine injection, and was much lower in treated rats relative to tumor bearing controls at the end of study; 4.78±3.2 ng/ml in vehicle treated relative to 0.97±2.5 ng/ml in vaccine treated rats, respectively. Additionally, AFP demonstrated a correlation to both tumor volume and excised tumor weight.

Human albumin (hALB) was measured by ELISA at various time-points during the study. Data from this study and historical data indicate that hALB is only detectable in tumor bearing animals. Comparison of hALB data in the tumor control and treated groups indicates that hALB was lower in treated rats relative to tumor bearing controls at the end of study (data not shown). Additionally, hALB, similar to AFP, demonstrated a correlation to both tumor volume and excised tumor weight (data not shown).

A core serum chemistry panel was assayed as various time-points throughout the study. The panel included: AST, ALT, Cholesterol, alkaline phosphatase, GGT, BUN, glucose, creatinine, total bilirubin, total protein, albumin, globulin and minerals Ca, P, Na, K and Cl. Similar to body weight, data was analyzed two ways: by treatment group and by tumor or non-tumor bearing animals. The only endpoints where differences were observed were: AST, ALT and cholesterol. By both comparisons, there were no significant differences among groups at the baseline time-point (data not shown). When comparing the chemistry indices in tumor bearing animals to non-tumor bearing animals, there was a significant difference between the groups at the terminal time point with elevations in AST, ALT and cholesterol in the tumor bearing animals (data not shown).

Conclusion

Taken together our data demonstrate that tumor burden was reduced in animals treated with vaccine prepared against the HepG2 tumor cell line, relative to control tumor-bearing group receiving vehicle.

Example 22

CpG

Background

The adjuvants described herein are a potent vaccine adjuvant platform that can be enhanced by using an ORN/ODN (CpG) to boost the immune response by using the adjuvants as a delivery system for the CpG.

Materials and Methods

Female C57BI/6 mice (n=10 per group) with a body weight of about 18-20 g were used in the study. They were immunized via intramuscular (IM) injection into the left tibialis anterior muscle with a total volume of 50 µl on study days 0, 14 and Reagent Dose A dose of the composition comprised, in various combinations, one or more of the following components:
  Buffer: NaH2PO4.2H20 (229.32 mg/L), NaCl (1168.00 mg/L) and Na2HPO4 (1144.00 mg/L), dissolved in WFI and sterile filtered with a 0.1 µm filter.
  Ovalbumin (OVA—Antigen): 10 µg
  CpG ODN: 10 µg
  Cholesterol: 1 µg
  Quil A: 1 µg
  DDA: 0.5 µg
  Carbopol: 0.0375%
  R1005: 50 µg Vaccine Preparation Buffer was placed in a 50 ml flask with stir bar and stirred at a constant speed throughout all following steps. The components were added in the following order: Antigen (OVA); CPG ODN; Quil A; cholesterol (drop wise); DDA (drop wise); Carbopol®; and Bay R1005®. The composition was stirred at room temperature (approximately 25° C.) for a minimum of 30 minutes while protected from light by covering with foil. The solution was forced through a 25 G needle into a syringe to break any large floating particles to obtain a uniform (cloudy) suspension and transferred to sterile glass vials for storage.

Sample Collection

The following samples were collected:
  Plasma: 4 weeks after the prime vaccination (1 week after second booster vaccination)
  Cytotoxic T lymphocyte (CTL) (6 weeks after the prime vaccination (3 weeks after second booster vaccination)
  Cytokine secretion in supernatant (4 weeks after the prime vaccination
  24-hour supernatant (IL-2, IL-4, IL-10, TNF
  72-hour supernatant (IFN-g
  Tetramer (4 weeks after the prime vaccination
  Cytokine producing T cells (6 weeks after the prime vaccination The results are provided as a relative score that for each adjuvant showing the effect of the adjuvant. The endpoints are a relative scale based on the sum of the individual Cytotoxic T—Lymphocyte responses.

Results and Discussion

As presented in Table 23, QCDCR plus OVA gave stronger CTL responses than its subcomponents, however overall responses were low (<20%). Combining QCDCR or its subcomponents with CPG significantly improved OVA-specific CTL responses. Overall QCDCR/CPG plus OVA gave the highest CTL response, however, there was no significant difference in responses between this group and cholesterol/CPG plus OVA (at 25:1 ratio). Culture supernatants from splenocytes stimulated with OVA (1 mg/ml) were assayed for cytokines by ELISA. QCDCR alone or its subcomponents gave only very weak cytokine responses. Combining QCDCR or its subcomponents with CPG enhanced secretion of antigen specific IL-2 and IFN-g (Th1-biased cytokines). QCDCR and CpG are equal in potency for augmenting cellular immune responses. Combining the two shows synergy. When sub-components of QCDCR were analyzed with CpG, combinations with Quil A gave the best responses followed by inclusion of cholesterol with CpG.

TABLE 23

Relative CTL Responses

| Groups | CTL | IFN-g | Tetramer | IL-2 | Total |
| --- | --- | --- | --- | --- | --- |
| QCDCR – CpG + OVA | 18 | 16 | 18 | 18 | 70 |
| QCDC – CpG + OVA | 15 | 18 | 17 | 16 | 66 |
| Ch + CpG + CR + OVA | 12 | 14 | 15 | 17 | 58 |
| Ch + CpG + DC + OVA | 8 | 17 | 13 | 15 | 53 |
| Ch + CpG + DCR + OVA | 16 | 9 | 14 | 13 | 52 |
| C + CpG + OVA | 9 | 13 | 16 | 11 | 48 |
| DCR + CpG + OVA | 13 | 13 | 12 | 9 | 47 |
| CR + CpG + OVA | 10 | 10 | 11 | 8 | 39 |
| DC + CpG + OVA | 11 | 11 | 8 | 6 | 36 |
| CpG + OVA | 14 | 8 | 9 | 3 | 34 |
| QCDCR + OVA | 7 | 5 | 7 | 14 | 33 |
| CR + OVA | 5 | 7 | 4 | 7 | 23 |
| QCDC + OVA | 3 | 6 | 2 | 10 | 21 |
| CR + OVA | 4 | 3 | 5 | 4 | 16 |
| DCR + OVA | 6 | 2 | 6 | 2 | 16 |
| DC + OVA | 2 | 4 | 3 | 5 | 14 |
| OVA | 1 | 1 | 1 | 1 | 4 |

QC is the abbreviation for QuilA/cholesterol,
Ch for cholesterol,
D for DDA,
C for Carbopol®,
R for Bay R1005 ®

Example 23

Canine Coronavirus (CCV)

Scope

A murine model was employed using canine coronavirus (CCV) and novel combination adjuvants to evaluate the adjuvant performance with the given antigenic component.

Animals

Ten CF-1 mice per treatment group were administered 0.2 mL subcutaneously per animal of each treatment group.

Treatment Groups

The test formulations shown in Table 24 were prepared as 1.0 mL field dose volumes with the concentrations given below. Only 0.2 mL of the vaccine was administered to each mouse.

TABLE 24

Test Formulations.

| Item # | Test Formulations | Adj. Concentration: µg/2 mL (except Carbopol) | CCV/dose |
|---|---|---|---|
| 1 | PBS | NA | na |
| 2 | Antigen | PBS | 6,040 |
| 3 | AbISCO-100 | 100 | 6,040 |
| 4 | AbISCO-200 | 100 | 6,040 |
| 5 | AbISCO-300 | 100 | 6,040 |
| 6 | Quil-A/Cholesterol | 100/100 | 6,040 |
| 7 | R1005 | 1000 | 6,040 |
| 8 | R1005/Carbopol | 1000/0.075% | 12,079 |
| 9 | DDA/R1005/Carbopol | 50/1000/0.075% | 12,079 |
| 10 | Quil-A/Cholesterol/R1005 | 100/100/1000 | 6,040 |
| 11 | Quil-A/Cholesterol/DDA Carbopol | 100/100/50/0.075% | 6,040 |
| 12 | Quil-A/Cholesterol/R1005/Carbopol | 100/100/1000/0.075% | 12,079 |
| 13 | Quil-A/Cholesterol/DDA/R1005/Carbopol | 100/100/50/1000/0.075% | 12,079 |

Vaccine Preparation

Vaccine preparation for the adjuvants of the invention is described in Examples 1-13 above. The concentrations of adjuvant components are provided in Table 24. Adjuvants were added in the order listed in the Table.

A saline extender was added to a vessel and homogenization was initiated. Inactivated CCV was added to a concentration shown in Table 24. Quil A was added at the concentration listed in Table 24. The cholesterol in ethanol solution was then added with continued homogenization. The DDA/ethanol solution was then added during homogenization. The mixture was microfluidized at 10,000 psi. Carbopol was then added with mixing and the pH was adjusted to 6.8 to 7.2. Bay R1005® glycolipid was then added with mixing. Finally, the composition was brought to final volume with the saline extender.

The vaccine for the treatment groups receiving the commercially available AbISCO products (Isconova, Sweden) was prepared according to the label instructions. AbISCO products are based on quillaja saponins and ISCOM technology using highly purified saponins.

Assay Method: The Beta CCV Serum Neutralization

The serum was heat inactivated at 56 C for 30 to 40 minutes. In a clean sterile plate, serial dilutions of each sera (undiluted, 2, 4, 8 . . . ) was performed by passing 120 µl into 120 µl diluent. At least two replicate wells/dilution were used. A dilution of 1:16 was used initially, if necessary. A working challenge stock was prepared by diluting live CCV to a level containing about 240 virus particles in 120 µl. Then, 120 µl of each serum dilution was combined with 120 µl of virus solution for a total of 240 µl. The solution was mixed and held at room temperature (approximately 25°) for 30 to 60 minutes to allow for neutralization. Then 120 µl of each serial was transferred onto waiting naked monolayers of NLFK cells planted 7 to 12 days earlier. CPE was assessed 4 to 6 days later. The back titration confirmed that 50 to 316 virus particles hit each monolayer.

Results

TABLE 25

Serum Neutralization

| Treatment Group | Serum Neutralizing Titers |
|---|---|
| Saline | 2 |
| Antigen only | 64 |
| AbISCO-100 | 256 |
| AbISCO-200 | 23 |
| AbISCO-300 | 11 |
| Quil-A/Cholesterol | 315 |
| R | 512 |
| RC | 11 |
| DRC | 630 |
| QCR | 1024 |
| QCDC | 630 |
| QCRC | 724 |
| QCDRC | 1448 |

Summary

The combined effects of the adjuvants formulated with CCV taking into account the chemical properties of each component have provided excellent properties for a vaccine adjuvant.

The serological results of the study are shown in Table 25. Higher serum neutralizing antibody titers generally are associated with better protection afforded by the vaccines. Several of the adjuvant formulations of the invention produced much higher titers than the commercial adjuvanted products, even though these formulations had a similar amount of CCV antigen added. The QCDC, QCR, DRC, QCRC, and QCDRC formulations were especially effective in inducing a good immune response in the mice.

Example 24

Bovine Rotavirus Antigen

Scope

A murine model was employed using Bovine Rotavirus and combination adjuvants of the invention to evaluate the adjuvant performance with the given antigenic component.

Animals

Ten CF-1 mice per treatment group were administered 0.2 mL subcutaneously per animal for each treatment group.

Treatment Groups

The test formulations shown in Table 26 were prepared as 2.0 mL field dose volumes with the concentrations given below. Only 0.2 mL of the vaccine was administered to each animal.

TABLE 26

Test Formulations

| Item # | Test Formulations | Adj. concentration: µg/2 mL (except Carbopol) | Rotavirus B223/dose |
|---|---|---|---|
| 1 | Phosphate buffer | PBS | NA |
| 2 | Antigen | PBS | 6.09 µg |
| 3 | AbISCO-100 | 100 | 6.09 µg |
| 4 | AbISCO-200 | 100 | 6.09 µg |
| 5 | AbISCO-300 | 100 | 6.09 µg |
| 6 | Quil-A/Cholesterol | 100/100 | 6.09 µg |
| 7 | Quil-A/Cholesterol/DDA Carbopol | 100/100/50/0.075% | 6.09 µg |
| 8 | R1005 | 1000 | 6.09 µg |
| 9 | Quil-A/Cholesterol/R1005 | 100/100/1000 | 6.09 µg |
| 10 | Quil-A/Cholesterol/DDA/R1005/Carbopol | 100/100/50/1000/0.075% | 6.09 µg |
| 11 | Quil-A/Cholesterol/DDA/Carbopol | 100/100/50/0.075% | 12.18 µg |

TABLE 26-continued

Test Formulations

| Item # | Test Formulations | Adj. concentration: μg/2 mL (except Carbopol) | Rotavirus B223/dose |
|---|---|---|---|
| 12 | Quil-A/Cholesterol/Carbopol/R1005 | 100/100/0.075%/1000 | 12.18 μg |
| 13 | Quil-A/Cholesterol/DDA/R1005/Carbopol | 100/100/50/1000/0.075% | 12.18 μg |
| 14 | DDA/R1005/Carbopol | 50/1000/0.075% | 12.18 μg |
| 15 | R1005/Carbopol | 1000/0.075% | 12.18 μg |

Vaccine Preparation

Vaccine preparation for the adjuvants of the invention is described in Examples 1-13 above. The concentrations of adjuvant components are provided in Table 26. Adjuvants were added in the order listed in the Table.

A saline extender was added to a vessel and homogenization was initiated. Inactivated Bovine Rotavirus was added to a concentration shown in Table 26. Quil A was added at the concentration listed in Table 26. The cholesterol/ethanol solution was then added with continued homogenization. The DDA/ethanol solution was then added during homogenization. The mixture was microfluidized at 10,000 psi. Carbopol® was then added with mixing and the pH was adjusted to 6.8 to 7.2. Bay R1005® glycolipid was then added with mixing. Finally, the composition was brought to final volume with the saline extender.

The vaccine for the treatment groups receiving the commercially available AbISCO products (Isconova, Sweden) was prepared according to the label instructions. AbISCO products are based on quillaja saponins and ISCOM technology using highly purified saponins.

Results

TABLE 27

Serum Neutralization Titers

| Test Formulations | Serum Neutralizing Titers (SN) |
|---|---|
| Saline | ≤3 |
| Antigen only | 23 |
| AbISCO-100 | 16 |
| AbISCO-200 | 16 |
| AbISCO-300 | 14 |
| Quil-A/Cholesterol | 14 |
| QCDC | 16 |
| R | 10 |
| QCR | 16 |
| QCDCR | 16 |
| QCDC | 3 |
| QCCR | 5 |
| QCDCR | 39 |
| DRC | 20 |
| RC | 3 |

QC is the abbreviation for QuilA/cholesterol,
D for DDA,
C for Carbopol ®,
R for Bay R1005 ®

The combined effects of the adjuvants formulated with Bovine Rotavirus and taking into account the chemical properties of each component have provided excellent properties for a vaccine adjuvant (see Table 27).

While several of the adjuvant formulations provided similar levels of serum neutralizing antibody titers, the QCDCR adjuvant provided the highest level.

Example 25

Canine Influenza Virus

Scope/Study Design

A canine model was employed using canine influenza virus (CIV) and novel combination adjuvants to evaluate the adjuvant performance with the given antigenic component.

This study had a randomized complete block design. (see Table 28) Animals were sorted by date of birth to form blocks of size 5. Within a block animals were randomly assigned to treatments. Animals in the same block were randomly assigned to pens (cages) located near each other. Animals were in good health with no history of hypersensitivity to commercially available vaccines. Animals had not received vaccines against CIV.

TABLE 28

Study Design

| Trmt Group | # of Animals | Treatment | Day | Dose | Route |
|---|---|---|---|---|---|
| T01 | 8-10 | Adjuvant Placebo (neg control) | 0 | 1 mL | SQ |
| T02 | 8-10 | Field Safety study formulation (pos control) | 0 | 1 mL | SQ |
| T03 | 8-10 | QCDC high dose | 0 | 1 mL | SQ |
| T04 | 8-10 | QCDC medium dose | 0 | 1 mL | SQ |
| T05 | 8-10 | QCDC low dose | 0 | 1 mL | SQ |

QC is the abbreviation for QuilA/cholesterol,
D for DDA,
C for Carbopol ®

TABLE 29

Vaccine Composition

Adjuvant placebo, negative control

T01

| Formulation | Quil A - cholesterol - DDA - carbopol (20/20/10/.075) |

T02

| Generic Name | CIV field safety serial, positive control |
| Formulation | Iowa-05 strain of influenza (H3N8) @ 760 HA, combined with 5% Rehydragel LV |

T03

| Generic Name | CIV + high dose QCDC |
| Formulation | Iowa-05 strain of influenza (H3N8) @ 760 HA, combined with Quil A - cholesterol - DDA - carbopol (20/20/10/.075) |

T04

| Generic Name | CIV + medium dose QCDC |
| Formulation | Iowa-05 strain of influenza (H3N8) @ 760 HA, combined with Quil A - cholesterol - DDA - carbopol (10/10/10/.075) |

T05

| Generic Name | CIV + low dose QCDC |
| Formulation | Iowa-05 strain of influenza (H3N8) @ 760 HA, combined with Quil A - cholesterol - DDA - carbopol (5/5/10/.075) |

Vaccine Preparation

Vaccine preparation for the adjuvants of the invention is described in Examples 1-13 above. The concentrations of adjuvant components are provided in Table 29. Adjuvants were added in the order listed in the Table.

A saline extender was added to a vessel and homogenization was initiated. Inactivated canine influenza virus was added to a concentration shown in Table 29. Quil A was added at the concentration listed in Table 29. The cholesterol/ethanol solution was then added with continued homogenization. The DDA/ethanol solution was then added during homogenization. The mixture was microfluidized at 10,000 psi. Carbopol was then added with mixing and the pH was adjusted to 6.8 to 7.2. Finally, the composition was brought to final volume with the saline extender.

Testing

Serology was assessed by using hemeagglutination inhibition (HAI) assay by Standard Assay Method per the USDA Results/Summary Presented in Table 30 are THE serological results on days 42 and 180 of the HAI Geo. mean titers.

TABLE 30

| | HAI Titers | |
|---|---|---|
| Treatment | HAI Geo. Mean Day 42 | HAI Geo. Mean Day 180 |
| T01 (placebo) | 8 | 8 |
| T02 (pos ctl., alum) | 172 | 32 |
| T03 (low dose) | 65 | 41 |
| T04 (med. dose) | 65 | 32 |
| T05 (high dose) | 216 | 69 |

The combined effects of the adjuvants formulated with influenza virus and taking into account the chemical properties of each component have provided excellent properties for a vaccine adjuvant.

Higher antibody titers generally are associated with better protection of vaccines. Generally, both the aluminum adjuvant (T02) and the adjuvants of the invention (T03, T04, and T05) caused a rise in HAI titers but the response caused by the adjuvants of the invention was superior with higher titers at day 180 in the high dose group (T05). The titers for the low- and medium-doses of the adjuvants of the invention were equivalent to those of the traditional aluminum-containing vaccine for influenza. Additionally, because the adjuvants of the invention provide a T helper 1 immune response whereas aluminum does not, the duration of immunity is expected to be longer with a faster recall mechanism.

What is claimed is:

1. A vaccine composition comprising a therapeutically effective amount of an antigen component and an adjuvant formulation comprising a triterpenoid saponin, a sterol, a quaternary ammonium compound, and a polyacrylic acid polymer, wherein the antigen component comprises Feline Leukemia Virus.

2. The vaccine composition of claim 1, wherein the saponin is present in an amount of about 1 mg to about 5,000 mg per dose, the sterol is present in an amount of about 1 mg to about 5,000 mg per dose, the quaternary ammonium compound is present in an amount of about 1 mg to about 5,000 mg per dose, and the polyacrylic acid polymer is present in an amount of about 0.0001% v/v to about 75% v/v.

3. The vaccine composition of claim 1, wherein the saponin is Quil A or a purified fraction thereof, the sterol is cholesterol, and the quaternary ammonium compound is dimethyl dioctadecyl ammonium bromide (DDA).

4. The vaccine composition of claim 1, wherein the antigen component further comprises at least one of Feline Immunodeficiency Virus, Feline Viral Rhinotracheitis virus, Feline Calicivirus, Feline Enteric Coronavirus, Feline Infectious Peritonitis Virus, and *Chlamydia psittaci*.

5. The vaccine composition of claim 1, wherein the antigen component further comprises Feline Immunodeficiency Virus.

6. The vaccine composition of claim 1, wherein the antigen component further comprises at least one of Feline Calicivirus and Feline Rhinotracheitis Virus.

7. The vaccine composition of claim 1, wherein the antigen component further comprises Feline Calicivirus, Feline Rhinotracheitis Virus, and *Chlamydia Psittachi*.

8. The vaccine composition of claim 1, wherein the adjuvant formulation consists of the triterpenoid saponin, the sterol, the quaternary ammonium compound, and the polyacrylic acid polymer.

9. The vaccine composition of claim 8, wherein the saponin is present in an amount of about 1 mg to about 5,000 mg per dose, the sterol is present in an amount of about 1 mg to about 5,000 mg per dose, the quaternary ammonium compound is present in an amount of about 1 mg to about 5,000 mg per dose, and the polyacrylic acid polymer is present in an amount of about 0.0001% v/v to about 75% v/v.

10. The vaccine composition of claim 8, wherein the saponin is Quil A or a purified fraction thereof, the sterol is cholesterol, and the quaternary ammonium compound is dimethyl dioctadecyl ammonium bromide (DDA).

11. The vaccine composition of claim 8, wherein the antigen component further comprises at least one of Feline Immunodeficiency Virus, Feline Viral Rhinotracheitis virus, Feline Calicivirus, Feline Enteric Coronavirus, Feline Infectious Peritonitis Virus, and *Chlamydia psittaci*.

12. The vaccine composition of claim 8, wherein the antigen component further comprises Feline Immunodeficiency Virus.

13. The vaccine composition of claim 8, wherein the antigen component further comprises at least one of Feline Calicivirus and Feline Rhinotracheitis Virus.

14. The vaccine composition of claim 8, wherein the antigen component further comprises Feline Calicivirus, Feline Rhinotracheitis Virus, and *Chlamydia Psittachi*.

15. A method of preventing an infection with Feline Leukemia Virus in a cat in need thereof, comprising administering to said cat the vaccine composition of claim 1.

16. A method of preventing an infection with Feline Leukemia Virus in a cat in need thereof, comprising administering to said cat the vaccine composition of claim 8.

* * * * *

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
ggtggtgcta agcgtgttat                                              20

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
acctctgtca tctctccaca                                              20

<210> SEQ ID NO 3
<211> LENGTH: 22
<212> TYPE: DNA
<213> ORGANISM: Artificial Sequence
<220> FEATURE:
<223> OTHER INFORMATION: primer

<400> SEQUENCE: 3
agctgacggt ggacctatta tt                                           22

<210> SEQ ID NO 4
<211> LENGTH: 17
<212> TYPE: DNA
<213> ORGANISM: Artificial Sequence
<220> FEATURE:
<223> OTHER INFORMATION: primer
```

```
<400> SEQUENCE: 4
ggctttgcgc tggattc                                                      17

<210> SEQ ID NO 5
<211> LENGTH: 18
<212> TYPE: DNA
<213> ORGANISM: Artificial Sequence
<220> FEATURE:
<223> OTHER INFORMATION: primer

<400> SEQUENCE: 5
tgggcatcaa gggctaca                                                     18

<210> SEQ ID NO 6
<211> LENGTH: 18
<212> TYPE: DNA
<213> ORGANISM: Artificial Sequence
<220> FEATURE:
<223> OTHER INFORMATION: primer

<400> SEQUENCE: 6
tcgggttggt tggtgatg                                                     18

<210> SEQ ID NO 7
<211> LENGTH: 24
<212> TYPE: DNA
<213> ORGANISM: Artificial Sequence
<220> FEATURE:
<223> OTHER INFORMATION: primer

<400> SEQUENCE: 7
tctgttcttc tgttctgagt gatg                                              24

<210> SEQ ID NO 8
<211> LENGTH: 24
<212> TYPE: DNA
<213> ORGANISM: Artificial Sequence
<220> FEATURE:
<223> OTHER INFORMATION: primer

<400> SEQUENCE: 8
agtgatttgc ttctgtcttt ggta                                              24
```